US011136354B2

(12) United States Patent
Curtiss, III

(10) Patent No.: US 11,136,354 B2
(45) Date of Patent: Oct. 5, 2021

(54) PROTECTIVE ANTI-ZIKV VACCINE WITHOUT INDUCING CROSS-REACTIONS WITH DENGUE

(71) Applicant: UNIVERSITY OF FLORIDA RESEARCH FOUNDATION, INC., Gainesville, FL (US)

(72) Inventor: Roy Curtiss, III, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 50 days.

(21) Appl. No.: 16/319,363

(22) PCT Filed: Jul. 24, 2017

(86) PCT No.: PCT/US2017/043511
§ 371 (c)(1),
(2) Date: Jan. 21, 2019

(87) PCT Pub. No.: WO2018/018041
PCT Pub. Date: Jan. 25, 2018

(65) Prior Publication Data
US 2019/0185520 A1    Jun. 20, 2019

Related U.S. Application Data

(60) Provisional application No. 62/365,549, filed on Jul. 22, 2016, provisional application No. 62/467,340, filed on Mar. 6, 2017.

(51) Int. Cl.
C07K 14/005    (2006.01)
A61K 39/12     (2006.01)
C12N 1/20      (2006.01)
C12N 1/36      (2006.01)
A61K 39/00     (2006.01)
C12R 1/42      (2006.01)

(52) U.S. Cl.
CPC .......... C07K 14/005 (2013.01); A61K 39/12 (2013.01); C12N 1/20 (2013.01); C12N 1/36 (2013.01); A61K 2039/522 (2013.01); A61K 2039/523 (2013.01); A61K 2039/53 (2013.01); C12N 1/205 (2021.05); C12N 2770/24122 (2013.01); C12N 2770/24134 (2013.01); C12N 2770/24162 (2013.01); C12N 2770/24171 (2013.01); C12R 2001/42 (2021.05); Y02A 50/30 (2018.01)

(58) Field of Classification Search
None
See application file for complete search history.

(56) References Cited

U.S. PATENT DOCUMENTS

| 6,872,547 | B1 | 3/2005 | Curtiss |
| 9,050,285 | B2* | 6/2015 | Curtiss, III ............. A61P 31/04 |
| 10,611,801 | B2* | 4/2020 | Barouch ................ C07K 16/10 |
| 2006/0140975 | A1* | 6/2006 | Curtiss ................. A61K 39/092 424/200.1 |
| 2012/0087946 | A1 | 4/2012 | Curtiss et al. |
| 2013/0171190 | A1 | 7/2013 | Curtiss et al. |
| 2019/0030157 | A1* | 1/2019 | Guirakhoo .............. A61P 31/14 |

FOREIGN PATENT DOCUMENTS

WO    WO 2017/015463 A2 *    1/2017

OTHER PUBLICATIONS

Zhu et al. Emerging Microbes and Infections (2016) 5, e22; doi:10.1038/emi.2016.48 published online Mar. 16, 2016.*
Ameiss, K. et al. "Delivery of woodchuck hepatitis virus-like particle presented influenza M2e by recombinant attenuated *Salmonella* displaying a delayed lysis phenotype" *Vaccine*, 2010, pp. 6704-6713, vol. 28.
Ashraf, S. et al. "Protective cellular responses elicited by vaccination with influenza nucleoprotein delivered by a live recombinant attenuated *Salmonella* vaccine" *Vaccine*, 2011, pp. 3990-4002, vol. 29.
Barba-Spaeth, G. et al. "Structural basis of potent Zika-dengue virus antibody cross-neutralization" *Nature*, Aug. 4, 2016, pp. 48-67, vol. 536, Methods pp. 1-14.
Bertani, G. "The Mode of Phage Liberation by Lysogenic *Escherichia coli*" *Studies on Lysogenesis*, 1951, pp. 293-300, vol. 62.
Cortazzo, P. et al. "Silent mutations affect in vivo protein folding in *Escherichia coli*" *Biochemical and Biophysical Research Communications*, 2002, pp. 537-541, vol. 293.
Curtiss, R. et al. "Nonrecombinant and Recombinant Avirulent *Salmonella* Live Vaccines for Poultry" *Colonization Control of Human Bacterial Enteropathogens in Poultry*, 1991, pp. 169-198.
Curtiss, R. et al. "*Salmonella enterica* Serovar Typhimurium Strains with Regulated Delayed Attenuation in Vivo" *Infection and Immunity*, Mar. 2009, pp. 1071-1082, vol. 77, No. 3.
Curtiss, R. et al. "New Technologies in Using Recombinant Attenuated *Salmonella* Vaccine Vectors" *Crit Rev Immunol.*, 2010, pp. 255-270, vol. 30, No. 3.

(Continued)

Primary Examiner — Oluwatosin A Ogunbiyi
(74) Attorney, Agent, or Firm — Saliwanchik, Lloyd & Eisenschenk

(57) ABSTRACT

The subject application provides a genetically modified recombinant facultative intracellular invasive bacterial pathogen (RFIIBP) or a recombinant attenuated *Salmonella* vaccine (RASV) strains encoding Zika virus (ZIKV) antigens. These strains exhibit high immunogenicity, complete safety, and attenuation, and are unable to persist or be shed in an infective or viable form. These RFIIBPs and RASVs also exhibit regulated delayed attenuation in vivo, regulated delayed in vivo synthesis of protective ZIKV antigens. Methods of inducing mucosal, systemic and cellular immunities in hosts are also provided and antibodies produced using the disclosed RFIIBPs and RASVs can comprise neutralizing antibodies against ZIKV that do not crossreact with Dengue virus (DENV).

11 Claims, 37 Drawing Sheets

Specification includes a Sequence Listing.

(56) References Cited

OTHER PUBLICATIONS

Ehretsmann, C.P. et al. "Specificity of *Escherichia coli* endoribonuclease RNase E: in vivo and in vitro analysis of mutants in a bacteriophage T4 mRNA processing site" *Genes & Development*, 1992, pp. 149-159, vol. 6.

Fluman, N. et al. "mRNA-programmed translation pauses in the targeting of *E.coli* membrane proteins" *eLife*, 2014, pp. 1-19, doi:10.7554/eLife.03440.

Galán, J. E. et al. "Cloning and characterization of the asd gene of *Salmonella typhimurium*: use in stable maintenance of recombinant plasmids in *Salmonella* vaccine strains" *Gene*, 1990, pp. 29-35, vol. 94.

Gingold, H. et al. "Determinants of translation efficiency and accuracy" *Molecular Systems Biology*, 2011, pp. 1-13, vol. 7, No. 481.

Hitchcock, P. J. et al. "Morphological Heterogeneity Among *Salmonella* Lipopolysaccharide Chemotypes in Silver-Stained Polyacrylamide Gels" *Journal of Bacteriology*, Apr. 1, 1983, pp. 269-277, vol. 154, No. 1.

Jiang, Y. et al. "Protection Against Necrotic Enteritis in Broiler Chickens by Regulated Delated Lysis *Salmonella* Vaccines" *Avian Diseases*, 2015, pp. 475-485, vol. 59, No. 4.

Juárez-Rodríguez, M.D. et al. "Live Attenuated *Salmonella* Vaccines against *Mycobacterium tuberculosis* with Antigen Delivery via the Type III Secretion System" *Infection and Immunity*, 2012, pp. 798-814. vol. 80, No. 2.

Kappes et al. "Vaccination with NS1-Truncated H3N2 Swine Influenza Virus Primes T Cells and Confers Cross-Protection against an H1N1 Heterosubtypic Challenge in Pigs" *Vaccine*, 2012, pp. 280-288, vol. 30.

Kimchi-Sarfaty, C. et al. "A "Silent" Polymorphism in the MDR1 Gene Changes Substrate Specificity" *Science*, Jan. 26, 2007, pp. 525-528, vol. 315.

Komar, A. A. et al. "Synonymous codon substitutions affect ribosome traffic and protein folding during in vitro translation" *FEBS Letters*, 1999, pp. 387-391, vol. 462.

Kong, W. et al. "Regulated programmed lysis of recombinant *Salmonella* in host tissues to release protective antigens and confer biological containment" *PNAS*, Jul. 8, 2008, pp. 9361-9366, vol. 105, No. 27.

Kong, W. et al. "Turning self-destructing *Salmonella* into a universal DNA vaccine delivery platform" *PNAS*, Nov. 20, 2012, pp. 19414-19419, vol. 109, No. 47, Supporting information pp. 1-7.

Kong, W. et al. "Utilizing *Salmonella* for antigen delivery: the aims and benefits of bacterial delivered vaccination" *Expert Review of Vaccines*, 2013, pp. 345-347, vol. 12, No. 4.

Larocca, R.A. et al. "Vaccine protection against Zika virus from Brazil" *Nature*, Aug. 25, 2016, pp. 474-488, vol. 536.

Lin-Chao, S. et al. "Effects of Nucleotide Sequence on the Specificity of me-dependent and RNase E-mediated Cleavages of RNA I Encoded by the pBR322 Plasmid" *The Journal of Biological Chemistry*, Apr. 8, 1994, pp. 10797-10803, vol. 269, No. 14.

McDowall, K. J. et al. "Site-specific RNase E cleavage of oligonucleotides and inhibition by stem-loops" *Nature*, Mar. 16, 1995, pp. 287-290, vol. 374.

Nicholson, C. O. et al. "Viral entry inhibitors block dengue antibody dependent enhancement in vitro" *Antiviral Research*, 2011, pp. 71-74, vol. 89.

Sasaki, T. et al. "Dengue virus neutralization and antibody-dependent enhancement activities of human monoclonal antibodies derived from dengue patients at acute phase of secondary infection" *Antiviral Research*, 2013, pp. 423-431, vol. 98.

Shi, H. et al. "Live Recombinant *Salmonella* Typhi Vaccines Constructed to Investigate the Role of rpoS in Eliciting Immunity to a Heterologous Antigen" *PLoS One*, Jun. 2010, p. 1-19, vol. 5, Issue 6, e11142.

Wang, S. et al. "New technologies in developing recombinant attenuated *Salmonella* vaccine vectors" *Microbial Pathogenesis*, 2013, pp. 17-28, vol. 58.

Zhang, X. et al. "Characterization and Immunogenicity of *Salmonella typhimurium* SL1344 and UK-1 Δcrp and Δcdt Deletion Mutants" *Infection and Immunity*, Dec. 1997, pp. 5381-5387, vol. 65, No. 12.

Written Opinion in International Application No. PCT/US17/43511, dated Oct. 12, 2017, pp. 1-8.

* cited by examiner

Capsid protein C 309 bp, (103 aa)

22 aa codon optimized (29 bp changed)

```
1/1                                    31/11
ATG AAA AAC CCA AAA AAG AAA TCC GGA GGA TTC CGG ATT GTC AAT ATG CTA AAA CGC GGA
ATG AAA AAC CCA AAA AAG AAA TCC GGT GGT TTC CGT ATT GTC AAT ATG CTG AAA CGC GGT
 M   K   N   P   K   K   K   S   G   G   F   R   I   V   N   M   L   K   R   G

61/21                                  91/31
GTA GCC CGT GTG AGC CCC TTT GGG GGC TTG AAG AGG CTG CCA GCC GGA CTT CTG CTG GGT
GTA GCC CGT GTG AGC CCG TTT GGC GGC TTG AAG CGT CTG CCA GCC GGC CTG CTG CTG GGT
 V   A   R   V   S   P   F   G   G   L   K   R   L   P   A   G   L   L   L   G

121/41                                 151/51
CAT GGG CCC ATC AGG ATG GTC TTG GCG ATT CTA GCC TTT TTG AGA TTC ACG GCA ATC AAG
CAT GGG CCG ATC CGT ATG GTC CTG GCG ATT CTG GCC TTT CTG CGT TTC ACG GCA ATC AAG
 H   G   P   I   R   M   V   L   A   I   L   A   F   L   R   F   T   A   I   K

181/61                                 211/71
CCA TCA CTG GGT CTC ATC AAT AGA TGG GGT TCA GTG GGG AAA AAA GAG GCT ATG GAA ACA
CCA TCA CTG GGT CTC ATC AAT CGT TGG GGT TCA GTG GGG AAA AAA GAG GCT ATG GAA ACA
 P   S   L   G   L   I   N   R   W   G   S   V   G   K   K   E   A   M   E   T

241/81                                 271/91
ATA AAG AAG TTC AAG AAA GAT CTG GCT GCC ATG CTG AGA ATA ATC AAT GCT AGG AAG GAG
ATC AAG AAG TTC AAG AAA GAT CTG GCT GCC ATG CTG CGC ATT ATC AAT GCT CGC AAG GAG
 I   K   K   F   K   K   D   L   A   A   M   L   R   I   I   N   A   R   K   E

301/101
AAG AAG AGA  (SEQ ID NO: 1)
AAG AAG CGC  (SEQ ID NO: 2)
 K   K   R   (SEQ ID NO: 3)
```

FIGURE 3 prM 288 bp (96 aa) optimized and 279 bp (93 aa) original
12 aa (18 bp) codon optimized and 3 N-terminal codons added

```
1/1                                                     31/11
            GCG GAG GTC ACT AGA CGT GGG AGT GCA TAC TAT ATG TAC TTG GAC AGA AAC
ATG AAA AAG GCG GAG GTC ACT CGT CGT GGT AGC GCA TAC TAT ATG TAC CTG GAC CGC AAC
 M   K   K   A   E   V   T   R   R   G   S   A   Y   Y   M   Y   L   D   R   N

61/21                                                   91/31
GAT GCT GGG GAG GCC ATA TCT TTT CCA ACC ACA TTG GGG ATG AAT AAG TGT TAT ATA CAG
GAT GCT GGC GAG GCC ATC TCT TTT CCA ACC ACC TTG GGT ATG AAT AAG TGT TAT ATC CAG
 D   A   G   E   A   I   S   F   P   T   T   L   G   M   N   K   C   Y   I   Q

121/41                                                  151/51
ATC ATG GAT CTT GGA CAC ATG TGT GAT GCC ACC ATG AGC TAT GAA TGC CCT ATG CTG GAT
ATC ATG GAT CTG GGC CAC ATG TGT GAT GCC ACC ATG AGC TAT GAA TGC CCT ATG CTG GAT
 I   M   D   L   G   H   M   C   D   A   T   M   S   Y   E   C   P   M   L   D

181/61                                                  211/71
GAG GGG GTG GAA CCA GAT GAC GTC GAT TGT TGG TGC AAC ACG ACG TCA ACT TGG GTT GTG
GAG GGG GTG GAA CCA GAT GAC GTC GAT TGT TGG TGC AAC ACG ACG TCA ACT TGG GTT GTG
 E   G   V   E   P   D   D   V   D   C   W   C   N   T   T   S   T   W   V   V

241/81                                  271/91
TAC GGA ACC TGC CAT CAC AAA AAA GGT GAA GCA CGG AGA TCT AGA AGA  (SEQ ID NO: 4)
TAC GGT ACC TGC CAT CAC AAA AAA GGT GAA GCA CGC CGC TCT CGC CGC  (SEQ ID NO: 5)
 Y   G   T   C   H   H   K   K   G   E   A   R   R   S   R   R  (SEQ ID NO: 6)
```

FIGURE 4

E protein 1518 bp (506 aa) in codon optimized and 1512 bp (504 aa) in original Codon for aa 156(154 in original) and 483 (481 in orginal) changed to cod Q in place of N.54 aa (72 bp) codon optimized and 2 N-terminal codons added

```
1/1                                          31/11
         ATC AGG TGC ATA GGA GTC AGC AAT AGG GAC TTT GTG GAA GGT ATG TCA GGT GGG
ATG AAA ATC CGC TGC ATC GGT GTC AGC AAT CGT GAC TTT GTG GAA GGT ATG TCC GGT GGT
 M   K   I   R   C   I   G   V   S   N   R   D   F   V   E   G   M   S   G   G

61/21                                        91/31
ACT TGG GTT GAT GTT GTC TTG GAA CAT GGA GGT TGT GTC ACC GTA ATG GCA CAG GAC AAA
ACT TGG GTT GAT GTT GTC CTG GAA CAT GGC GGT TGT GTC ACC GTA ATG GCA CAG GAC AAA
 T   W   V   D   V   V   L   E   H   G   G   C   V   T   V   M   A   Q   D   K

121/41                                       151/51
CCG ACT GTC GAC ATA GAG CTG GTT ACA ACA ACA GTC AGC AAC ATG GCG GAG GTA AGA TCC
CCG ACT GTC GAC ATC GAG CTG GTT ACC ACC ACC GTC AGC AAC ATG GCG GAG GTA CGT TCC
 P   T   V   D   I   E   L   V   T   T   T   V   S   N   M   A   E   V   R   S

181/61                                       211/71
TAC TGC TAT GAG GCA TCA ATA TCA GAC ATG GCT TCT GAC AGC CGC TGC CCA ACA CAA GGT
TAC TGC TAT GAG GCA TCC ATC TCC GAC ATG GCT TCT GAC AGC CGC TGC CCA ACC CAA GGT
 Y   C   Y   E   A   S   I   S   D   M   A   S   D   S   R   C   P   T   Q   G

241/81                                       271/91
GAA GCC TAC CTT GAC AAG CAA TCA GAC ACT CAA TAT GTC TGC AAA AGA ACG TTA GTG GAC
GAA GCC TAC CTT GAC AAG CAA TCC GAC ACT CAA TAT GTC TGC AAA CGT ACG CTG GTG GAC
 E   A   Y   L   D   K   Q   S   D   T   Q   Y   V   C   K   R   T   L   V   D

301/101                                      331/111
AGA GGC TGG GGA AAT GGA TGT GGA CTT TTT GGC AAA GGG AGC CTG GTG ACA TGC GCT AAG
CGT GGC TGG GGC AAT GGT TGT GGC CTT TTT GGT AAA GGG AGC CTG GTG ACC TGC GCT AAG
 R   G   W   G   N   G   C   G   L   F   G   K   G   S   L   V   T   C   A   K

361/121                                      391/131
TTT GCA TGC TCC AAG AAA ATG ACC GGG AAG AGC ATC CAG CCA GAG AAT CTG GAG TAC CGG
TTT GCA TGC TCC AAG AAA ATG ACC GGC AAG AGC ATC CAG CCA GAG AAT CTG GAG TAC CGC
 F   A   C   S   K   K   M   T   G   K   S   I   Q   P   E   N   L   E   Y   R

421/141                                      451/151
ATA ATG CTG TCA GTT CAT GGC TCC CAG CAC AGT GGG ATG ATC GTT AAT GAC ACA GGA CAT
ATC ATG CTG TCA GTT CAT GGC TCC CAG CAC AGT GGG ATG ATC GTT CAG GAC ACA GGT CAT
 I   M   L   S   V   H   G   S   Q   H   S   G   M   I   V   N   D   T   G   H
                                                                 Q*
481/161                                      511/171
GAA ACT GAT GAG AAT AGA GCG AAA GTT GAG ATA ACG CCC AAT TCA CCG AGA GCC GAA GCC
GAA ACT GAT GAG AAT CGC GCG AAA GTT GAG ATC ACG CCC AAT TCA CCG CGT GCC GAA GCC
 E   T   D   E   N   R   A   K   V   E   I   T   P   N   S   P   R   A   E   A

541/181                                      571/191
ACC CTG GGG GGT TTT GGA AGC CTA GGA CTT GAT TGT GAA CCG AGG ACA GGC CTT GAC TTT
ACC CTG GGG GGT TTT GGT AGC CTA GGT CTT GAT TGT GAA CCG CGT ACA GGC CTT GAC TTT
 T   L   G   G   F   G   S   L   G   L   D   C   E   P   R   T   G   L   D   F
```

FIGURE 5

```
601/201                                          631/211
TCA GAT TTG TAT TAC TTG ACT ATG AAT AAC AAG CAC TGG TTG GTT CAC AAG GAG TGG TTC
TCA GAT TTG TAT TAC TTG ACT ATG AAT AAC AAG CAC TGG TTG GTT CAC AAG GAG TGG TTC
 S   D   L   Y   Y   L   T   M   N   N   K   H   W   L   V   H   K   E   W   F

661/221                                          691/231
CAC GAC ATT CCA TTA CCT TGG CAC GCT GGG GCA GAC ACC GGA ACT CCA CAC TGG AAC AAC
CAC GAC ATT CCA TTA CCT TGG CAC GCT GGG GCA GAC ACC GGᵀ ACT CCA CAC TGG AAC AAC
 H   D   I   P   L   P   W   H   A   G   A   D   T   G   T   P   H   W   N   N

721/241                                          751/251
AAA GAA GCA CTG GTA GAG TTC AAG GAC GCA CAT GCC AAA AGG CAA ACT GTC GTG GTT CTA
AAA GAA GCA CTG GTA GAG TTC AAG GAC GCA CAT GCC AAA ᶜGᵀ CAA ACT GTC GTG GTT CTᶜ
 K   E   A   L   V   E   F   K   D   A   H   A   K   R   Q   T   V   V   V   L

781/261                                          811/271
GGG AGT CAA GAA GGA GCA GTT CAC ACG GCC CTT GCT GGA GCT CTG GAG GCT GAG ATG GAT
GGG AGT CAA GAA GGT GCA GTT CAC ACG GCC CTT GCT GGᵀ GCT CTG GAG GCT GAG ATG GAT
 G   S   Q   E   G   A   V   H   T   A   L   A   G   A   L   E   A   E   M   D

841/281                                          871/291
GGT GCA AAG GGA AGG CTG TCC TCT GGC CAC TTG AAA TGT CGC CTG AAA ATG GAT AAA CTT
GGT GCA AAG GGᶜ ᶜGᶜ CTG TCC TCT GGC CAC TTG AAA TGT CGC CTG AAA ATG GAT AAA CTT
 G   A   K   G   R   L   S   S   G   H   L   K   C   R   L   K   M   D   K   L

901/301                                          931/311
AGA TTG AAG GGC GTG TCA TAC TCC TTG TGT ACT GCA GCG TTC ACA TTC ACC AAG ATC CCG
ᶜGᵀ TTG AAG GGᵀ GTG TCA TAC TCC TTG TGT ACT GCA GCG TTC ACA TTC ACC AAG ATC CCG
 R   L   K   G   V   S   Y   S   L   C   T   A   A   F   T   F   T   K   I   P

961/321                                          991/331
GCT GAA ACA CTG CAC GGG ACA GTC ACA GTG GAG TTA CAG TAC GCA GGG ACA GAT GGA CCT
GCT GAA ACA CTG CAC GGG ACA GTC ACA GTG GAG TTA CAG TAC GCA GGG ACA GAT GGᵀ CCT
 A   E   T   L   H   G   T   V   T   V   E   L   Q   Y   A   G   T   D   G   P

1021/341                                         1051/351
TGC AAG GTT CCA GCT CAG ATG GCG GTG GAC ATG CAA ACT CTG ACC CCA GTT GGG AGG TTG
TGC AAG GTT CCA GCT CAG ATG GCG GTG GAC ATG CAA ACT CTG ACC CCA GTT GGG ᶜGᵀ TTG
 C   K   V   P   A   Q   M   A   V   D   M   Q   T   L   T   P   V   G   R   L

1081/361                                         1111/371
ATA ACC GCT AAC CCC GTA ATC ACT GAA AGC ACT GAG AAC TCT AAG ATG ATG CTG GAA CTT
ATᶜ ACC GCT AAC CCG GTA ATC ACT GAA AGC ACT GAG AAC TCT AAG ATG ATG CTG GAA CTT
 I   T   A   N   P   V   I   T   E   S   T   E   N   S   K   M   M   L   E   L

1141/381                                         1171/391
GAT CCA CCA TTT GGG GAC TCT TAC ATT GTC ATA GGA GTC GGG GAG AAG AAG ATC ACC CAC
GAT CCA CCA TTT GGG GAC TCT TAC ATT GTC ATᶜ GGᵀ GTC GGG GAG AAG AAG ATC ACC CAC
 D   P   P   F   G   D   S   Y   I   V   I   G   V   G   E   K   K   I   T   H

1201/401                                         1231/411
CAC TGG CAC AGG AGT GGC AGC ACC ATT GGA AAA GCA TTT GAA GCC ACT GTG AGA GGT GCC
CAC TGG CAC ᶜGᶜ AGT GGC AGC ACC ATT GGᵀ AAA GCA TTT GAA GCC ACT GTG ᶜGᵀ GGT GCC
 H   W   H   R   S   G   S   T   I   G   K   A   F   E   A   T   V   R   G   A
```

FIGURE 5 (continued)

```
1261/421                                    1291/431
AAG AGA ATG GCA GTC TTG GGA GAC ACA GCC TGG GAC TTT GGA TCA GTT GGA GGC GCT CTC
AAG CGT ATG GCA GTC TTG GGT GAC ACA GCC TGG GAC TTT GGT TCA GTT GGC GGC GCT CTC
 K   R   M   A   V   L   G   D   T   A   W   D   F   G   S   V   G   G   A   L

1321/441                                    1351/451
AAC TCA TTG GGC AAG GGC ATC CAT CAA ATT TTT GGA GCA GCT TTC AAA TCA TTG TTT GGA
AAC TCA TTG GGC AAG GGC ATC CAT CAA ATT TTT GGC GCA GCT TTC AAA TCA TTG TTT GGT
 N   S   L   G   K   G   I   H   Q   I   F   G   A   A   F   K   S   L   F   G

1381/461                                    1411/471
GGA ATG TCC TGG TTC TCA CAA ATT CTC ATT GGA ACG TTG CTG ATG TGG TTG GGT CTG AAC
GGT ATG TCC TGG TTC TCA CAA ATT CTC ATT GGA ACG TTG CTG ATG TGG TTG GGT CTG AAC
 G   M   S   W   F   S   Q   I   L   I   G   T   L   L   M   W   L   G   L   N

1441/481                                    1471/491
ACA AAG AAT GGA TCT ATT TCC CTT ATG TGC TTG GCC TTA GGG GGA GTG TTG ATC TTC TTA
ACA AAG GAG GGC TCT ATT TCC CTT ATG TGC TTG GCC TTA GGG GGT GTG TTG ATC TTC TTA
 T   K   N   G   S   I   S   L   M   C   L   A   L   G   G   V   L   I   F   L
         R*  (SEQ ID NO: 10)
1501/501
TCC ACA GCC GTC TCT GCT (SEQ ID NO: 7)
TCC ACA GCC GTC TCT GCT (SEQ ID NO: 8)
 S   T   A   V   S   A  (SEQ ID NO: 9)
```

FIGURE 5 (continued)

NS5 2718 bp (906 aa) in codon optimized and 2709 bp (903 aa) in original
137 aa (196 bp) codon optimized with 3 N-terminl codons added

```
1/1                                         31/11
                GGG GGT GGA ACA GGA GAG ACC CTG GGA GAG AAA TGG AAG GCC CGC TTG AAC
ATG AAA AAG GGT GGT GGT ACC GGT GAG ACC CTG GGT GAG AAA TGG AAG GCC CGC CTG AAC
 M   K   K   G   G   G   T   G   E   T   L   G   E   K   W   K   A   R   L   N

61/21                                       91/31
CAG ATG TCG GCC CTG GAG TTC TAC TCC TAC AAA AAG TCA GGC ATC ACC GAG GTG TGC AGA
CAG ATG TCG GCC CTG GAG TTC TAC TCC TAC AAA AAG TCC GGT ATC ACC GAG GTG TGC CGT
 Q   M   S   A   L   E   F   Y   S   Y   K   K   S   G   I   T   E   V   C   R

121/41                                      151/51
GAA GAG GCC CGC CGC GCC CTC AAG GAC GGT GTG GCA ACG GGA GGC CAT GCT GTG TCC CGA
GAA GAG GCC CGC CGC GCC CTG AAG GAC GGT GTG GCA ACG GGT GGT CAT GCT GTG TCC CGT
 E   E   A   R   R   A   L   K   D   G   V   A   T   G   G   H   A   V   S   R

181/61                                      211/71
GGA AGT GCA AAG CTG AGA TGG TTG GTG GAG CGG GGA TAC CTG CAG CCC TAT GGA AAG GTC
GGT AGC GCA AAG CTG CGT TGG CTG GTG GAG CGG GGT TAC CTG CAG CCA TAT GGT AAG GTC
 G   S   A   K   L   R   W   L   V   E   R   G   Y   L   Q   P   Y   G   K   V
```

FIGURE 6

```
241/81                                        271/91
ATT GAT CTT GGA TGT GGC AGA GGG GGC TGG AGT TAC TAC GTC GCC ACC ATC CGC AAA GTT
ATT GAT CTT GGT TGT GGC CGT GGC GGC TGG AGC TAC TAC GTC GCC ACC ATC CGC AAA GTT
 I   D   L   G   C   G   R   G   G   W   S   Y   Y   V   A   T   I   R   K   V

301/101                                       331/111
CAA GAA GTG AAA GGA TAC ACA AAA GGA GGC CCT GGT CAT GAA GAA CCC GTG TTG GTG CAA
CAA GAA GTG AAA GGT TAC ACC AAA GGT GGC CCT GGT CAT GAA GAA CCA GTG CTG GTG CAA
 Q   E   V   K   G   Y   T   K   G   G   P   G   H   E   E   P   V   L   V   Q

361/121                                       391/131
AGC TAT GGG TGG AAC ATA GTC CGT CTT AAG AGT GGG GTG GAC GTC TTT CAT ATG GCG GCT
AGC TAT GGC TGG AAC ATT GTC CGT CTG AAG AGC GGC GTG GAC GTC TTT CAT ATG GCG GCT
 S   Y   G   W   N   I   V   R   L   K   S   G   V   D   V   F   H   M   A   A

421/141                                       451/151
GAG CCG TGT GAC ACG TTG CTG TGT GAC ATA GGT GAG TCA TCA TCT AGT CCT GAA GTG GAA
GAG CCG TGT GAC ACG CTG CTG TGT GAC ATT GGT GAG TCC TCC TCT AGT CCA GAA GTG GAA
 E   P   C   D   T   L   L   C   D   I   G   E   S   S   S   S   P   E   V   E

481/161                                       511/171
GAA GCA CGG ACG CTC AGA GTC CTC TCC ATG GTG GGG GAT TGG CTT GAA AAA AGA CCA GGA
GAA GCA CGT ACG CTC CGT GTC CTG TCC ATG GTG GGT GAT TGG CTG GAA AAA CGT CCA GGT
 E   A   R   T   L   R   V   L   S   M   V   G   D   W   L   E   K   R   P   G

541/181                                       571/191
GCC TTT TGT ATA AAA GTG TTG TGC CCA TAC ACC AGC ACT ATG ATG GAA ACC CTG GAG CGA
GCC TTT TGT ATT AAA GTG CTG TGC CCA TAC ACC AGC ACT ATG ATG GAA ACC CTG GAG CGT
 A   F   C   I   K   V   L   C   P   Y   T   S   T   M   M   E   T   L   E   R

601/201                                       631/211
CTG CAG CGT AGG TAT GGG GGA GGA CTG GTC AGA GTG CCA CTC TCC CGC AAC TCT ACA CAT
CTG CAG CGT CGT TAT GGG GGT GGT CTG GTC CGT GTG CCA CTC TCC CGC AAC TCT ACA CAT
 L   Q   R   R   Y   G   G   G   L   V   R   V   P   L   S   R   N   S   T   H

661/221                                       691/231
GAG ATG TAC TGG GTC TCT GGA GCG AAA AGC AAC ACC ATA AAA AGT GTG TCC ACC ACG AGC
GAG ATG TAC TGG GTC TCT GGT GCG AAA AGC AAC ACC ATT AAA AGT GTG TCC ACC ACG AGC
 E   M   Y   W   V   S   G   A   K   S   N   T   I   K   S   V   S   T   T   S

721/241                                       751/251
CAG CTC CTC TTG GGG CGC ATG GAC GGG CCT AGG AGG CCA GTG AAA TAT GAG GAG GAT GTG
CAG CTC CTC TTG GGG CGC ATG GAC GGG CCT CGT CGT CCA GTG AAA TAT GAG GAG GAT GTG
 Q   L   L   L   G   R   M   D   G   P   R   R   P   V   K   Y   E   E   D   V

781/261                                       811/271
AAT CTC GGC TCT GGC ACG CGG GCT GTG GTA AGC TGC GCT GAA GCT CCC AAC ATG AAG ATC
AAT CTC GGT TCT GGT ACG CGT GCT GTG GTA AGC TGC GCT GAA GCT CCA AAC ATG AAG ATC
 N   L   G   S   G   T   R   A   V   V   S   C   A   E   A   P   N   M   K   I

841/281                                       871/291
ATT GGT AAC CGC ATT GAA AGG ATC CGC AGT GAG CAC GCG GAA ACG TGG TTC TTT GAC GAG
ATT GGT AAC CGC ATT GAA CGT ATC CGC AGT GAG CAC GCG GAA ACG TGG TTC TTT GAC GAG
 I   G   N   R   I   E   R   I   R   S   E   H   A   E   T   W   F   F   D   E
```

FIGURE 6 (continued)

```
901/301                                              931/311
AAC CAC CCA TAT AGG ACA TGG GCT TAC CAT    GGA AGC TAT GAG GCC CCC ACA CAA GGG TCA
AAC CAC CCA TAT CGT ACA TGG GCT TAC CAT    GGT AGC TAT GAG GCC CCA ACA CAA GGG TCA
 N   H   P   Y   R   T   W   A   Y   H      G   S   Y   E   A   P   T   Q   G   S

961/321                                              991/331
GCG TCC TCT CTA ATA AAC GGG GTT GTC AGG    CTC CTG TCA AAA CCC TGG GAT GTG GTG ACT
GCG TCC TCT CTG ATT AAC GGG GTT GTC CGT    CTC CTG TCA AAA CCA TGG GAT GTG GTG ACT
 A   S   S   L   I   N   G   V   V   R      L   L   S   K   P   W   D   V   V   T

1021/341                                             1051/351
GGA GTC ACA GGA ATA GCC ATG ACC GAC ACC    ACA CCG TAT GGT CAG CAA AGA GTT TTC AAG
GGT GTC ACA GGT ATT GCC ATG ACC GAC ACC    ACA CCG TAT GGT CAG CAA CGT GTT TTC AAG
 G   V   T   G   I   A   M   T   D   T      T   P   Y   G   Q   Q   R   V   F   K

1081/361                                             1111/371
GAA AAA GTG GAC ACT AGG GTG CCA GAC CCC    CAA GAA GGC ACT CGT CAG GTT ATG AGC ATG
GAA AAA GTG GAC ACT CGT GTG CCA GAC CCA    CAA GAA GGC ACT CGT CAG GTT ATG AGC ATG
 E   K   V   D   T   R   V   P   D   P      Q   E   G   T   R   Q   V   M   S   M

1141/381                                             1171/391
GTC TCT TCC TGG TTG TGG AAA GAG CTA GGC    AAA CAC AAA CGG CCA CGA GTC TGC ACC AAA
GTC TCT TCC TGG TTG TGG AAA GAG CTG GGC    AAA CAC AAA CGT CCA CGT GTC TGC ACC AAA
 V   S   S   W   L   W   K   E   L   G      K   H   K   R   P   R   V   C   T   K

1201/401                                             1231/411
GAA GAG TTC ATC AAC AAG GTT CGT AGC AAT    GCA GCA TTA GGG GCA ATA TTT GAA GAG GAA
GAA GAG TTC ATC AAC AAG GTT CGT AGC AAT    GCA GCA TTA GGG GCA ATT TTT GAA GAG GAA
 E   E   F   I   N   K   V   R   S   N      A   A   L   G   A   I   F   E   E   E

1261/421                                             1291/431
AAA GAG TGG AAG ACT GCA GTG GAA GCT GTG    AAC GAT CCA AGG TTC TGG GCT CTA GTG GAC
AAA GAG TGG AAG ACT GCA GTG GAA GCT GTG    AAC GAT CCA CGT TTC TGG GCT CTG GTG GAC
 K   E   W   K   T   A   V   E   A   V      N   D   P   R   F   W   A   L   V   D

1321/441                                             1351/451
AAG GAA AGA GAG CAC CAC CTG AGA GGA GAG    TGC CAG AGC TGT GTG TAC AAC ATG ATG GGA
AAG GAA CGT GAG CAC CAC CTG CGT GGT GAG    TGC CAG AGC TGT GTG TAC AAC ATG ATG GGT
 K   E   R   E   H   H   L   R   G   E      C   Q   S   C   V   Y   N   M   M   G

1381/461                                             1411/471
AAA AGA GAA AAG AAA CAA GGG GAA TTT GGA    AAG GCC AAG GGC AGC CGC GCC ATC TGG TAT
AAA CGT GAA AAG AAA CAA GGG GAA TTT GGT    AAG GCC AAG GGC AGC CGC GCC ATC TGG TAT
 K   R   E   K   K   Q   G   E   F   G      K   A   K   G   S   R   A   I   W   Y

1441/481                                             1471/491
ATG TGG CTA GGG GCT AGA TTT CTA GAG TTC    GAA GCC CTT GGA TTC TTG AAC GAG GAT CAC
ATG TGG CTG GGG GCT CGT TTT CTG GAG TTC    GAA GCC CTT GGT TTC TTG AAC GAG GAT CAC
 M   W   L   G   A   R   F   L   E   F      E   A   L   G   F   L   N   E   D   H

1501/501                                             1531/511
TGG ATG GGG AGA GAG AAC TCA GGA GGT GGT    GTT GAA GGG CTG GGA TTA CAA AGA CTC GGA
TGG ATG GGG CTG GAG AAC TCA GGT GGT GGT    GTT GAA GGG CTG GGT TTA CAA CGT CTC GGT
 W   M   G   R   E   N   S   G   G   G      V   E   G   L   G   L   Q   R   L   G
```

FIGURE 6 (continued)

```
1561/521                                          1591/531
TAT GTC CTA GAA GAG ATG AGT CGT ATA CCA GGA GGA AGG ATG TAT GCA GAT GAC ACT GCT
TAT GTC CTG GAA GAG ATG AGT CGT ATT CCA GGT GGT CGT ATG TAT GCA GAT GAC ACT GCT
 Y   V   L   E   E   M   S   R   I   P   G   G   R   M   Y   A   D   D   T   A

1621/541                                          1651/551
GGC TGG GAC ACC CGC ATT AGC AGG TTT GAT CTG GAG AAT GAA GCT CTA ATC ACC AAC CAA
GGC TGG GAC ACC CGC ATT AGC CGT TTT GAT CTG GAG AAT GAA GCT CTG ATC ACC AAC CAA
 G   W   D   T   R   I   S   R   F   D   L   E   N   E   A   L   I   T   N   Q

1681/561                                          1711/571
ATG GAG AAA GGG CAC AGG GCC TTG GCA TTG GCC ATA ATC AAG TAC ACA TAC CAA AAC AAA
ATG GAG AAA GGG CAC CTG GCC TTG GCA TTG GCC ATT ATC AAG TAC ACA TAC CAA AAC AAA
 M   E   K   G   H   R   A   L   A   L   A   I   I   K   Y   T   Y   Q   N   K

1741/581                                          1771/591
GTG GTA AAG GTC CTT AGA CCA GCT GAA AAA GGG AAA ACA GTT ATG GAC ATT ATT TCG AGA
GTG GTA AAG GTC CTT CGT CCA GCT GAA AAA GGG AAA ACA GTT ATG GAC ATT ATT TCG CGT
 V   V   K   V   L   R   P   A   E   K   G   K   T   V   M   D   I   I   S   R

1801/601                                          1831/611
CAA GAC CAA AGG GGG AGC GGA CAA GTT GTC ACT TAC GCT CTT AAC ACA TTT ACC AAC CTA
CAA GAC CAA CGT GGG AGC GGT CAA GTT GTC ACT TAC GCT CTT AAC ACA TTT ACC AAC CTG
 Q   D   Q   R   G   S   G   Q   V   V   T   Y   A   L   N   T   F   T   N   L

1861/621                                          1891/631
GTG GTG CAA CTC ATT CGG AAT ATG GAG GCT GAG GAA GTT CTA GAG ATG CAA GAC TTG TGG
GTG GTG CAA CTC ATT CGT AAT ATG GAG GCT GAG GAA GTT CTG GAG ATG CAA GAC TTG TGG
 V   V   Q   L   I   R   N   M   E   A   E   E   V   L   E   M   Q   D   L   W

1921/641                                          1951/651
CTG CTG CGG AGG TCA GAG AAA GTG ACC AAC TGG TTG CAG AGC AAC GGA TGG GAT AGG CTC
CTG CTG CGT CGT TCA GAG AAA GTG ACC AAC TGG TTG CAG AGC AAC GGT TGG GAT CGT CTC
 L   L   R   R   S   E   K   V   T   N   W   L   Q   S   N   G   W   D   R   L

1981/661                                          2011/671
AAA CGA ATG GCA GTC AGT GGA GAT GAT TGC GTT GTG AAG CCA ATT GAT GAT AGG TTT GCA
AAA CGT ATG GCA GTC AGT GGT GAT GAT TGC GTT GTG AAG CCA ATT GAT GAT CGT TTT GCA
 K   R   M   A   V   S   G   D   D   C   V   V   K   P   I   D   D   R   F   A

2041/681                                          2071/691
CAT GCC CTC AGG TTC TTG AAT GAT ATG GGA AAA GTT AGG AAG GAC ACA CAA GAG TGG AAA
CAT GCC CTC CGT TTC TTG AAT GAT ATG GGT AAA GTT CGT AAG GAC ACA CAA GAG TGG AAA
 H   A   L   R   F   L   N   D   M   G   K   V   R   K   D   T   Q   E   W   K

2101/701                                          2131/711
CCC TCA ACT GGA TGG GAC AAC TGG GAA GAA GTT CCG TTT TGC TCC CAC CAC TTC AAC AAG
CCA TCA ACT GGT TGG GAC AAC TGG GAA GAA GTT CCG TTT TGC TCC CAC CAC TTC AAC AAG
 P   S   T   G   W   D   N   W   E   E   V   P   F   C   S   H   H   F   N   K

2161/721                                          2191/731
CTC CAT CTC AAG GAC GGG AGG TCC ATT GTG GTT CCC TGC CGC CAC CAA GAT GAA CTG ATT
CTC CAT CTC AAG GAC GGG CGT TCC ATT GTG GTT CCA TGC CGC CAC CAA GAT GAA CTG ATT
 L   H   L   K   D   G   R   S   I   V   V   P   C   R   H   Q   D   E   L   I
```

FIGURE 6 (continued)

```
2221/741                                          2251/751
GGC CGG GCC CGC GTC TCT CCA GGG GCG GGA           TGG AGC ATC CGG GAG ACT GCT TGC CTA GCA
GGC CGT GCC CGC GTC TCT CCA GGG GCG GGT           TGG AGC ATC CGT GAG ACT GCT TGC CTG GCA
 G   R   A   R   V   S   P   G   A   G             W   S   I   R   E   T   A   C   L   A

2281/761                                          2311/771
AAA TCA TAT GCG CAA ATG TGG CAG CTC CTT           TAT TTC CAC AGA AGG GAC CTC CGA CTG ATG
AAA TCA TAT GCG CAA ATG TGG CAG CTC CTT           TAT TTC CAC CGT CGT GAC CTC CGT CTG ATG
 K   S   Y   A   Q   M   W   Q   L   L             Y   F   H   R   R   D   L   R   L   M

2341/781                                          2371/791
GCC AAT GCC ATT TGT TCA TCT GTG CCA GTT           GAC TGG GTT CCA ACT GGG AGA ACT ACC TGG
GCC AAT GCC ATT TGT TCA TCT GTG CCA GTT           GAC TGG GTT CCA ACT GGG CGT ACT ACC TGG
 A   N   A   I   C   S   S   V   P   V             D   W   V   P   T   G   R   T   T   W

2401/801                                          2431/811
TCA ATC CAT GGA AAG GGA GAA TGG ATG ACC           ACT GAA GAC ATG CTT GTG GTG TGG AAC AGA
TCA ATC CAT GGT AAG GGT GAA TGG ATG ACC           ACT GAA GAC ATG CTT GTG GTG TGG AAC CGT
 S   I   H   G   K   G   E   W   M   T             T   E   D   M   L   V   V   W   N   R

2461/821                                          2491/831
GTG TGG ATT GAG GAG AAC GAC CAC ATG GAA           GAC AAG ACC CCA GTT ACG AAA TGG ACA GAC
GTG TGG ATT GAG GAG AAC GAC CAC ATG GAA           GAC AAG ACC CCA GTT ACG AAA TGG ACA GAC
 V   W   I   E   E   N   D   H   M   E             D   K   T   P   V   T   K   W   T   D

2521/841                                          2551/851
ATT CCC TAT TTG GGA AAA AGG GAA GAC TTG           TGG TGT GGA TCT CTC ATA GGG CAC AGA CCG
ATT CCA TAT TTG GGT AAA CGT GAA GAC TTG           TGG TGT GGT TCT CTC ATT GGG CAC CGT CCG
 I   P   Y   L   G   K   R   E   D   L             W   C   G   S   L   I   G   H   R   P

2581/861                                          2611/871
CGC ACC ACC TGG GCT GAG AAC ATT AAA AAC           ACA GTC AAC ATG GTG CGC AGG ATC ATA GGT
CGC ACC ACC TGG GCT GAG AAC ATT AAA AAC           ACA GTC AAC ATG GTG CGC CGT ATC ATT GGT
 R   T   T   W   A   E   N   I   K   N             T   V   N   M   V   R   R   I   I   G

2641/881                                          2671/891
GAT GAA GAA AAG TAC ATG GAC TAC CTA TCC           ACC CAA GTT CGC TAC TTG GGT GAA GAA GGG
GAT GAA GAA AAG TAC ATG GAC TAC CTG TCC           ACC CAA GTT CGC TAC TTG GGT GAA GAA GGG
 D   E   E   K   Y   M   D   Y   L   S             T   Q   V   R   Y   L   G   E   E   G
                                                                              (SEQ ID NO: 13)

2701/901
TCT ACA CCT GGA GTG CTG (SEQ ID NO: 11)
TCT ACA CCT GGT GTG CTG (SEQ ID NO: 12)
```

FIGURE 6 (continued)

GACTCTTCGCGATGTACGGGCCAGATATACGCGTTAACTGCAGTCTAGAT
TATGCGAAAGGCCATCCTGACGGATGGCCTTTTTGTTTAAACGGATCCGC
GACATTGATTATTGACTAGTTATTAATAGTAATCAATTACGGGGTCATTA
GgggactttccggggactttccTccccacgcgGgggactttccgccacgg
gcggggactttccggggactttccGTTCATAGCCCATATATGGAGTTCCG
CGTTACATAACTTACGGTAAATGGCCCGCCTGGCTGACCGCCCAACGACC
CCCGCCCATTGACGTCAATAATGACGTATGTTCCCATAGTAACGCCAATA
GGGACTTTCCATTGACGTCAATGGGTGGACTATTTACGGTAAACTGCCCA
CTTGGCAGTACATCAAGTGTATCATATGCCAAGTACGCCCCTATTGACG
TCAATGACGGTAAATGGCCCGCCTGGCATTATGCCCAGTACATGACCTTA
TGGGACTTTCCTACTTGGCAGTACATCTACGTATTAGTCATCGCTATTAC
CATGGTGATGCGGTTTTGGCAGTACATCAATGGGCGTGGATAGCGGTTTG
ACTCACGGGGATTTCCAAGTCTCCACCCCATTGACGTCAATGGGAGTTTG
TTTTGGCACCAAAATCAACGGGACTTTCCAAAATGTCGTAACAACTCCGC
CCCATTGACGCAAATGGGCGGTAGGCGTGTACGGTGGGAGGTCTATATAA
GCAGAGCTCTCTGGCTAACTAGAGAACCCACTGCTTACTGGCTTATCGAA
ATTAATACGACTCACTATAGGGAGACCCAAGCTGGCTAGCGTTTAAACTT
AAGCTTGGTACCGAGCTCGGATCCACTAGTCCAGTGTGGTGGAATTCTGC
AGATATCCAGCACAGTGGCGGCCGCTCGAGAATGCTTCGAGCAGACATGA
TAAGATACATTGATGAGTTTGGACAAACCACAACTAGAATGCAGTGAAAA
AAATGCTTTATTTGTGAAATTTGTGATGCTATTGCTTTATTTGTAACCAT
TATAAGCTGCAATAAACAAGTTAACAACAACAATTGCATTCATTTTATGT
TTCAGGTTCAGGGGGAGATGTGGGAGGTTTTTTAAAGCAAGTAAAACCTC
TACAAATGTGGTAAAATCCGATAAGGATCGATCCGGGGCATGCAACCAGC
TGTGGAATGTGTGTCAGTTAGGGTGTGGAAAGTCCCCAGGCTCCCCAGCA
GGCAGAAGTATGCAAAGCATGTGGGGATGCGGTGGGCTCTATGGCTTCTA
CTGGGCGGTTTTATGGACAGCAAGCGAACCGGAATTGCCAGCTGGGGCGC
CCTCTGGTAAGGTTGGGAAGCCCTGCAAAGTAAACTGGATGGCTTTCTCG
CCGCCAAGGATCTGTCGACCCCTAGATTTCAGTGCAATTTATCTCTTCAA
ATGTAGCACCTGAAGTCAGCCCCATACGATATAAGTTGTTGGAAGATCTA
GCCCGCCTAATGAGCGGGCTTTTTTTTAATTCGCAATTCCCCGATGCATA
ATGTGCCTGTCAAATGGACGAAGCAGGGATTCTGCAAACCCTATGCTACT
CCGTCAAGCCGTCAATTGTCTGATTCGTTACCAATTATGACAACTTGACG
GCTACATCATTCACTTTTTCTTCACAACCGGCACGAAACTCGCTCGGGCT
GGCCCCGGTGCATTTTTTAAATACTCGCGAGAAATAGAGTTGATCGTCAA
AACCAACATTGCGACCGACGGTGGCGATAGGCATCCGGGTAGTGCTCAAA
AGCAGCTTCGCCTGACTAATGCGTTGGTCCTCGCGCCAGCTTAAGACGCT
AATCCCTAACTGCTGGCGGAAAAGATGTGACAGACGCGACGGCGACAAGC
```

FIGURE 7

```
AAACATGCTGTGCGACGCTGGCGATATCAAAATTGCTGTCTGCCAGGTGA
TCGCTGATGTACTGACAAGCCTCGCGTACCCGATTATCCATCGGTGGATG
GAGCGACTCGTTAATCGCTTCCATGCGCCGCAGTAACAATTGCTCAAGCA
GATTTATCGCCAGCAGCTCCGAATAGCGCCCTTCCCCTTGCCCGGCGTTA
ATGATTTGCCCAAACAGGTCGCTGAAATGCGGCTGGTGCGCTTCATCCGG
GCGAAAGAAACCCGTATTGGCAAATATTGACGGCCAGTTAAGCCATTCAT
GCCAGTAGGCGCGCGGACGAAAGTAAACCCACTGGTGATACCATTCGCGA
GCCTCCGGATGACGACCGTAGTGATGAATCTCTCCTGGCGGGAACAGCAA
AATATCACCCGGTCGGCAGACAAATTCTCGTCCCTGATTTTTCACCACCC
CCTGACCGCGAATGGTGAGATTGAGAATATAACCTTTCATTCCCAGCGGT
CGGTCGATAAAAAATCGAGATAACCGTTGGCCTCAATCGGCGTTAAACC
CGCCACCAGATGGGCGTTAAACGAGTATCCCGGCAGCAGGGGATCATTTT
GCGCTTCAGCCATACTTTTCATACTCCCACCATTCAGAGAAGAAACCAAT
TGTCCATATTGCATCAGACATTGCCGTCACTGCGTCTTTTACTGGCTCTT
CTCGCTAACCCAACCGGTAACCCCGCTTATTAAAAGCATTCTGTAACAAA
GCGGGACCAAAGCCATGACAAAAACGCGTAACAAAAGTGTCTATAATCAC
GGCAGAAAGTCCACATTGATTATTTGCACGGCGTCACACTTTGCTATGC
CATAGCATTTTTATCCATAAGATTAGCGGATCCTACCTGACGCTTTTTAT
CGCAACTCTCTACTGTTTCTCCATACCCGTTTTTTTGGGCTAGCGAATTC
TGAGAACAAACTAAGTGGATAAATTTCGTGTTCAGGGGCCAACGAAGCTC
CAGGGCGAAGTCACAATTTCCGGCGCTAAAAATGCTGCTCTGCCTATCCT
TTTTGCCGCACTACTGGCGGAAGAACCGGTAGAGATCCAGAACGTCCCGA
AACTGAAAGACGTCGATACATCAATGAAGCTGCTAAGCCAGCTGGGTGCG
AAAGTAGAACGTAATGGTTCTGTGCATATTGATGCCCGCGACGTTAATGT
ATTCTGCGCACCTTACGATCTGGTTAAAACCATGCGTGCTTCTATCTGGG
CGCTGGGGCCGCTGGTAGCGCGCTTTGGTCAGGGGCAAGTTTCACTACCT
GGCGGTTGTACGATCGGTGCGCGTCCGGTTGATCTACACATTTCTGGCCT
CGAACAATTAGGCGCGACCATCAAACTGGAAGAAGGTTACGTTAAAGCTT
CCGTCGATGGTCGTTTGAAAGGTGCACATATCGTGATGGATAAAGTCAGC
GTTGGCGCAACGGTGACCATCATGTGTGCTGCAACCCTGGCGGAAGGCAC
CACGATTATTGAAAACGCAGCGCGTGAACCGGAAATCGTCGATACCGCGA
ACTTCCTGATTACGCTGGGTGCGAAAATTAGCGGTCAGGGCACCGATCGT
ATCGTCATCGAAGGTGTGGAACGTTTAGGCGGCGGTGTCTATCGCGTTCT
GCCGGATCGTATCGAAACCGGTACTTTCCTGGTGGCGGCGGCGATTTCTC
GCGGCAAAATTATCTGCCGTAACGCGCAGCCAGATACTCTCGACGCCGTG
CTGGCGAAACTGCGTGACGCTGGAGCGGACATCGAAGTCGGCGAAGACTG
GATTAGCCTGGATATGCATGGCAAACGTCCGAAGGCTGTTAACGTACGTA
CCGCGCCGCATCCGGCATTCCCGACCGATATGCAGGCCCAGTTCACGCTG
```

FIGURE 7 (continued)

```
TTGAACCTGGTGGCAGAAGGGACCGGGTTTATCACCGAAACGGTCTTTGA
AAACCGCTTTATGCATGTGCCAGAGCTGAGCCGTATGGGCGCGCACGCCG
AAATCGAAAGCAATACCGTTATTTGTCACGGTGTTGAAAACTTTCTGGC
GCACAGGTTATGGCAACCGATCTGCGTGCATCAGCAAGCCTGGTGCTGGC
TGGCTGTATTGCGGAAGGACGACGGTGGTTGATCGTATTTATCACATCG
ATCGTGGCTACGAACGCATTGAAGACAAACTGCGCGCTTTAGGTGCAAAT
ATTGAGCGTGTGAAAGGCAATAAGAATTCAGGAAAAAACGCTGTGAAA
AATGTTGGTTTTATCGGCTGGCGCGGAATGGTCGGCTCTGTTCTCATGCA
ACGCATGGTAGAGGAGCGCGATTTCGACGCTATTCGCCCTGTTTTCTTTT
CTACCTCCCAGTTTGGACAGGCGGCGCCCACCTTCGGCGACACCTCCACC
GGCACGCTACAGGACGCTTTTGATCTGGATGCGCTAAAAGCGCTCGATAT
CATCGTGACCTGCCAGGGCGGCGATTATACCAACGAAATTTATCCAAAGC
TGCGCGAAAGCGGATGGCAGGGTTACTGGATTGATGCGGCTTCTACGCTG
CGCATGAAAGATGATGCCATTATTATTCTCGACCCGGTCAACCAGGACGT
GATTACCGACGGCCTGAACAATGGCGTGAAGACCTTTGTGGGCGGTAACT
GTACCGTTAGCCTGATGTTGATGTCGCTGGGCGGTCTCTTTGCCCATAAT
CTCGTTGACTGGGTATCCGTCGCGACCTATCAGGCCGCCTCCGGCGGCGG
CGCGCGCCATATGCGCGAGCTGTTAACCCAGATGGGTCAGTTGTATGGCC
ATGTCGCCGATGAACTGGCGACGCCGTCTTCCGCAATTCTTGATATTGAA
CGCAAAGTTACGGCATTGACCCGCAGCGGCGAGCTGCCGGTTGATAACTT
TGGCGTACCGCTGGCGGGAAGCCTGATCCCCTGGATCGACAAACAGCTCG
ATAACGGCCAGAGCCGCGAAGAGTGGAAAGGCCAGGCGGAAACCAACAAG
ATTCTCAATACTGCCTCTGTGATTCCGGTTGATGGTTTGTGTGTGCGCGT
CGGCGCGCTGCGCTGTCACAGCCAGGCGTTCACCATCAAGCTGAAAAAAG
AGGTATCCATTCCGACGGTGGAAGAACTGCTGGCGGCACATAATCCGTGG
GCGAAAGTGGTGCCGAACGATCGTGATATCACTATGCGCGAATTAACCCC
GGCGGCGGTGACCGGCACGTTGACTACGCCGGTTGGTCGTCTGCGTAAGC
TGAACATGGGGCCAGAGTTCTTGTCGGCGTTTACCGTAGGCGACCAGTTG
TTATGGGGCGCCGCCGAGCCGCTGCGTCGAATGCTGCGCCAGTTGGCGTA
GTCTAGCTGCACGATACCGTCGACTTGTACATAGACTCGCTCCGAAATTA
AAGAACACTTAAATTATCTACTAAAGGAATCTTTAGTCAAGTTTATTTAA
GATGACTTAACTATGAATACACAATTGATGGGTGAGCGTAGGATCTTCCA
TTATTGAAGCATTTATCAGGGTTATTGTCTCATGAGCTTGGCTGTTTTGG
CGGATGAGAGAAGATTTTCAGCCTGATACAGATTAAATCAGAACGCAGAA
GCGGTCTGATAAACAGTTTGCCTGGCGGCAGTAGCGCGGTGGTCCCACC
TGACCCCATGCCGAACTCAGAAGTGAAACGCCGTAGCGCCGATGGTAGTG
TGGGGTCTCCCCATGCGAGAGTAGGGAACTGCCAGGCATCAAATAAAACG
```

FIGURE 7 (continued)

```
AAAGGCTCAGTCGAAAGACTGGGCCTTTCGTTTTATCTGTTGTTTGTCGG
TGAACGCTCTCCTGAGTAGGACAAATCCGCCGGGAGCGGATTTGAACGTT
GCGAAGCAACGGCCCGGAGGGTGGCGGGCAGGACGCCCGCCATAAACTGC
CAGGCATCAAATTAAGCAGAAGGCCATCCTGACGGATGGCCTTTTTGCGT
TTCTACAAACTCTTTTTGTTTATTTTTCTAAATACATTCAAATATGTATC
CGCTCATGAGACAATAACCCTGATAAATGCTTCAATAATGGAAGATCTTC
CAACATCACAGGTAAACAGAAACGTCGGGTCGATCGGGAAATTCTTTCCC
GGACGGCGCGGGGTTGGGCAAGCCGCAGGCGCGTCAGTGCTTTTAGCGGG
TGTCGGGGCAGCCCTGAACCAGTCACGGGATCGATCTGTGCGGTATTTCA
CACCGCATACAGGTGGCACTTTTCGGGGAAATGTGCGCGGAACCCCTATT
TGTTTATTTTTCTAAATACATTCAAATATGTATCCGCTCATGAGACAATA
ACCCTGATAAATGCTTCAATAATAGCACGTGCTAAAACTTCATTTTTAAT
TTAAAAGGATCTAGGTGAAGATCCTTTTTGATAATCTCATGACCAAAATC
CCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGC
AAACAAAAAAACCACCGCTACCAGCGGTGGTTTGTTTGCCGGATCAAGAG
CTACCAACTCTTTTTCCGAAGGTAACTGGCTTCAGCAGAGCGCAGATACC
AAATACTGTCCTTCTAGTGTAGCCGTAGTTAGGCCACCACTTCAAGAACT
CTGTAGCACCGCCTACATACCTCGCTCTGCTAATCCTGTTACCAGTGGCT
GCTGCCAGTGGCGATAAGTCGTGTCTTACCGGGTTGGACTCAAGACGATA
GTTACCGGATAAGGCGCAGCGGTCGGGCTGAACGGGGGGTTCGTGCACAC
AGCCCAGCTTGGAGCGAACGACCTACACCGAACTGAGATACCTACAGCGT
GAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGA
CTTGAGCGTCGATTTTTGTGATGCTCGTCAGGGGGCGGAGCCTATGGAA
AAACGCCAGCAACGCGGCCTTTTTACGGTTCCTGGGCTTTTGCTGGCCTT
TTGCTCACATGTTCT   (SEQ ID NO: 14)
```

FIGURE 7 (continued)

prM 288 bp (96 aa)
GC ori 48.0& codon op 52.1% best codon 51.0%
```
1/1                                                 31/11
ATG AAA AAG GCG GAG GTC ACT AGA CGT GGG AGT GCA TAC TAT ATG TAC TTG GAC AGA AAC
ATG AAA AAG GCG GAG GTC ACT CGT CGT GGT AGC GCA TAC TAT ATG TAC CTG GAC CGC AAC
ATG AAA AAA GCG GAA GTT ACC CGT CGT GGT TCT GCG TAC TAC ATG TAC CTG GAT CGC AAC
 M   K   K   A   E   V   T   R   R   G   S   A   Y   Y   M   Y   L   D   R   N 61/21                                               91/31
GAT GCT GGG GAG GCC ATA TCT TTT CCA ACC ACA TTG GGG ATG AAT AAG TGT TAT ATA CAG
GAT GCT GGC GAG GCC ATC TCT TTT CCA ACC ACC TTG GGT ATG AAT AAG TGT TAT ATC CAG
GAT GCG GGT GAA GCG ATC TCT TTC CCG ACC ACC CTG GGT ATG AAC AAA TGC TAC ATC CAG
 D   A   G   E   A   I   S   F   P   T   T   L   G   M   N   K   C   Y   I   Q 121/41                                              151/51
ATC ATG GAT CTT GGA CAC ATG TGT GAT GCC ACC ATG AGC TAT GAA TGC CCT ATG CTG GAT
ATC ATG GAT CTG GGC CAC ATG TGT GAT GCC ACC ATG AGC TAT GAA TGC CCT ATG CTG GAT
ATC ATG GAT CTG GGT CAC ATG TGC GAT GCC ACC ATG TCT TAC GAA TGC CCG ATG CTG GAT
 I   M   D   L   G   H   M   C   D   A   T   M   S   Y   E   C   P   M   L   D 181/61                                              211/71
GAG GGG GTG GAA CCA GAT GAC GTC GAT TGT TGG TGC AAC ACG ACG TCA ACT TGG GTT GTG
GAG GGG GTG GAA CCA GAT GAC GTC GAT TGT TGG TGC AAC ACG ACG TCA ACT TGG GTT GTG
GAA GGT GTT GAA CCG GAT GAT GTT GAT TGC TGG TGC AAC ACC ACC TCT ACT TGG GTT GTT
 E   G   V   E   P   D   D   V   D   C   W   C   N   T   T   S   T   W   V   V 241/81                                              271/91
TAC GGA ACC TGC CAT CAC AAA AAA GGT GAA GCA CGG AGA TCT AGA AGA    (SEQ ID NO: 15)
TAC GGT ACC TGC CAT CAC AAA AAA GGT GAA GCA CGC CGC TCT CGC CGC   (SEQ ID NO: 16)
TAC GGT ACC TGC CAC CAC AAA AAA GGT GAA GCG CGT CGT TCT CGT CGT   (SEQ ID NO: 17)
 Y   G   T   C   H   H   K   K   G   E   A   R   R   S   R   R   (SEQ ID NO: 18)
```

FIGURE 10A

E protein (M) 1518 bp (506 aa)
GC ori 49.6% codon opt 52.1%  best codon 52.0%

```
1/1                                           31/11
ATG AAA ATC AGG TGC ATA GGA GTC AGC AAT AGG GAC TTT GTG AAA GGT ATG TCA GGT GGG
ATG AAA ATC CGC TGC ATC GGT GTC AGC AAT CGT GAC TTT GTG AAA GGT ATG TCC GGT GGT
ATG AAA ATC CGC TGC ATC GGT GTT TCT AAC CGT GAC TTC GTT GAA GGT ATG TCT GGT GGT
 M   K   I   R   C   I   G   V   S   N   R   D   F   V   E   G   M   S   G   G

61/21                                         91/31
ACT TGG GTT GAT GTT GTC TTG GAA CAT GGA GGT TGT GTC ACC GTA ATG GCA CAG GAC AAA
ACT TGG GTT GAT GTT GTC CTG GAA CAT GGC GGT TGT GTC ACC GTA ATG GCA CAG GAC AAA
ACC TGG GTT GAT GTT GTT CTG GAA CAC GGT GGT TGC GTT ACC GTT ATG GCG CAG GAT AAA
 T   W   V   D   V   V   L   E   H   G   G   C   V   T   V   M   A   Q   D   K

121/41                                        151/51
CCG ACT GTC GAC ATA GAG CTG GTT ACA ACA ACA GTC AGC AAC ATG GCG GAG GTA AGA TCC
CCG ACT GTC GAC ATC GAG CTG GTT ACC ACC ACC GTC AGC AAC ATG GCG GAG GTA CGT TCC
CCG ACC GTT GAT ATC GAA CTG GTT ACC ACC ACC GTT TCT AAC ATG GCG GAA GTT CGT TCT
 P   T   V   D   I   E   L   V   T   T   T   V   S   N   M   A   E   V   R   S

181/61                                        211/71
TAC TGC TAT GAG GCA TCA ATA TCA GAC ATG GCT TCT GAC AGC CGC TGC CCA ACA CAA GGT
TAC TGC TAT GAG GCA TCC ATC TCC GAC ATG GCT TCT GAC AGC CGC TGC CCA ACC CAA GGT
TAC TGC TAC GAA GCG TCT ATC TCT GAT ATG GCG TCT GAT AGC CGT TGC CCG ACC CAG GGT
 Y   C   Y   E   A   S   I   S   D   M   A   S   D   S   R   C   P   T   Q   G

241/81                                        271/91
GAA GCC TAC CTT GAC AAG CAA TCA GAC ACT CAA TAT GTC TGC AAA AGA ACG TTA GTG GAC
GAA GCC TAC CTT GAC AAG CAA TCC GAC ACT CAA TAT GTC TGC AAA CGT ACG CTG GTG GAC
GAA GCG TAC CTG GAT AAA CAG TCT GAT ACC CAG TAC GTT TGC AAA CGT ACC CTG GTT GAT
 E   A   Y   L   D   K   Q   S   D   T   Q   Y   V   C   K   R   T   L   V   D

301/101                                       331/111
AGA GGC TGG GGA AAT GGA TGT GGA CTT TTT GGC AAA GGG AGC CTG GTG ACA TGC GCT AAG
CGT GGC TGG GGC AAT GGT TGT GGC CTT TTT GGT AAA GGG AGC CTG GTG ACC TGC GCT AAG
CGT GGT TGG GGC AAC GGT TGC GGT CTG TTC GGT AAA GGT TCT CTG GTT ACC TGC GCT AAA
 R   G   W   G   N   G   C   G   L   F   G   K   G   S   L   V   T   C   A   K

361/121                                       391/131
TTT GCA TGC TCC AAG AAA ATG ACC GGG AAG AGC ATC CAG CCA GAG AAT CTG GAG TAC CGG
TTT GCA TGC TCC AAG AAA ATG ACC GGC AAG AGC ATC CAG CCA GAG AAT CTG GAG TAC CGC
TTC GCA TGC TCT AAA AAA ATG ACC GGT AAA AGC ATC CAG CCG GAA AAC CTG GAA TAC CGT
 F   A   C   S   K   K   M   T   G   K   S   I   Q   P   E   N   L   E   Y   R
```

FIGURE 10B

```
421/141                                             451/151
ATA ATG CTG TCA GTT CAT GGC TCC CAG CAC AGT GGG ATG ATC GTT AAT GAC ACA GGA CAT
ATC ATG CTG TCA GTT CAT GGC TCC CAG CAC AGT GGG ATG ATC GTT CAG GAC ACA GGT CAT
ATC ATG CTG TCT GTT CAC GGC TCC CAG CAC TCT GGT ATG ATC GTT AAC GAT ACC GGT CAC
 I   M   L   S   V   H   G   S   Q   H   S   G   M   I   V   N   D   T   G   H
                                                                    Q*
481/161                                             511/171
GAA ACT GAT GAG AAT AGA GCG AAA GTT GAG ATA ACG CCC AAT TCA CCG AGA GCC GAA GCC
GAA ACT GAT GAG AAT CGC GCG AAA GTT GAG ATC ACG CCC AAT TCA CCG CGT GCC GAA GCC
GAA ACC GAT GAA AAC CGT GCG AAA GTT GAA ATC ACC CCG AAC TCT CCG CGT GCC GAA GCC
 E   T   D   E   N   R   A   K   V   E   I   T   P   N   S   P   R   A   E   A

541/181                                             571/191
ACC CTG GGG GGT TTT GGA AGC CTA GGA CTT GAT TGT GAA CCG AGG ACA GGC CTT GAC TTT
ACC CTG GGG GGT TTT GGT AGC CTA GGT CTT GAT TGT GAA CCG CGT ACA GGC CTT GAC TTT
ACC CTG GGT GGT TTC GGT TCT CTG GGT CTG GAT TGC GAA CCG CGT ACC GGT CTG GAT TTC
 T   L   G   G   F   G   S   L   G   L   D   C   E   P   R   T   G   L   D   F

601/201                                             631/211
TCA GAT TTG TAT TAC TTG ACT ATG AAT AAC AAG CAC TGG TTG GTT CAC AAG GAG TGG TTC
TCA GAT TTG TAT TAC TTG ACT ATG AAT AAC AAG CAC TGG TTG GTT CAC AAG GAG TGG TTC
TCT GAT CTG TAC TAC CTG ACC ATG AAC AAC AAG CAC TGG CTG GTT CAC AAG GAA TGG TTC
 S   D   L   Y   Y   L   T   M   N   N   K   H   W   L   V   H   K   E   W   F

661/221                                             691/231
CAC GAC ATT CCA TTA CCT TGG CAC GCT GGG GCA GAC ACC GGA ACT CCA CAC TGG AAC AAC
CAC GAC ATT CCA TTA CCT TGG CAC GCT GGG GCA GAC ACC GGT ACT CCA CAC TGG AAC AAC
CAC GAT ATC CCG CTG CCG TGG CAC GCT GGT GCA GAT ACC GGT ACC CCG CAC TGG AAC AAC
 H   D   I   P   L   P   W   H   A   G   A   D   T   G   T   P   H   W   N   N

721/241                                             751/251
AAA GAA GCA CTG GTA GAG TTC AAG GAC GCA CAT GCC AAA AGG CAA ACT GTC GTG GTT CTA
AAA GAA GCA CTG GTA GAG TTC AAG GAC GCA CAT GCC AAA CGT CAA ACT GTC GTG GTT CTG
AAA GAA GCA CTG GTT GAA TTC AAA GAT GCA CAC GCC AAA CGT CAG ACC GTT GTT GTT CTG
 K   E   A   L   V   E   F   K   D   A   H   A   K   R   Q   T   V   V   V   L

781/261                                             811/271
GGG AGT CAA GAA GGA GCA GTT CAC ACG GCC CTT GCT GGA GCT CTG GAG GCT GAG ATG GAT
GGG AGT CAA GAA GGT GCA GTT CAC ACG GCC CTT GCT GGT GCT CTG GAG GCT GAG ATG GAT
GGT TCT CAG GAA GGT GCA GTT CAC ACC GCC CTG GCT GGT GCT CTG GAA GCT GAA ATG GAT
 G   S   Q   E   G   A   V   H   T   A   L   A   G   A   L   E   A   E   M   D

841/281                                             871/291
GGT GCA AAG GGA AGG CTG TCC TCT GGC CAC TTG AAA TGT CGC CTG AAA ATG GAT AAA CTT
GGT GCA AAG GGC CGC CTG TCC TCT GGC CAC TTG AAA TGT CGC CTG AAA ATG GAT AAA CTT
GGT GCA AAA GGT CGT CTG TCT TCT GGT CAC CTG AAA TGC CGT CTG AAA ATG GAT AAA CTG
 G   A   K   G   R   L   S   S   G   H   L   K   C   R   L   K   M   D   K   L
```

FIGURE 10B (continued)

```
901/301                                              931/311
AGA TTG AAG GGC GTG TCA TAC TCC TTG TGT ACT GCA GCG TTC ACA TTC ACC AAG ATC CCG
CGT TTG AAG GGT GTG TCA TAC TCC TTG TGT ACT GCA GCG TTC ACA TTC ACC AAG ATC CCG
CGT CTG AAA GGT GTT TCT TAC TCT CTG TGC ACC GCA GCG TTC ACC TTC ACC AAA ATC CCG
 R   L   K   G   V   S   Y   S   L   C   T   A   A   F   T   F   T   K   I   P

961/321                                              991/331
GCT GAA ACA CTG CAC GGG ACA GTC ACA GTG GAG TTA CAG TAC GCA GGG ACA GAT GGA CCT
GCT GAA ACA CTG CAC GGG ACA GTC ACA GTG GAG TTA CAG TAC GCA GGG ACA GAT GGT CCT
GCT GAA ACC CTG CAC GGT ACC GTT ACC GTG GAA CTG CAG TAC GCA GGT ACC GAT GGT CCG
 A   E   T   L   H   G   T   V   T   V   E   L   Q   Y   A   G   T   D   G   P

1021/341                                             1051/351
TGC AAG GTT CCA GCT CAG ATG GCG GTG GAC ATG CAA ACT CTG ACC CCA GTT GGG AGG TTG
TGC AAG GTT CCA GCT CAG ATG GCG GTG GAC ATG CAA ACT CTG ACC CCA GTT GGG CGT TTG
TGC AAA GTT CCG GCT CAG ATG GCG GTG GAT ATG CAG ACC CTG ACC CCG GTT GGT CGT CTG
 C   K   V   P   A   Q   M   A   V   D   M   Q   T   L   T   P   V   G   R   L

1081/361                                             1111/371
ATA ACC GCT AAC CCC GTA ATC ACT GAA AGC ACT GAG AAC TCT AAG ATG ATG CTG GAA CTT
ATC ACC GCT AAC CCG GTA ATC ACT GAA AGC ACT GAG AAC TCT AAG ATG ATG CTG GAA CTT
ATC ACC GCT AAC CCG GTT ATC ACC GAA TCT ACC GAA AAC TCT AAA ATG ATG CTG GAA CTG
 I   T   A   N   P   V   I   T   E   S   T   E   N   S   K   M   M   L   E   L

1141/381                                             1171/391
GAT CCA CCA TTT GGG GAC TCT TAC ATT GTC ATA GGA GTC GGG GAG AAG AAG ATC ACC CAC
GAT CCA CCA TTT GGG GAC TCT TAC ATT GTC ATC GGT GTC GGG GAG AAG AAG ATC ACC CAC
GAT CCG CCA TTC GGT GAT TCT TAC ATC GTT ATC GGT GTG GGT GAA AAA AAA ATC ACC CAC
 D   P   P   F   G   D   S   Y   I   V   I   G   V   G   E   K   K   I   T   H

1201/401                                             1231/411
CAC TGG CAC AGG AGT GGC AGC ACC ATT GGA AAA GCA TTT GAA GCC ACT GTG AGA GGT GCC
CAC TGG CAC CGC AGT GGC AGC ACC ATT GGT AAA GCA TTT GAA GCC ACT GTG CGT GGT GCC
AAA CGT ATG GCA GTT CTG GGT GAT ACA GCC TGG GAT TTC GGT TCT GTT GGT GGT GCT CTG
 H   W   H   R   S   G   S   T   I   G   K   A   F   E   A   T   V   R   G   A

1261/421                                             1291/431
AAG AGA ATG GCA GTC TTG GGA GAC ACA GCC TGG GAC TTT GGA TCA GTT GGA GGC GCT CTC
AAG CGT ATG GCA GTC TTG GGT GAC ACA GCC TGG GAC TTT GGT TCA GTT GGC GGC GCT CTC
AAA CGT ATG GCA GTT CTG GGT GAT ACA GCC TGG GAT TTC GGT TCT GTT GGT GGT GCT CTG
 K   R   M   A   V   L   G   D   T   A   W   D   F   G   S   V   G   G   A   L

1321/441                                             1351/451
AAC TCA TTG GGC AAG GGC ATC CAT CAA ATT TTT GGA GCA GCT TTC AAA TCA TTG TTT GGA
AAC TCA TTG GGC AAG GGC ATC CAT CAA ATT TTT GGC GCA GCT TTC AAA TCA TTG TTT GGT
AAC TCT CTG GGT AAG GGT ATC CAC CAG ATC TTC GGT GCA GCT TTC AAA TCT CTG TTC GGT
 N   S   L   G   K   G   I   H   Q   I   F   G   A   A   F   K   S   L   F   G
```

FIGURE 10B (continued)

```
1381/461                                            1411/471
GGA ATG TCC TGG TTC TCA CAA ATT CTC ATT GGA ACG TTG CTG ATG TGG TTG GGT CTG AAC
GGT ATG TCC TGG TTC TCA CAA ATT CTC ATT GGA ACG TTG CTG ATG TGG TTG GGT CTG AAC
GGT ATG TCT TGG TTC TCT CAA ATC CTG ATC GGT ACC CTG CTG ATG TGG CTG GGT CTG AAC
 G   M   S   W   F   S   Q   I   L   I   G   T   L   L   M   W   L   G   L   N

1441/481                                            1471/491
ACA AAG AAT GGA TCT ATT TCC CTT ATG TGC TTG GCC TTA GGG GGA GTG TTG ATC TTC TTA
ACA AAG GAG GGC TCT ATT TCC CTT ATG TGC TTG GCC TTA GGG GGT GTG TTG ATC TTC TTA
ACC AAA AAC GGT TCT ATC TCT CTG ATG TGC CTG GCC CTG GGT GGT GTT CTG ATC TTC CTG
 T   K   N   G   S   I   S   L   M   C   L   A   L   G   G   V   L   I   F   L
         E*  (SEQ ID NO: 23)
1501/501
TCC ACA GCC GTC TCT GCT (SEQ ID NO: 19)
TCC ACA GCC GTC TCT GCT (SEQ ID NO: 20)
TCT ACC GCC GTT TCT GCT (SEQ ID NO: 21)
 S   T   A   V   S   A  (SEQ ID NO: 22)
```

FIGURE 10B (continued)

NS4A 381 bp (127aa) orig codon 53.8% GC  codon opt 52.8% GC

Extra sequence added for 15 bp for Starting codon + 2 extra AAs at 5' and 2
AAs at 3' end) and NcoI-XmaI ends
Cut with NcoI and XmaI sites in pYA4763 (pBR *ori*), pYA4589 (p15A *ori*) and
pYA4595 (pSC101 *ori*) lysis vectors.

```
1/1                                            31/11
ATG GAA AAA GGA GCG GCT TTT GGA GTG ATG        GAA GCC CTG GGA ACA CTG CCA GGA CAC ATG
    GGT GCT GCT TTC GGT GTT ATG                GAA GCT CTG GGT ACC CTG CCG GGT CAC ATG
 M   E   K   G   A   A   F   G   V   M          E   A   L   G   T   L   P   G   H   M
            → NS4A
61/21                                          91/31
ACA GAG AGA TTC CAG GAA GCC ATT GAC AAC        CTC GCT GTG CTC ATG CGG GCA GAG ACT GGA
ACC GAA CGT TTC CAG GAA GCT ATC GAT AAC        CTG GCT GTT CTG ATG CGT GCT GAA ACC GGT
 T   E   R   F   Q   E   A   I   D   N          L   A   V   L   M   R   A   E   T   G

121/41                                         151/51
AGC AGG CCT TAC AAA GCC GCG GCG GCC CAA        TTG CCG GAG ACC CTA GAG ACC ATT ATG CTT
TCT CGT CCG TAC AAA GCT GCT GCT GCT CAG        CTG CCG GAA ACC CTG GAA ACC ATC ATG CTG
 S   R   P   Y   K   A   A   A   A   Q          L   P   E   T   L   E   T   I   M   L

181/61                                         211/71
TTG GGG TTG CTG GGA ACA GTC TCG CTG GGA        ATC TTT TTC GTC TTG ATG AGG AAC AAG GGC
CTG GGT CTG CTG GGT ACC GTT TCT CTG GGT        ATC TTC TTC GTT CTG ATG CGT AAC AAA GGT
 L   G   L   L   G   T   V   S   L   G          I   F   F   V   L   M   R   N   K   G

241/81                                         271/91
ATA GGG AAG ATG GGC TTT GGA ATG GTG ACT        CTT GGG GCC AGC GCA TGG CTC ATG TGG CTC
ATC GGT AAA ATG GGT TTC GGT ATG GTT ACC        CTG GGT GCT TCT GCT TGG CTG ATG TGG CTG
 I   G   K   M   G   F   G   M   V   T          L   G   A   S   A   W   L   M   W   L

301/101                                        331/111
TCG GAA ATT GAG CCA GCC AGA ATT GCA TGT        GTC CTC ATT GTT GTG TTC CTA TTG CTG GTG
TCT GAA ATC GAA CCG GCT CGT ATC GCT TGT        GTT CTG ATC GTT GTT TTC CTG CTG CTG GTT
 S   E   I   E   P   A   R   I   A   C          V   L   I   V   V   F   L   L   L   V

361/121
GTG CTC ATA CCT GAG CCA GAA AAG CAA AGA        (SEQ ID NO: 24)    original codon
GTT CTG ATC CCG GAA CCG GAA AAA CAG CGT GCC GGC TAATCCCGGG (SEQ ID NO: 25)
                                                             optimized codon
 V   L   I   P   E   P   E   K   Q   R   A   G       XmaI (SEQ ID NO: 26)
```

FIGURE 11A

Codon-optimized sequence with 6 x His tagged sequence

```
CC ATG GAA AAA GGT GCT GCT TTC GGT GTT ATG GAA GCT CTG GGT ACC CTG CCG GGT CAC
   M   E   K   G   A   A   F   G   V   M   E   A   L   G   T   L   P   G   H
ATG ACC GAA CGT TTC CAG GAA GCT ATC GAT AAC CTG GCT GTT CTG ATG CGT GCT GAA ACC
 M   T   E   R   F   Q   E   A   I   D   N   L   A   V   L   M   R   A   E   T
GGT TCT CGT CCG TAC AAA GCT GCT GCT GCT CAG CTG CCG GAA ACC CTG GAA ACC ATC ATG
 G   S   R   P   Y   K   A   A   A   A   Q   L   P   E   T   L   E   T   I   M
CTG CTG GGT CTG CTG GGT ACC GTT TCT CTG GGT ATC TTC TTC GTT CTG ATG CGT AAC AAA
 L   L   G   L   L   G   T   V   S   L   G   I   F   F   V   L   M   R   N   K
GGT ATC GGT AAA ATG GGT TTC GGT ATG GTT ACC CTG GGT GCT TCT GCT TGG CTG ATG TGG
 G   I   G   K   M   G   F   G   M   V   T   L   G   A   S   A   W   L   M   W
CTG TCT GAA ATC GAA CCG GCT CGT ATC GCT TGT GTT CTG ATC GTT GTT TTC CTG CTG CTG
 L   S   E   I   E   P   A   R   I   A   C   V   L   I   V   V   F   L   L   L
                                                          NaeI
GTT GTT CTG ATC CCG GAA CCG GAA AAA CAC CGT GCC GGC CAC CAT CAC CAT CAC CAT TAG
 V   V   L   I   P   E   P   E   K   Q   R   A   G   H   H   H   H   H   H   *
 NaeI    XmaI
CCGGCTAATcccggg  (SEQ ID NO: 27)
                 (SEQ ID NO: 28, protein sequence)
```

FIGURE 11B

NS4B codon opt NcoI-SmaI 765 bp
Orig 52.5% GC best codon 52.7% GC 254 aa

Extra sequence added for 12 bp for Starting codon + 1 extra AA at 5' and 2 AAs at 3' end) and NcoI-XmaI ends

Cut with NcoI and XmaI sites in pYA4763 (pBR *ori*), pYA4589 (p15A *ori*) and pYA4595(pSC101 *ori*) lysis vectors.

```
1/1                                         31/11
ATG GAA AAT GAA CTC GGA TGG TTG GAG AGA ACA AAG AGT GAC CTA AGC CAT CTA ATG GGA
AAC GAA CTG GGT TGG CTG GAA CGT ACC AAA TCT GAT CTG TCT CAC CTG ATG GGT
 M   E   N   E   L   G   W   L   E   R   T   K   S   D   L   S   H   L   M   G
         → NS4B
61/21                                       91/31
AGG AGA GAG GAG GGG GCA ACC ATG GGA TTC TCA ATG GAC ATT GAC CTG CGG CCA GCC TCA
CGT CGT GAA GAA GGT GCT ACC ATG GGT TTC TCT ATG GAT ATC GAT CTG CGT CCG GCT TCT
 R   R   E   E   G   A   T   M   G   F   S   M   D   I   D   L   R   P   A   S

121/41                                      151/51
GCT TGG GCC ATC TAT GCT GCC TTG ACA ACT TTC ATT ACC CCA GCC GTC CAA CAT GCA GTG
GCT TGG GCT ATC TAC GCT GCT CTG ACC ACC TTC ATC ACC CCG GCT GTT CAG CAC GCT GTT
 A   W   A   I   Y   A   A   L   T   T   F   I   T   P   A   V   Q   H   A   V

181/61                                      211/71
ACC ACT TCA TAC AAC AAC TAC TCC TTA ATG GCG ATG GCC ACG CAA GCT GGA GTG TTG TTT
ACC ACC TCT TAC AAC AAC TAC TCT CTG ATG GCT ATG GCT ACC CAG GCT GGT GTT CTG TTC
 T   T   S   Y   N   N   Y   S   L   M   A   M   A   T   Q   A   G   V   L   F

241/81                                      271/91
GGT ATG GGC AAA GGG ATG CCA TTC TAC GCA TGG GAC TTT GGA GTC CCG CTG CTA ATG ATA
GGT ATG GGT AAA GGT ATG CCG TTC TAC GCG TGG GAT TTC GGT GTT CCG CTG CTG ATG ATC
 G   M   G   K   G   M   P   F   Y   A   W   D   F   G   V   P   L   L   M   I

301/101                                     331/111
GGT TGC TAC TCA CAA TTA ACG CCC CTG ACC CTA ATA GTG GCC ATC ATT TTG CTC GTG GCG
GGT TGC TAC TCT CAG CTG ACC CCG CTG ACC CTG ATC GTT GCT ATC ATC CTG CTG GTT GCT
 G   C   Y   S   Q   L   T   P   L   T   L   I   V   A   I   I   L   L   V   A

361/121                                     391/131
CAC TAC ATG TAC TTG ATC CCA GGG CTG CAG GCA GCA GCT GCG CGT GCT GCC CAG AAG AGA
CAC TAC ATG TAC CTG ATC CCG GGT CTG CAG GCT GCT GCT GCT CGT GCT GCT CAG AAA CGT
 H   Y   M   Y   L   I   P   G   L   Q   A   A   A   A   R   A   A   Q   K   R

421/141                                     451/151
ACG GCA GCT GGC ATC ATG AAG AAC CCT GTT GTG GAT GGA ATA GTG GTG ACT GAC ATT GAC
ACC GCT GCT GGT ATC ATG AAA AAC CCG GTT GTT GAT GGT ATC GTT GTT ACC GAT ATC GAT
 T   A   A   G   I   M   K   N   P   V   V   D   G   I   V   V   T   D   I   D
```

FIGURE 12A

```
481/161                                             511/171
ACA ATG ACA ATT GAC CCC CAA GTG GAG AAA AAG ATG GGA CAG GTG CTA CTC ATG GCA GTA
ACC ATG ACC ATC GAT CCG CAG GTT GAA AAA AAA ATG GGT CAG GTT CTG CTG ATG GCT GTT
 T   M   T   I   D   P   Q   V   E   K   K   M   G   Q   V   L   L   M   A   V

541/181                                             571/191
GCC GTC TCC AGC GCC ATA CTG TCG CGG ACC GCC TGG GGG TGG GGG GAG GCT GGG GCC CTG
GCT GTT TCT TCT GCT ATC CTG TCT CGT ACC GCT TGG GGT TGG GGT GAA GCT GGT GCT CTG
 A   V   S   S   A   I   L   S   R   T   A   W   G   W   G   E   A   G   A   L

601/201                                             631/211
ATC ACA GCC GCA ACT TCC ACT TTG TGG GAA GGC TCT CCG AAC AAG TAC TGG AAC TCC TCT
ATC ACC GCT GCT ACC TCT ACC CTG TGG GAA GGT TCT CCG AAC AAA TAC TGG AAC TCT TCT
 I   T   A   A   T   S   T   L   W   E   G   S   P   N   K   Y   W   N   S   S

661/221                                             691/231
ACA GCC ACT TCA CTG TGT AAC ATT TTT AGG GGA AGT TAC TTG GCT GGA GCT TCT CTA ATC
ACC GCT ACC TCT CTG TGC AAC ATC TTC CGT GGT TCT TAC CTG GCT GGT GCT TCT CTG ATC
 T   A   T   S   L   C   N   I   F   R   G   S   Y   L   A   G   A   S   L   I

721/241
TAC ACA GTA ACA AGA AAC GCT GGC TTG GTC AAG AGA    (SEQ ID NO: 29)    orig codon
TAC ACC GTT ACC CGT AAC GCT GGT CTG GTT AAA CGT GCC GGC TAA TCCCGGG  (SEQ ID NO:
                                                                      30) opt codon
 Y   T   V   T   R   N   A   G   L   V   K   R   A   G   *   XmaI  (SEQ ID NO: 31)
```

FIGURE 12A (continued)

6 x His tagged sequence
```
  NcoI
CC ATG GAA AAC GAA CTG GGT TGG CTG GAA CGT ACC AAA TCT GAT CTG TCT CAC CTG ATG
    M   E   N   E   L   G   W   L   E   R   T   K   S   D   L   S   H   L   M
GGT CGT CGT GAA GAA GGT GCT ACT ATG GGT TTC TCT ATG GAT ATC GAT CTG CGT CCG GCT
 G   R   R   E   E   G   A   T   M   G   F   S   M   D   I   D   L   R   P   A
TCT GCT TGG GCT ATC TAC GCT GCT CTG ACC ACC TTC ATC ACC CCG GCT GTT CAG CAC GCT
 S   A   W   A   I   Y   A   A   L   T   T   F   I   T   P   A   V   Q   H   A
GTT ACC ACC TCT TAC AAC AAC TAC TCT CTG ATG GCT ATG GCT ACC CAG GCT GGT GTT CTG
 V   T   T   S   Y   N   N   Y   S   L   M   A   M   A   T   Q   A   G   V   L
TTC GGT ATG GGT AAA GGT ATG CCG TTC TAC GCG TGG GAT TTC GGT GTT CCG CTG CTG ATG
 F   G   M   G   K   G   M   P   F   Y   A   W   D   F   G   V   P   L   L   M
ATC GGT TGC TAC TCT CAG CTG ACC CCG CTG ACC CTG ATC GTT GCT ATC ATC CTG CTG GTT
 I   G   C   Y   S   Q   L   T   P   L   T   L   I   V   A   I   I   L   L   V
GCT CAC TAC ATG TAC CTG ATT CCG GGT CTG CAG GCT GCT GCT GCT CGT GCT GCT CAG AAA
 A   H   Y   M   Y   L   I   P   G   L   Q   A   A   A   A   R   A   A   Q   K
```

FIGURE 12B

```
CGT ACC GCT GCT GGT ATC ATG AAA AAC CCG GTT GTT GAT GGT ATC GTT GTT ACC GAT ATC
 R   T   A   A   G   I   M   K   N   P   V   V   D   G   I   V   V   T   D   I
GAT ACC ATG ACC ATC GAT CCG CAG GTT GAA AAA AAA ATG GGT CAG GTT CTG CTG ATG GCT
 D   T   M   T   I   D   P   Q   V   E   K   K   M   G   Q   V   L   L   M   A
GTT GCT GTT TCT TCT GCT ATC CTG TCT CGT ACC GCT TGG GGT TGG GGT GAA GCT GGT GCT
 V   A   V   S   S   A   I   L   S   R   T   A   W   G   W   G   E   A   G   A
CTG ATC ACC GCT GCT ACC TCT ACC CTG TGG GAA GGT TCT CCG AAC AAA TAC TGG AAC TCT
 L   I   T   A   A   T   S   T   L   W   E   G   S   P   N   K   Y   W   N   S
TCT ACC GCT ACC TCT CTG TGC AAC ATC TTC CGT GGT TCT TAC CTG GCT GGT GCT TCT CTG
 S   T   A   T   S   L   C   N   I   F   R   G   S   Y   L   A   G   A   S   L
                                                                NaeI
ATC TAC ACC GTT ACC CGT AAC GCT GGT CTG GTT AAA CGT GCC GGC CAC CAT CAC CAT CAC
 I   Y   T   V   T   R   N   A   G   L   V   K   R   A   G   H   H   H   H   H
         NaeI    XmaI
CAT TAG CCGGCTAATcccggg   (SEQ ID NO: 32)
 H   *                    (SEQ ID NO: 33)
```

FIGURE 12B (continued)

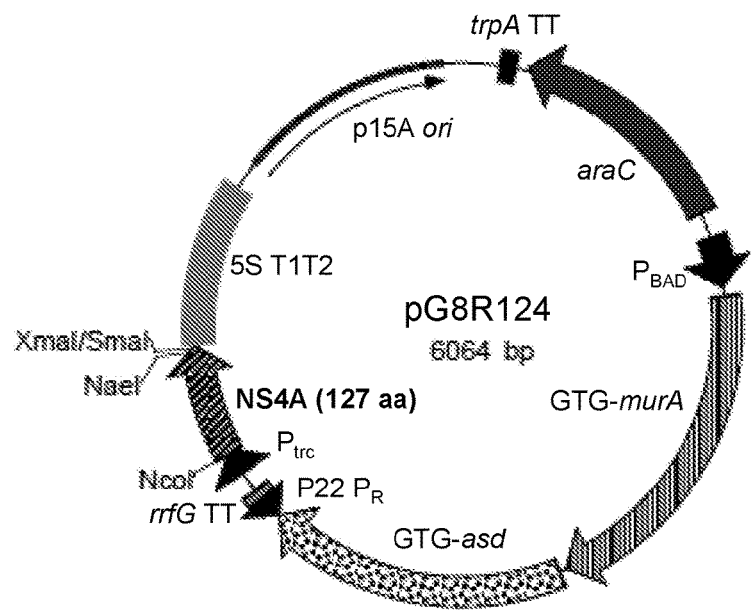

FIGURE 13

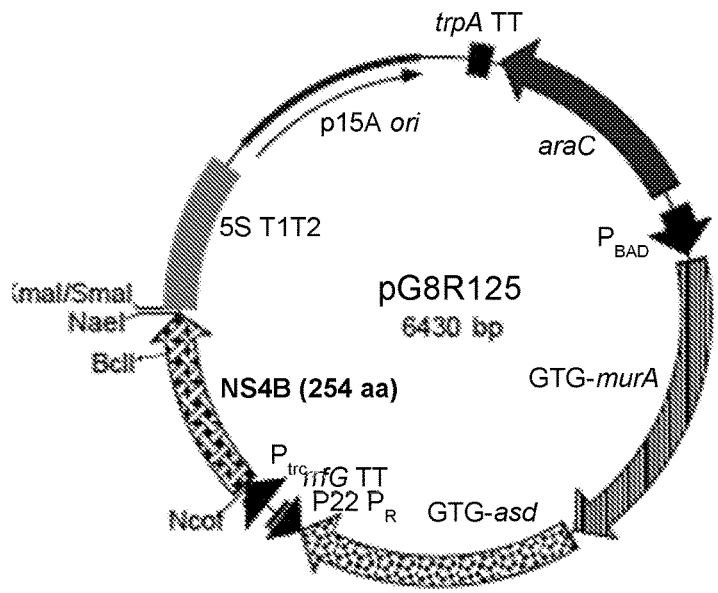

FIGURE 14 prM-E 1800 bp (600 aa)
original 48.0 GC & codon op 51.9% GC

Cut with NcoI and XmaI sites in pYA4763 (pBR ori), pYA4589 (p15A ori) and pYA4595 (pSC101 ori) lysis vector.

N-glycosylation sites (bolded, aa 254, and 577) are unchanged.

```
NcoI-XmaI ends tagged
1/1                                           31/11
ATG GAA AAA GCG GAG GTC ACT AGA CGT GGG AGT GCA TAC TAT ATG TAC TTG GAC AGA AAC
ATG GAA AAA GCG GAA GTT ACC CGT CGT GGT TCT GCG TAC TAC ATG TAC CTG GAT CGC AAC
 M   E   K   A   E   V   T   R   R   G   S   A   Y   Y   M   Y   L   D   R   N
        → prM protein
61/21                                         91/31
GAT GCT GGG GAG GCC ATA TCT TTT CCA ACC ACA TTG GGG ATG AAT AAG TGT TAT ATA CAG
GAT GCG GGT GAA GCG ATC TCT TTC CCG ACC ACC CTG GGT ATG AAC AAA TGC TAC ATC CAG
 D   A   G   E   A   I   S   F   P   T   T   L   G   M   N   K   C   Y   I   Q
```

FIGURE 15A

```
121/41                                          151/51
ATC ATG GAT CTT GGA CAC ATG TGT GAT GCC ACC ATG AGC TAT GAA TGC CCT ATG CTG GAT
ATC ATG GAT CTG GGT CAC ATG TGC GAT GCC ACC ATG TCT TAC GAA TGC CCG ATG CTG GAT
 I   M   D   L   G   H   M   C   D   A   T   M   S   Y   E   C   P   M   L   D

181/61                                          211/71
GAG GGG GTG GAA CCA GAT GAC GTC GAT TGT TGG TGC AAC ACG ACG TCA ACT TGG GTT GTG
GAA GGT GTT GAA CCG GAT GAT GTT GAT TGC TGG TGC AAC ACC ACC TCT ACT TGG GTT GTT
 E   G   V   E   P   D   D   V   D   C   W   C   N   T   T   S   T   W   V   V

241/81                                          271/91
TAC GGA ACC TGC CAT CAC AAA AAA GGT GAA GCA CGG AGA TCT AGA AGA ATC AGG TGC ATA
TAC GGT ACC TGC CAC CAC AAA AAA GGT GAA GCG CGT CGT TCT CGT CGT ATC CGC TGC ATC
 Y   G   T   C   H   H   K   K   G   E   A   R   R   S   R   R   I   R   C   I
                                                                    → E protein
301/101                                         331/111
GGA GTC AGC AAT AGG GAC TTT GTG GAA GGT ATG TCA GGT GGG ACT TGG GTT GAT GTT GTC
GGT GTT TCT AAC CGT GAC TTC GTT GAA GGT ATG TCT GGT GGT ACC TGG GTT GAT GTT GTT
 G   V   S   N   R   D   F   V   E   G   M   S   G   G   T   W   V   D   V   V 361/121                                         391/131
TTG GAA CAT GGA GGT TGT GTC ACC GTA ATG GCA CAG GAC AAA CCG ACT GTC GAC ATA GAG
CTG GAA CAC GGT GGT TGC GTT ACC GTT ATG GCG CAG GAT AAA CCG ACC GTT GAT ATC GAA
 L   E   H   G   G   C   V   T   V   M   A   Q   D   K   P   T   V   D   I   E 421/141                                         451/151
CTG GTT ACA ACA ACA GTC AGC AAC ATG GCG GAG GTA AGA TCC TAC TGC TAT GAG GCA TCA
CTG GTT ACC ACC ACC GTT TCT AAC ATG GCG GAA GTT CGT TCT TAC TGC TAC GAA GCG TCT
 L   V   T   T   T   V   S   N   M   A   E   V   R   S   Y   C   Y   E   A   S 481/161                                         511/171
ATA TCA GAC ATG GCT TCT GAC AGC CGC TGC CCA ACA CAA GGT GAA GCC TAC CTT GAC AAG
ATC TCT GAT ATG GCG TCT GAT AGC CGT TGC CCG ACC CAG GGT GAA GCG TAC CTG GAT AAA
 I   S   D   M   A   S   D   S   R   C   P   T   Q   G   E   A   Y   L   D   K 541/181                                         571/191
CAA TCA GAC ACT CAA TAT GTC TGC AAA AGA ACG TTA GTG GAC AGA GGC TGG GGA AAT GGA
CAG TCT GAT ACC CAG TAC GTT TGC AAA CGT ACC CTG GTT GAT CGT GGT TGG GGC AAC GGT
 Q   S   D   T   Q   Y   V   C   K   R   T   L   V   D   R   G   W   G   N   G 601/201                                         631/211
TGT GGA CTT TTT GGC AAA GGG AGC CTG GTG ACA TGC GCT AAG TTT GCA TGC TCC AAG AAA
TGC GGT CTG TTC GGT AAA GGT TCT CTG GTT ACC TGC GCT AAA TTC GCA TGC TCT AAA AAA
 C   G   L   F   G   K   G   S   L   V   T   C   A   K   F   A   C   S   K   K 661/221                                         691/231
ATG ACC GGG AAG AGC ATC CAG CCA GAG AAT CTG GAG TAC CGG ATA ATG CTG TCA GTT CAT
ATG ACC GGT AAA AGC ATC CAG CCG GAA AAC CTG GAA TAC CGT ATC ATG CTG TCT GTT CAC
 M   T   G   K   S   I   Q   P   E   N   L   E   Y   R   I   M   L   S   V   H
```

FIGURE 15A (continued)

```
721/241                                          751/251
GGC TCC CAG CAC AGT GGG ATG ATC GTT AAT GAC ACA GGA CAT GAA ACT GAT GAG AAT AGA
GGC TCC CAG CAC TCT GGT ATG ATC GTT AAC GAT ACC GGT CAC GAA ACC GAT GAA AAC CGT
 G   S   Q   H   S   G   M   I   V   N   D   T   G   H   E   T   D   E   N   R

781/261                                          811/271
GCG AAA GTT GAG ATA ACG CCC AAT TCA CCG AGA GCC GAA GCC ACC CTG GGG GGT TTT GGA
GCG AAA GTT GAA ATC ACC CCG AAC TCT CCG CGT GCC GAA GCC ACC CTG GGT GGT TTC GGT
 A   K   V   E   I   T   P   N   S   P   R   A   E   A   T   L   G   G   F   G

841/281                                          871/291
AGC CTA GGA CTT GAT TGT GAA CCG AGG ACA GGC CTT GAC TTT TCA GAT TTG TAT TAC TTG
TCT CTG GGT CTG GAT TGC GAA CCG CGT ACC GGT CTG GAT TTC TCT GAT CTG TAC TAC CTG
 S   L   G   L   D   C   E   P   R   T   G   L   D   F   S   D   L   Y   Y   L

901/301                                          931/311
ACT ATG AAT AAC AAG CAC TGG TTG GTT CAC AAG GAG TGG TTC CAC GAC ATT CCA TTA CCT
ACC ATG AAC AAC AAG CAC TGG CTG GTT CAC AAG GAA TGG TTC CAC GAT ATC CCG CTG CCG
 T   M   N   N   K   H   W   L   V   H   K   E   W   F   H   D   I   P   L   P

961/321                                          991/331
TGG CAC GCT GGG GCA GAC ACC GGA ACT CCA CAC TGG AAC AAC AAA GAA GCA CTG GTA GAG
TGG CAC GCT GGT GCA GAT ACC GGT ACC CCG CAC TGG AAC AAC AAA GAA GCA CTG GTT GAA
 W   H   A   G   A   D   T   G   T   P   H   W   N   N   K   E   A   L   V   E

1021/341                                         1051/351
TTC AAG GAC GCA CAT GCC AAA AGG CAA ACT GTC GTG GTT CTA GGG AGT CAA GAA GGA GCA
TTC AAA GAT GCA CAC GCC AAA CGT CAG ACC GTT GTT GTT CTG GGT TCT CAG GAA GGT GCA
 F   K   D   A   H   A   K   R   Q   T   V   V   V   L   G   S   Q   E   G   A

1081/361                                         1111/371
GTT CAC ACG GCC CTT GCT GGA GCT CTG GAG GCT GAG ATG GAT GGT GCA AAG GGA AGG CTG
GTT CAC ACC GCC CTG GCT GGT GCT CTG GAA GCT GAA ATG GAT GGT GCA AAA GGT CGT CTG
 V   H   T   A   L   A   G   A   L   E   A   E   M   D   G   A   K   G   R   L

1141/381                                         1171/391
TCC TCT GGC CAC TTG AAA TGT CGC CTG AAA ATG GAT AAA CTT AGA TTG AAG GGC GTG TCA
TCT TCT GGT CAC CTG AAA TGC CGT CTG AAA ATG GAT AAA CTG CGT CTG AAA GGT GTT TCT
 S   S   G   H   L   K   C   R   L   K   M   D   K   L   R   L   K   G   V   S

1201/401                                         1231/411
TAC TCC TTG TGT ACT GCA GCG TTC ACA TTC ACC AAG ATC CCG GCT GAA ACA CTG CAC GGG
TAC TCT CTG TGC ACC GCA GCG TTC ACC TTC ACC AAA ATC CCG GCT GAA ACC CTG CAC GGT
 Y   S   L   C   T   A   A   F   T   F   T   K   I   P   A   E   T   L   H   G

1261/421                                         1291/431
ACA GTC ACA GTG GAG TTA CAG TAC GCA GGG ACA GAT GGA CCT TGC AAG GTT CCA GCT CAG
ACC GTT ACC GTG GAA CTG CAG TAC GCA GGT ACC GAT GGT CCG TGC AAA GTT CCG GCT CAG
 T   V   T   V   E   L   Q   Y   A   G   T   D   G   P   C   K   V   P   A   Q
```

FIGURE 15A (continued)

```
1321/441                                         1351/451
ATG GCG GTG GAC ATG CAA ACT CTG ACC CCA GTT GGG AGG TTG ATA ACC GCT AAC CCC GTA
ATG GCG GTG GAT ATG CAG ACC CTG ACC CCG GTT GGT CGT CTG ATC ACC GCT AAC CCG GTT
 M   A   V   D   M   Q   T   L   T   P   V   G   R   L   I   T   A   N   P   V

1381/461                                         1411/471
ATC ACT GAA AGC ACT GAG AAC TCT AAG ATG ATG CTG GAA CTT GAT CCA CCA TTT GGG GAC
ATC ACC GAA TCT ACC GAA AAC TCT AAA ATG ATG CTG GAA CTG GAT CCG CCG TTC GGT GAT
 I   T   E   S   T   E   N   S   K   M   M   L   E   L   D   P   P   F   G   D

1441/481                                         1471/491
TCT TAC ATT GTC ATA GGA GTC GGG GAG AAG AAG ATC ACC CAC CAC TGG CAC AGG AGT GGC
TCT TAC ATC GTT ATC GGT GTG GGT GAA AAA AAA ATC ACC CAC CAC TGG CAC CGC TCT GGC
 S   Y   I   V   I   G   V   G   E   K   K   I   T   H   H   W   H   R   S   G

1501/501                                         1531/511
AGC ACC ATT GGA AAA GCA TTT GAA GCC ACT GTG AGA GGT GCC AAG AGA ATG GCA GTC TTG
TCT ACC ATC GGT AAA GCA TTC GAA GCC ACC GTT CGT GGT GCC AAA CGT ATG GCA GTT CTG
 S   T   I   G   K   A   F   E   A   T   V   R   G   A   K   R   M   A   V   L

1561/521                                         1591/531
GGA GAC ACA GCC TGG GAC TTT GGA TCA GTT GGA GGC GCT CTC AAC TCA TTG GGC AAG GGC
GGT GAT ACA GCC TGG GAT TTC GGT TCT GTT GGT GGT GCT CTG AAC TCT CTG GGT AAA GGT
 G   D   T   A   W   D   F   G   S   V   G   G   A   L   N   S   L   G   K   G

1621/541                                         1651/551
ATC CAT CAA ATT TTT GGA GCA GCT TTC AAA TCA TTG TTT GGA GGA ATG TCC TGG TTC TCA
ATC CAC CAG ATC TTC GGT GCA GCT TTC AAA TCT CTG TTC GGT GGT ATG TCT TGG TTC TCT
 I   H   Q   I   F   G   A   A   F   K   S   L   F   G   G   M   S   W   F   S

1681/561                                         1711/571
CAA ATT CTC ATT GGA ACG TTG CTG ATG TGG TTG GGT CTG AAC ACA AAG AAT GGA TCT ATT
CAA ATC CTG ATC GGT ACC CTG CTG ATG TGG CTG GGT CTG AAC ACC AAA AAC GGT TCT ATC
 Q   I   L   I   G   T   L   L   M   W   L   G   L   N   T   K   N   G   S   I

1741/581                                         1771/591
TCC CTT ATG TGC TTG GCC TTA GGG GGA GTG TTG ATC TTC TTA TCC ACA GCC GTC TCT GCT
TCT CTG ATG TGC CTG GCC CTG GGT GGT GTT CTG ATC TTC CTG TCT ACC GCC GTT TCT GCT
 S   L   M   C   L   A   L   G   G   V   L   I   F   L   S   T   A   V   S   A

1801/601
GCC GGC TAA TCC CGG G      (SEQ ID NO: 34)
                           (SEQ ID NO: 35)
 A   G   *      XmaI       (SEQ ID NO: 36)
```

FIGURE 15A (continued)

6 x His tagged sequence

```
CC ATG GAA AAA GCG GAA GTT ACC CGT CGT GGT TCT GCG TAC TAC ATG TAC CTG GAT CGC
    M   E   K   A   E   V   T   R   R   G   S   A   Y   Y   M   Y   L   D   R
AAC GAT GCG GGT GAA GCG ATC TCT TTC CCG ACC ACC CTG GGT ATG AAC AAA TGC TAC ATC
 N   D   A   G   E   A   I   S   F   P   T   T   L   G   M   N   K   C   Y   I
CAG ATC ATG GAT CTG GGT CAC ATG TGC GAT GCC ACC ATG TCT TAC GAA TGC CCG ATG CTG
 Q   I   M   D   L   G   H   M   C   D   A   T   M   S   Y   E   C   P   M   L
GAT GAA GGT GTT GAA CCG GAT GAT GTT GAT TGC TGG TGC AAC ACC ACC TCT ACT TGG GTT
 D   E   G   V   E   P   D   D   V   D   C   W   C   N   T   T   S   T   W   V
GTT TAC GGT ACC TGC CAC CAC AAA AAA GGT GAA GCG CGT CGT TCT CGT CGT ATC CGC TGC
 V   Y   G   T   C   H   H   K   K   G   E   A   R   R   S   R   R   I   R   C
ATC GGT GTT TCT AAC CGT GAC TTC GTT GAA GGT ATG TCT GGT GGT ACC TGG GTT GAT GTT
 I   G   V   S   N   R   D   F   V   E   G   M   S   G   G   T   W   V   D   V
GTT CTG GAA CAC GGT GGT TGC GTT ACC GTT ATG GCG CAG GAT AAA CCG ACC GTT GAT ATC
 V   L   E   H   G   G   C   V   T   V   M   A   Q   D   K   P   T   V   D   I
GAA CTG GTT ACC ACC ACC GTT TCT AAC ATG GCG GAA GTT CGT TCT TAC TGC TAC GAA GCG
 E   L   V   T   T   T   V   S   N   M   A   E   V   R   S   Y   C   Y   E   A
TCT ATC TCT GAT ATG GCG TCT GAT AGC CGT TGC CCG ACC CAG GGT GAA GCG TAC CTG GAT
 S   I   S   D   M   A   S   D   S   R   C   P   T   Q   G   E   A   Y   L   D
AAA CAG TCT GAT ACC CAG TAC GTT TGC AAA CGT ACC CTG GTT GAT CGT GGT TGG GGC AAC
 K   Q   S   D   T   Q   Y   V   C   K   R   T   L   V   D   R   G   W   G   N
GGT TGC GGT CTG TTC GGT AAA GGT TCT CTG GTT ACC TGC GCT AAA TTC GCA TGC TCT AAA
 G   C   G   L   F   G   K   G   S   L   V   T   C   A   K   F   A   C   S   K
AAA ATG ACC GGT AAA AGC ATC CAG CCG GAA AAC CTG GAA TAC CGT ATC ATG CTG TCT GTT
 K   M   T   G   K   S   I   Q   P   E   N   L   E   Y   R   I   M   L   S   V
CAC GGC TCC CAG CAC TCT GGT ATG ATC GTT AAC GAT ACC GGT CAC GAA ACC GAT GAA AAC
 H   G   S   Q   H   S   G   M   I   V   N   D   T   G   H   E   T   D   E   N
CGT GCG AAA GTT GAA ATC ACC CCG AAC TCT CCG CGT GCC GAA GCC ACC CTG GGT GGT TTC
 R   A   K   V   E   I   T   P   N   S   P   R   A   E   A   T   L   G   G   F
GGT TCT CTG GGT CTG GAT TGC GAA CCG CGT ACC GGT CTG GAT TTC TCT GAT CTG TAC TAC
 G   S   L   G   L   D   C   E   P   R   T   G   L   D   F   S   D   L   Y   Y
CTG ACC ATG AAC AAC AAG CAC TGG CTG GTT CAC AAG GAA TGG TTC CAC GAT ATC CCG CTG
 L   T   M   N   N   K   H   W   L   V   H   K   E   W   F   H   D   I   P   L
CCG TGG CAC GCT GGT GCA GAT ACC GGT ACC CCG CAC TGG AAC AAC AAA GAA GCA CTG GTT
 P   W   H   A   G   A   D   T   G   T   P   H   W   N   N   K   E   A   L   V
GAA TTC AAA GAT GCA CAC GCC AAA CGT CAG ACC GTT GTT GTT CTG GGT TCT CAG GAA GGT
 E   F   K   D   A   H   A   K   R   Q   T   V   V   V   L   G   S   Q   E   G
GCA GTT CAC ACC GCC CTG GCT GGT GCT CTG GAA GCT GAA ATG GAT GGT GCA AAA GGT CGT
 A   V   H   T   A   L   A   G   A   L   E   A   E   M   D   G   A   K   G   R
CTG TCT TCT GGT CAC CTG AAA TGC CGT CTG AAA ATG GAT AAA CTG CGT CTG AAA GGT GTT
 L   S   S   G   H   L   K   C   R   L   K   M   D   K   L   R   L   K   G   V
TCT TAC TCT CTG TGC ACC GCA GCG TTC ACC TTC ACC AAA ATC CCG GCT GAA ACC CTG CAC
 S   Y   S   L   C   T   A   A   F   T   F   T   K   I   P   A   E   T   L   H
GGT ACC GTT ACC GTG GAA CTG CAG TAC GCA GGT ACC GAT GGT CCG TGC AAA GTT CCG GCT
 G   T   V   T   V   E   L   Q   Y   A   G   T   D   G   P   C   K   V   P   A
CAG ATG GCG GTG GAT ATG CAG ACC CTG ACC CCG GTT GGT CGT CTG ATC ACC GCT AAC CCG
 Q   M   A   V   D   M   Q   T   L   T   P   V   G   R   L   I   T   A   N   P
```

FIGURE 15B

```
GTT ATC ACC GAA TCT ACC GAA AAC TCT AAA ATG ATG CTG GAA CTG GAT CCG CCG TTC GGT
 V   I   T   E   S   T   E   N   S   K   M   M   L   E   L   D   P   P   F   G
GAT TCT TAC ATC GTT ATC GGT GTG GGT GAA AAA AAA ATC ACC CAC CAC TGG CAC CGC TCT
 D   S   Y   I   V   I   G   V   G   E   K   K   I   T   H   H   W   H   R   S
GGC TCT ACC ATC GGT AAA GCA TTC GAA GCC ACC GTT CGT GGT GCC AAA CGT ATG GCA GTT
 G   S   T   I   G   K   A   F   E   A   T   V   R   G   A   K   R   M   A   V
CTG GGT GAT ACA GCC TGG GAT TTC GGT TCT GTT GGT GGT GCT CTG AAC TCT CTG GGT AAA
 L   G   D   T   A   W   D   F   G   S   V   G   G   A   L   N   S   L   G   K
GGT ATC CAC CAG ATC TTC GGT GCA GCT TTC AAA TCT CTG TTC GGT GGT ATG TCT TGG TTC
 G   I   H   Q   I   F   G   A   A   F   K   S   L   F   G   G   M   S   W   F
TCT CAA ATC CTG ATC GGT ACC CTG CTG ATG TGG CTG GGT CTG AAC ACC AAA AAC GGT TCT
 S   Q   I   L   I   G   T   L   L   M   W   L   G   L   N   T   K   N   G   S
ATC TCT CTG ATG TGC CTG GCC CTG GGT GGT GTT CTG ATC TTC CTG TCT ACC GCC GTT TCT
 I   S   L   M   C   L   A   L   G   G   V   L   I   F   L   S   T   A   V   S
     NaeI                                       NaeI           XmaI
GCT GCC GGC CAC CAT CAC CAT CAC CAT TAG CCGGCTAATCCCGGG  (SEQ ID NO: 37)
 A   A   G   H   H   H   H   H   H   *                  (SEQ ID NO: 38)
```

FIGURE 15B (continued)

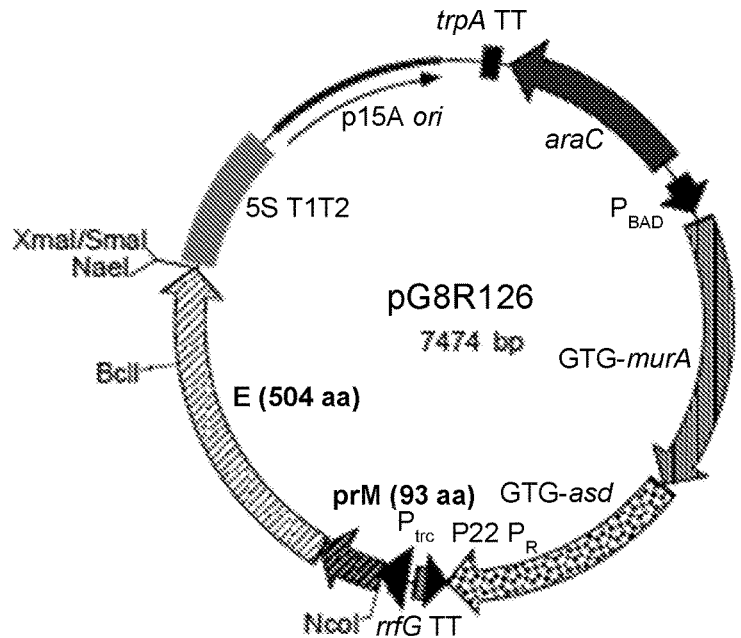

FIGURE 16

PROTECTIVE ANTI-ZIKV VACCINE WITHOUT INDUCING CROSS-REACTIONS WITH DENGUE

CROSS-REFERENCE TO RELATED APPLICATIONS

This application is the U.S. national stage application of International Patent Application No. PCT/US2017/043511, filed Jul. 24, 2017, which claims the benefit of U.S. Provisional Application Ser. No. 62/365,549, filed Jul. 22, 2017, and Ser. No. 62/467,340, filed Mar. 6, 2017, the disclosures of which are hereby incorporated by reference in their entirety, including all figures, tables and amino acid or nucleic acid sequences.

The Sequence Listing for this application is labeled "Seq-List.txt" which was created on Jul. 24, 2017 and is 88 KB. The entire content of the sequence listing is incorporated herein by reference in its entirety.

BACKGROUND OF THE INVENTION

Zika virus (ZIKV) infections are often associated with the adverse sequelae microcephaly, Guillian-Barre syndrome and, likely, other nervous system disorders that may be associated with prior exposure to dengue virus (DENV). Since ZIKV is transmitted by daytime active *Aedes aegypti* mosquitoes that are prevalent in the southern US, it is of critical importance to design and develop a safe efficacious vaccine to prevent ZIKV infection and especially to not induce immune responses that would be cross reactive with any of the four dengue virus types.

The subject application provides genetically modified recombinant facultative intracellular invasive bacterial pathogens that synthesize ZIKV protein antigens and are capable of: inducing mucosal immunity; and/or inducing CD4, and especially CD8 immune responses that should kill virus-infected cells. The genetically modified recombinant facultative intracellular invasive bacterial pathogens can be manufactured by fermentation technology to yield 1000-times more vaccine doses per liter of culture than can be produced using traditional DNA vaccine technologies and have the advantage of preservation by lyophilization in a thermostable form that obviates need for a cold chain. The lyophilized genetically modified recombinant facultative intracellular invasive bacterial pathogens can be reconstituted at a time and place for needle-free oral administration (not requiring highly trained medical care givers) for inducing immunity to ZIKV protein antigens.

In specific embodiments, the subject application provides newly developed innovative recombinant attenuated *Salmonella* vaccine (RASV) strains to deliver multiple ZIKV antigens (or other antigens) as a cost-effective vaccine to induce mucosal and systemic protective immunity. In addition to the advantages and characteristics discussed above, the disclosed RASV strains are attenuated, provide high immunogenicity and exhibit a desirable safety profile.

BRIEF SUMMARY OF THE INVENTION

It has been found that antibodies neutralizing dengue virus (DENV) react with ZIKV and disease symptoms after ZIKV infection are much more severe in animals previously infected with DENV or immunized with a DENV vaccine. This strongly suggests that cross reactivity of these two flaviviruses has the potential to complicate the development of a safe, efficacious vaccine to prevent or reduce either ZIKV or DENV infections. The cross-reactivity of neutralizing antibodies may also explain why the severe sequelae associated with ZIKV infections noted above are most often observed in countries with widespread previous exposure to DENV infections. It thus becomes important to develop vaccines that are safe and efficacious in conferring protection against flaviviruses, such as ZIKV and DENV, and that do not induce cross-reactive immune responses to each other or to other flaviviruses.

The subject application provides genetically modified recombinant facultative intracellular invasive bacterial pathogens (RFIIBPs), for example recombinant attenuated *Salmonella* vaccine (RASV) strains, with high immunogenicity, complete safety, and attenuation, and which also are unable to persist or be shed in an infective or viable form. These genetically modified recombinant facultative intracellular invasive bacterial pathogens also exhibit regulated delayed attenuation in vivo and regulated delayed in vivo synthesis of protective antigens. These antigens can be encoded by codon-optimized DNA sequences (in some embodiments, see, for example, FIGS. 3-6), and the genetically modified recombinant facultative intracellular invasive bacterial pathogens exhibit regulated delayed lysis in vivo.

The disclosed genetically modified recombinant facultative intracellular invasive bacterial pathogens system allows vaccines to be grown under conditions that enable them to display, after oral immunization, the capabilities of a wild-type strain. These RASV strains survive host defense stresses and efficiently colonize effector lymphoid tissues before manifesting attenuation (which precludes disease symptoms) and synthesizing protein antigens or to deliver DNA vaccines encoding antigens that induce protective immune responses. This system causes amplification of protective antigen production in vivo by the immunized host to induce mucosal and systemic antibody responses and also induces mucosal and systemic cellular immunity. The disclosed genetically modified recombinant facultative intracellular invasive bacterial pathogens system allows for large-scale, efficient, and economical production of genetically modified recombinant facultative intracellular invasive bacterial pathogens vaccines in a thermostable form for oral administration. These RASV vaccines are designed to generate safe, protective immunity against ZIKV and could also be used to design vaccines against other flaviviruses and reduce or eliminate the potential that vaccination against one flavivirus will engender immunity that will exacerbate disease caused by infection with, or vaccination against, another flavivirus.

BRIEF DESCRIPTION OF THE DRAWINGS

FIGS. 3-6. Native (upper sequence) and codon-optimized (lower) nucleic acid sequences encoding ZIKV antigens. FIG. 3 illustrates capsid protein C (309 bp, (103 aa) with 22 aa codons optimized (29 bp changed)). FIG. 4 depicts prM 288 bp ((96 aa) optimized and 279 bp (93 aa) original with 12 aa (18 bp) codon optimized and 3 N-terminal codons added in the optimized sequence). FIG. 5 shows E protein (1518 bp (506 aa) in codon optimized and 1512 bp (504 aa) in original; codon for aa 156(154 in original) and 483 (481 in original) changed to code Q in place of N; 54 aa (72 bp) were codon optimized and 2 N-terminal codons added in the optimized sequence). FIG. 6 illustrates NS5 (2718 bp (906 aa) in the codon optimized sequence and 2709 bp (903 aa) in original ZIKV sequence; 137 aa (196 bp) were codon optimized with 3 N-terminal codons added in the optimized sequence.

FIG. 7. Sequence of pYA4545.

FIGS. 10A and 10B. Nucleotide and amino acid sequences for PrM (FIG. 10A) and E protein (FIG. 10B). First line—original codon sequences in ZIKV; second line—codons optimized for good expression in *Salmonella*; third line—codons selected to represent the codons most frequently used by the most highly expressed *Salmonella* genes to achieve maximal rates of translation of mRNA to inhibit/prevent protein folding that would be needed to achieve prM interaction with E and ZIKV assembly.

FIGS. 11A and 11B. Nucleotide and amino acid sequences for NS4A (FIG. 11A). First line—original codon sequences in ZIKV; second line—codons optimized for good expression in *Salmonella*. FIG. 11B is the codon-optimized sequence encoding a histidine tagged NS4A.

FIGS. 12A and 12B. Nucleotide and amino acid sequences for NS4B (FIG. 12A). First line—original codon sequences in ZIKV; second line—codons optimized for good expression in *Salmonella*. FIG. 12B is the codon-optimized sequence encoding a histidine tagged NS4B.

FIG. 13. Plasmid map for pYA4589 containing NS4A.

FIG. 14. Plasmid map for pYA4589 containing NS4B.

FIGS. 15A and 15B. Nucleotide and amino acid sequences for prM-E fusion protein (FIG. 15A). First line—original codon sequences from ZIKV; second line—codons optimized for good expression in *Salmonella*. FIG. 15B is the codon-optimized sequence encoding a histidine tagged prM-E fusion protein.

FIG. 16. Plasmid map for pG8R126.

DETAILED DISCLOSURE OF THE INVENTION

Figure 1A:
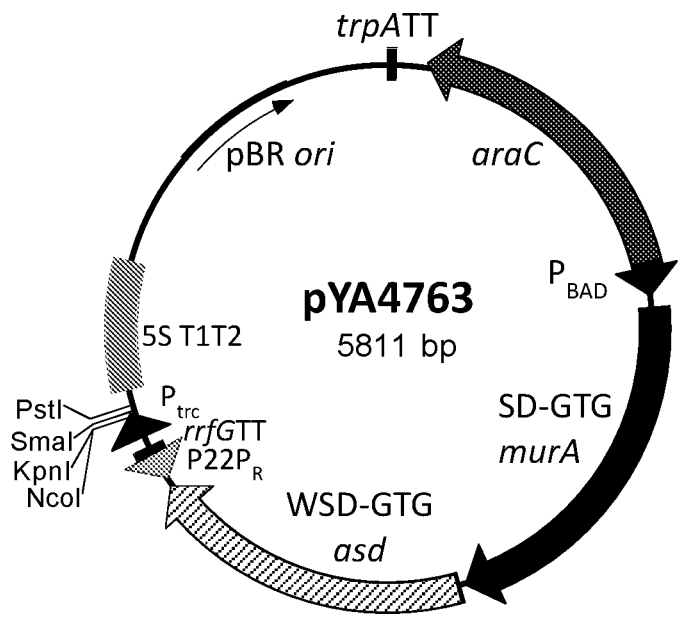
FIGS. 1A-1I. Plasmid maps. Lysis vector pYA4763 (1A). DNA vaccine vector designs are illustrated in FIGS. 1B (base vector), 1G (base vector containing nucleic acid sequence encoding non-codon optimized envelope (E) protein) and 1H (base vector containing nucleic acid sequence encoding codon optimized envelope (E) protein and amino acid substitutions at ASN154 and ASN481). Vector designs for expressing vaccine antigens (antigen-encoding lysis vectors) in the disclosed RFIIBPs and RASVs are illustrated in FIGS. 1C (base vector with modified Shine Dalgarno sequences), 1D (base vector), 1E (base vector of FIG. 1D containing nucleic acid sequence encoding codon optimized envelope (E) protein) and 1F (base vector of FIG. 1D containing nucleic acid sequence encoding codon optimized envelope (E) protein and amino acid substitutions at ASN154 and ASN481) and 1I (base vector containing nucleic acid sequence encoding a fusion protein of membrane precursor (prM) and NS5 (each of which is not codon optimized).

One aspect of the present invention encompasses genetically modified recombinant facultative intracellular invasive bacterial pathogens (RFIIBPs), for example, a recombinant attenuated *Salmonella* vaccine (RASV) strain, capable of synthesizing ZIKV antigens. These genetically modified recombinant facultative intracellular invasive bacterial pathogens, when administered to a host, elicit an immune response against the ZIKV antigens. In particular embodiments, the genetically modified recombinant facultative intracellular invasive bacterial pathogens, for example RASV, colonize a host to substantially the same extent as a wild-type bacterium of the same serotype. The genetically modified recombinant facultative intracellular invasive bacterial pathogen is self-attenuating and becomes substantially avirulent after colonization. In certain embodiments, the recombinant facultative intracellular invasive bacterial pathogen is a recombinant attenuated *Salmonella* vaccine (RASV) strain. The RASV strains may be any *Salmonella* bacterium, such as a *Salmonella enterica* serovar, a *S. Typhimurium* strain, *S. Typhi* strain, *S. Paratyphi* A strain, *S. Gallinarum* strain, *S. Enteritidis* strain, *S. Choleraesius* strain, or *S. Dublin* strain. In an exemplary embodiment, a bacterium of the invention may be from a *S. Typhimurium* or *S. Typhi* or *S. Paratyphi* A strain. Non-limiting examples of recombinant facultative intracellular invasive bacterial pathogens include: *Legionella pneumophila; Edwardsiella* spp; *Francisella tularensis; Yersinia* spp; *Mycobacterium tuberculosis; Listeria monocyotogenes; Salmonella* spp; invasive *Escherichia coli; Neisseria* spp; *Brucella* spp; or *Shigella* spp. In particular embodiments, recombinant facultative intracellular invasive bacterial pathogen or RASV comprising vaccines with plasmids encoding synthesis of non-glycosylated ZIKV capsid (C), membrane precursor (prM), and envelope (E) proteins together or individually are provided (and can be either native ZIKV sequences or codon optimized sequences such as those provided in FIGS. 3-6). In addition, recombinant facultative intracellular invasive bacterial pathogen or RASV comprising DNA vaccines encoding synthesis of non-glycosylated proteins can contain deletion of the glycosylation sites such that the open reading frame is not altered (e.g., 3, 6, 9, 12 or more nucleotides of the DNA vaccine are deleted) or the glycosylation motif (Asn-X-Thr or Asn-X-Ser where X is any amino acid) is altered such that the Asn residue is conservatively substituted with a Gln, His, Lys or Arg residue and/or the Thr or Ser residue can be substituted with a Val or Ala residue. In preferred embodiments, the Asn residue is conservatively substituted. The recombinant facultative intracellular invasive bacterial pathogen or RASV, preferably, undergo regulated delayed lysis in the *Salmonella* containing vesicle (SCV) (or a vesicle containing the recombinant facultative intracellular invasive bacterial pathogen) and cytosol and release synthesized ZIKV antigens to induce both cellular and antibody immune responses. This can result in antibodies to one or more of the non-glycosylated proteins that will not cross-react with any of the four DENV types.

These antigens can be encoded by codon-optimized or non-codon optimized polynucleotides for expression in the RFIIBPs or RASVs (with codon-optimized sequences encoding the antigens being preferred). Polynucleotides encoding antigens that are codon-optimized or non-codon optimized can also, optionally, be engineered to contain codons that cause translational delay as discussed below. The recombinant facultative intracellular invasive bacterial pathogen or RASV comprising DNA vaccines preferably, undergo regulated delayed lysis after escape from the *Salmonella* containing vesicle (SCV) (or a vesicle containing the recombinant facultative intracellular invasive bacterial pathogen) to release the DNA vaccine encoding ZIKV antigens into the cytosol for migration to the host cell nucleus for expression of encoded ZIKV antigen genes to result in their synthesis by the immunized host. The use of codon-optimized sequences in the context of this aspect of the invention (in DNA vaccine constructs) is not necessary.

In certain embodiments, codons are optimized in the polynucleotides encoding the ZIKV antigens in a manner that enables higher levels of ZIKV antigen synthesis in the genetically modified bacterial pathogens, for example, *Salmonella*. In one embodiment, only certain codons are optimized for expression in the host bacterium while certain other codons that cause translational pauses are retained to permit protein folding of the antigens (Fluman et al., Komar et al., Kimchi-Sarfaty et al., Cortazzo et al., and Gingold et al.). The references Fluman et al., Komar et al., Kimchi-Sarfaty et al., Cortazzo et al., and Gingold et al. are incorporated by reference in their entirety.

In another embodiment, certain sequences that pause translation are introduced into the genes that encode ZIKV antigens, for example, the sequences described by Fluman et al. The sequences that pause translation can be located upstream or downstream of the codon being translated, particularly, 5-20 nucleotides upstream or downstream, preferably, 6-15 nucleotide upstream or downstream, and more preferably, 8-12 nucleotides upstream or downstream.

In a further embodiment, the sequences that pause translation are introduced into the genes that encode ZIKV antigens, for example, as described by Komar et al. Accordingly, some or all codons encoding a ZIKV antigen are replaced by rare codons that encode the same amino acids. A skilled artisan can determine rare codons in a particular organism and mutate a nucleotide sequence encoding a ZIKV antigen to produce a nucleotide sequence containing rare codons that encodes the same ZIKV antigen.

In an even further embodiment, the sequences that pause translation are introduced into the genes that encode ZIKV antigens, for example, as described by Gingold et al., particularly, as described in FIG. 3 of Gingold et al. Accordingly, genes that encode ZIKV antigens are designed to contain specific upstream and downstream sequences relative to the start codon. For example, upstream sequences up to −15 nucleotides are designed to contain specific percentage of adenine nucleotides, particularly, between 30-50%, preferably, between 35-45%, and more preferably, about 40% adenine nucleotides. Also, downstream nucleotides at +4-6 positions are adenine or thymine. Further, downstream nucleotide at +15 can preferably be thymine. The percentage of adenine nucleotides in the upstream sequence, downstream nucleotides at +4-6 positions and downstream nucleotide at +15 position can be modified as described herein in isolation or in any combination thereof.

Permitting proper folding induces antibody responses that neutralize ZIKV infection. However, certain antibodies cross reacting with DENV (based on conformational epitopes that are antigenically similar to DENV antigens) may be observed as long as the antigenicity of the conformational epitopes does not depend on post-translational modification such as glycosylation.

A further embodiment of the invention provides polynucleotides that encode ZIKV antigens that decrease or prevent the recombinant antigens synthesized by the genetically modified bacterial pathogens of the invention, for example, RFIIBPs or RASVs, from folding into secondary structures. As noted above, folding of ZIKV antigens can induce antibodies to conformational epitopes present in the ZIKV antigens folded into secondary structures. Therefore, preventing folding of ZIKV antigens reduce induction of cross reactive antibodies to conformational epitopes that may be similar in antigens from various flaviviruses such as ZIKV and DENV.

Accordingly, an embodiment of the invention provides polynucleotides that encode linear ZIKV antigens, i.e., ZIKV antigens containing linear epitopes. The ZIKV antigens encoded by such polynucleotides do not fold into ZIKV antigens having secondary structures. Therefore, the linear ZIKV antigens of the invention induce high antibody titers that neutralize ZIKV to prevent infection; however, since the linear ZIKV antigens do not fold into antigens having secondary structures, the ZIKV linear antigens do not induce cross reacting antibodies that may be induced by conformational epitopes of the folded ZIKV antigens. Also, since the linear ZIKV antigens do not fold into antigens having secondary structures, the linear ZIKV antigens are secreted from the genetically modified bacterial pathogens without the need for chaperons. In one embodiment, two of the ZIKV surface antigens (prM and E) known to induce cross reactive antibodies were modified to produce polynucleotides that encode linear ZIKV antigens that do not exhibit protein folding.

In one embodiment, the polynucleotides that encode for ZIKV antigens containing linear epitopes, all the codons are optimized for expression in the host bacterium to allow robust expression of the antigens in the genetically modified bacterial pathogens, for example, *Salmonella*. Having all the codons optimized for expression prevents the pauses in translation due to scarcity of charged tRNA species and thus, accelerates translation. Accelerated translation precludes folding of the antigens and enhances secretion of antigens fused to a type II secretion sequence, which causes induction of antibodies that do not recognize conformational epitopes on ZIKV and that neutralize ZIKV infection. The antibodies induced by the linear ZIKV antigens do not cross react with other flaviviruses, especially DENV because of the lack of conformational similarity between the linear ZIKV antigens described herein and DENV antigens having conformational epitopes.

Figure 1B:
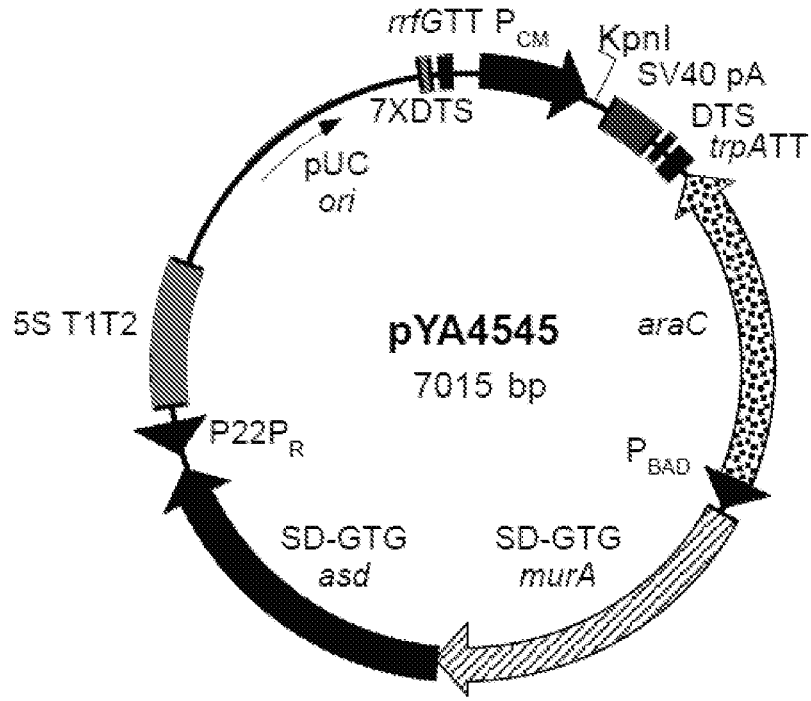
Figure 1C:
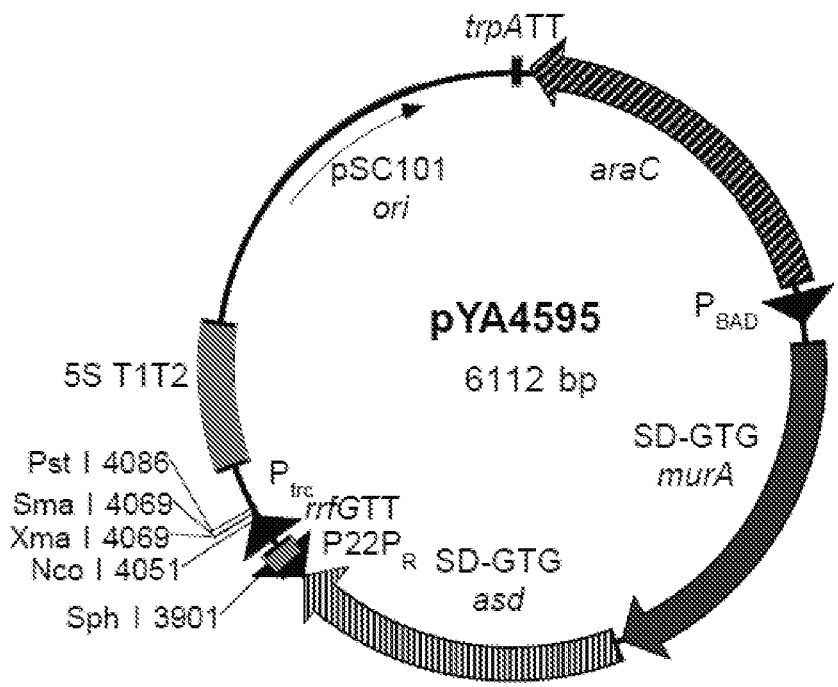
Figure 1D:
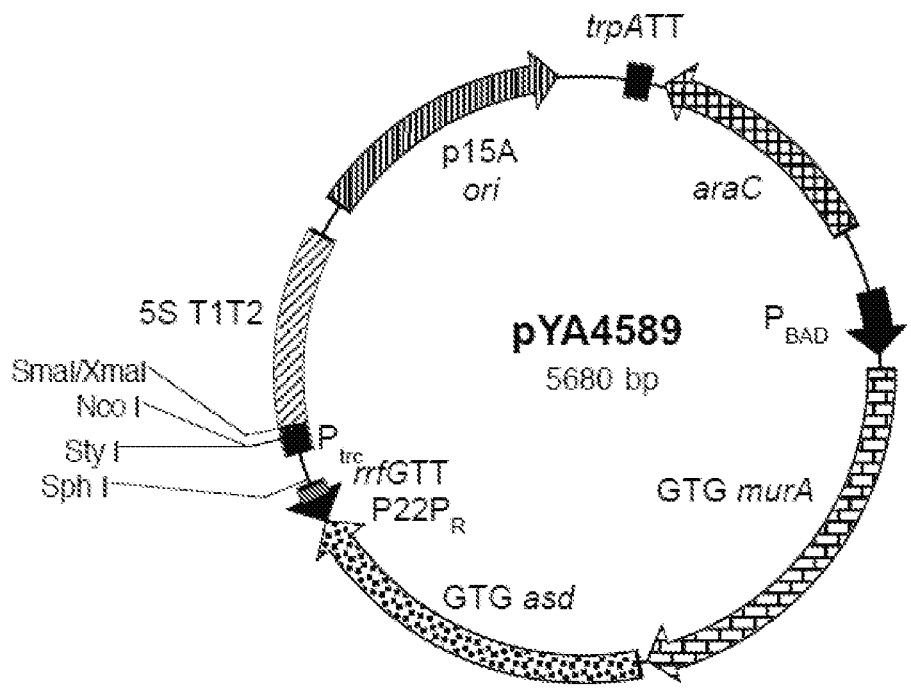
Figure 1E:
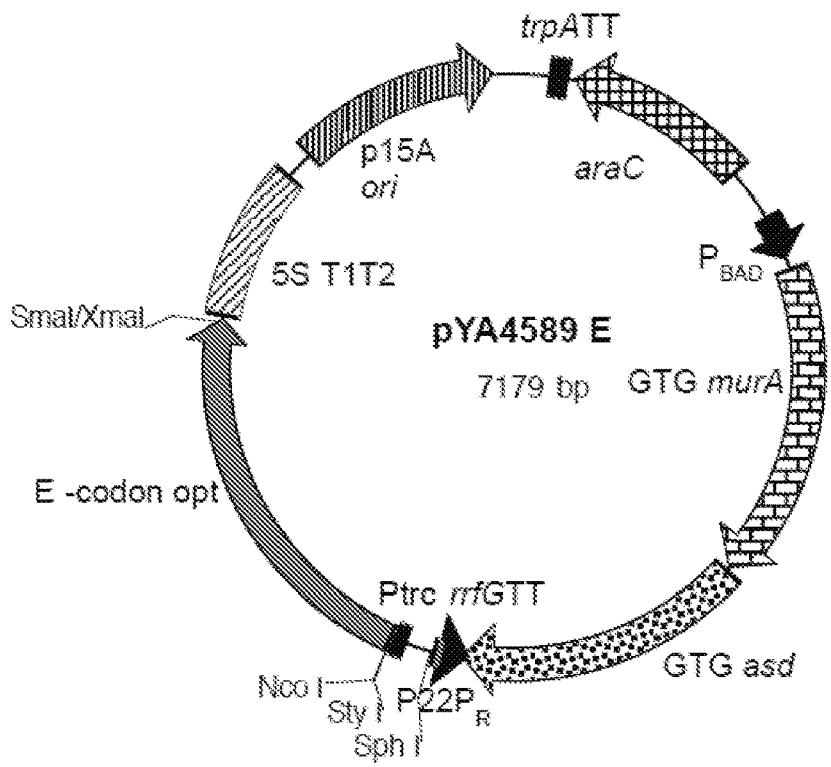
Figure 1F:
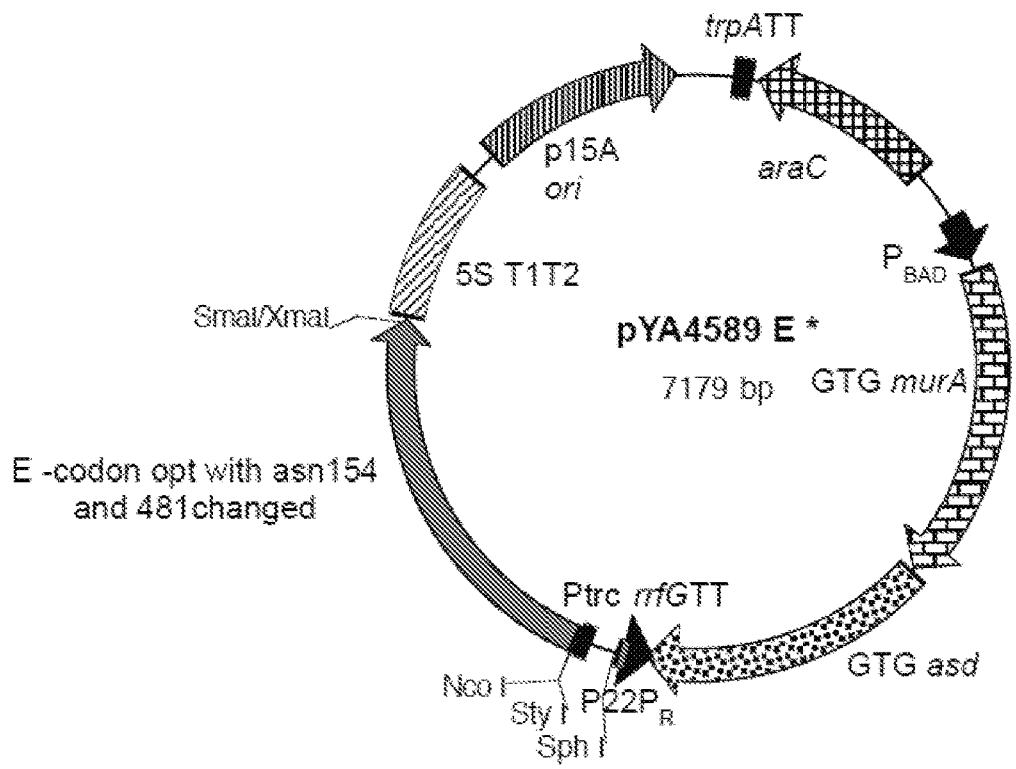
Figure 1G:
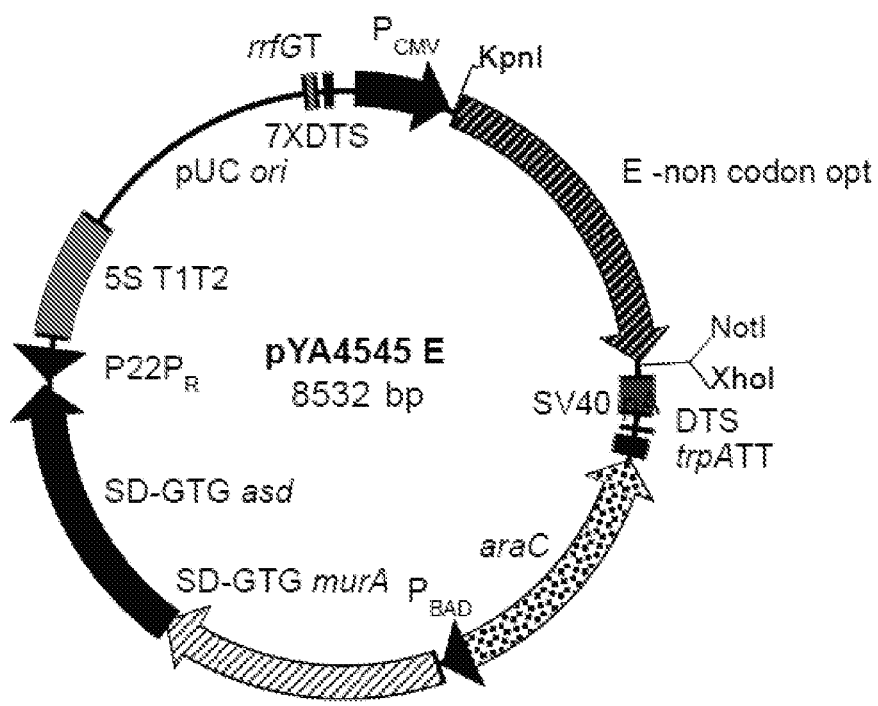
Figure 1H:
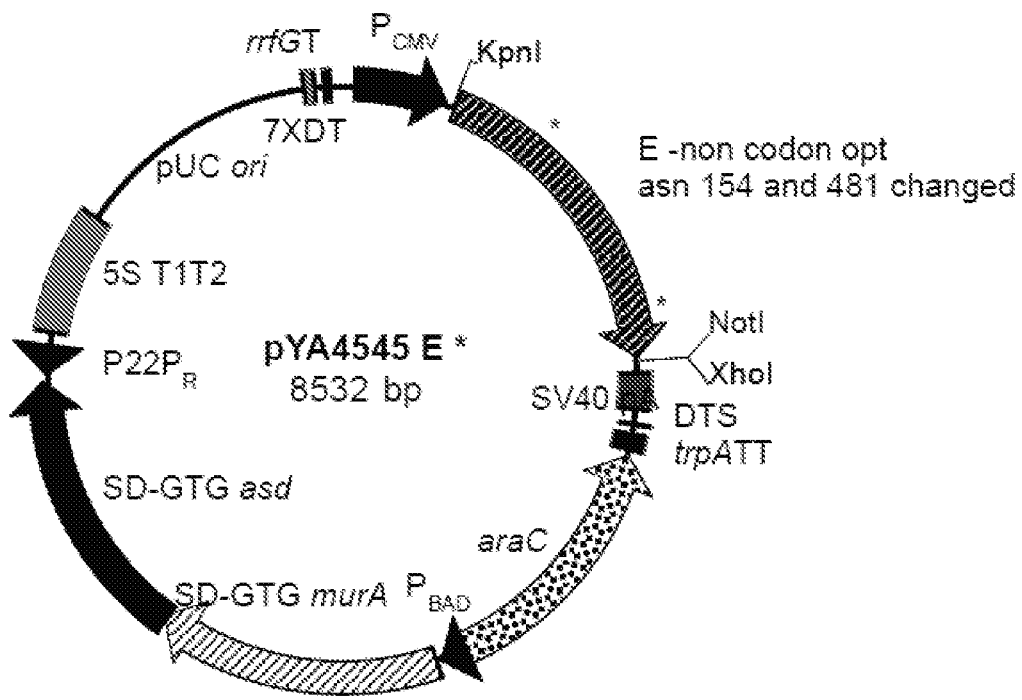
Figure 1I:
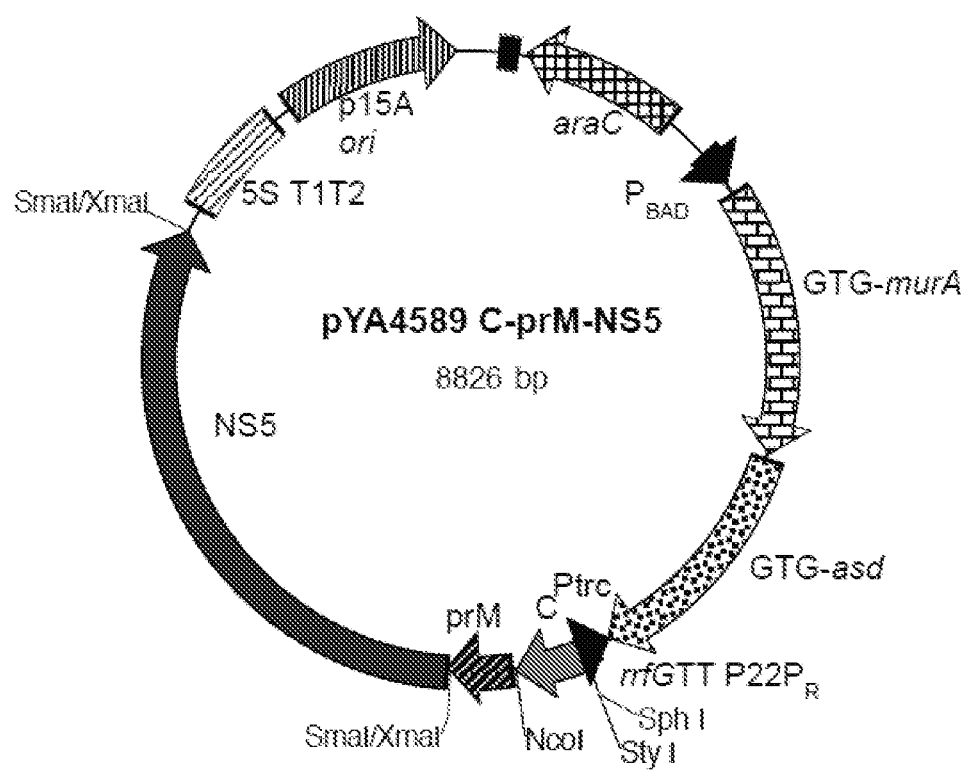
Figure 2:
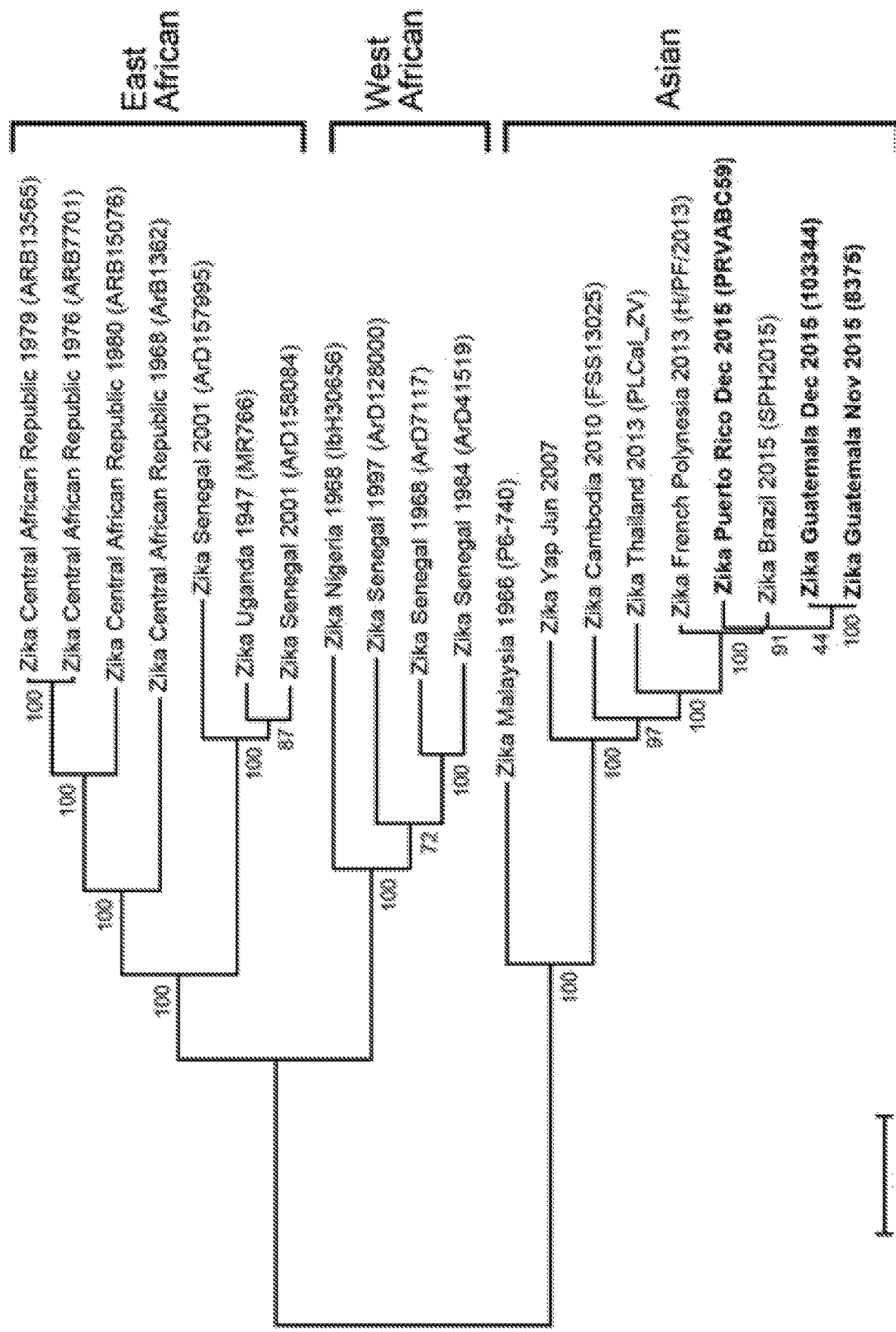
FIG. 2. Phylogenetic tree of Zika virus isolates identified from Guatemala and Puerto Rico in December 2015 (indicated in boldface) compared with reference isolates obtained from GenBank. The isolates from Guatemala and Puerto Rico grouped with other Asian genotype viruses. The tree was derived by neighbor-joining methods (bootstrapped 1,000 times) using complete-genome sequences. Location, year identified, and GenBank strain identification for the viruses used in tree construction are shown. Scale bar indicates number of nucleotide substitutions per site. GenBank accession nos.: KU321639 (Brazil 2015 SPH2015), KJ776791 (French Polynesia H/PF/2013), KF383115 (Central African Republic ARB1362), KF383116 (Senegal 1968 ArD7117), KF383117 (Senegal 1997 ArD128000), KF383118 (Senegal 2001 ArD157995), KF383119 (Senegal 2001 ArD158084), KF268948 (CAR 1979 ARB13565), KF268949 (CAR 1980 ARB15076), KF268950 (CAR 1976 ARB7701), EU545988 (Yap 2007), KF993678 (Thailand 2013 PLCal_ZV), JN860885 (Cambodia 2010 FSS13025), HQ234499 (Malaysia 1966 P6-740), HQ234501 (Senegal 1984 ArD41519), HQ234500 (Nigeria 1968 IbH 30656), LC002520 (Uganda 1947 MR766), KU501215 (Puerto Rico PRVABC59), KU501216 (Guatemala 8375), and KU501217 (Guatemala 103344) [published by Lanciotti R S, Lambert A J, Holodniy M, Saavedra S, Signor Ldel C., 2016, Phylogeny of Zika Virus in Western Hemisphere, 2015. Emerg Infect Dis. 22(5):933-5)].
Figure 8:
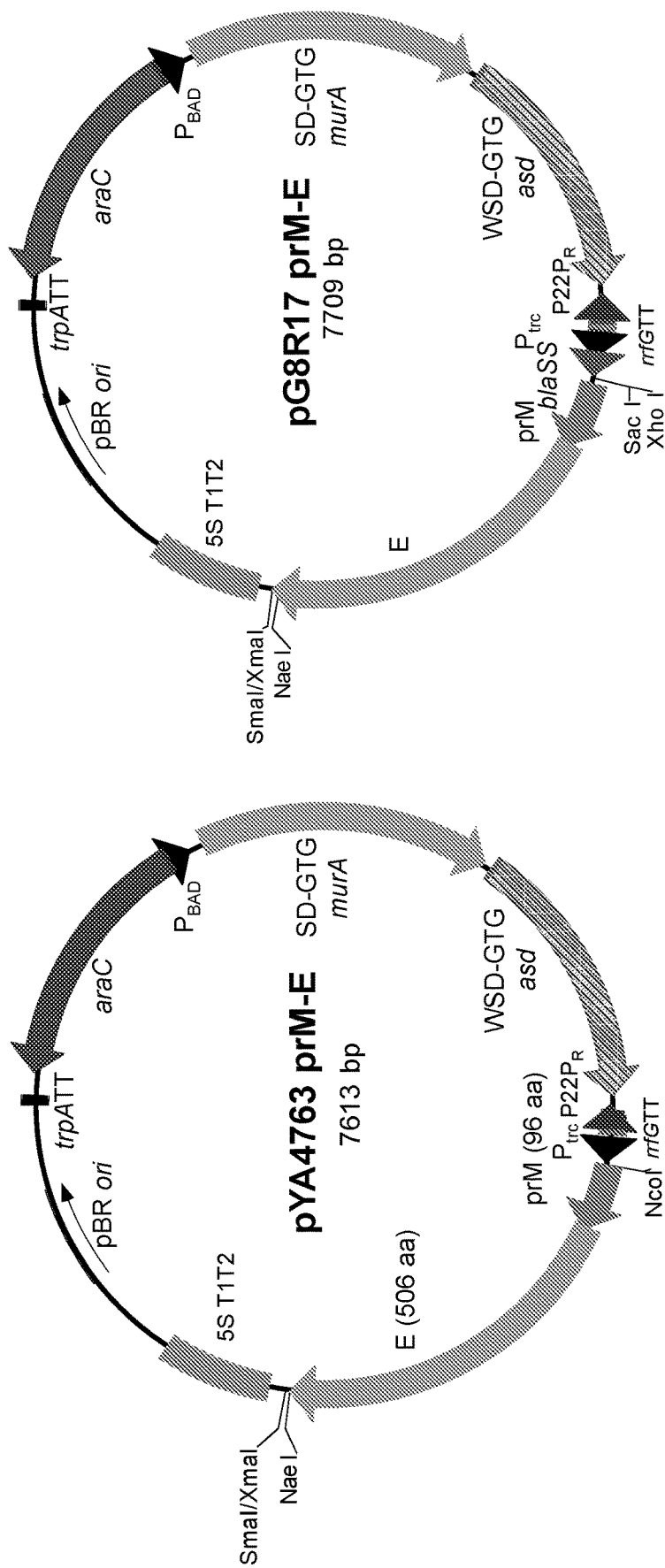
FIG. 8. Plasmid maps for pYA4763 prM-E and pG8R17 prM-E. ZIKV prM and E proteins encoded by sequences with codons most frequently used in highly expressed *Salmonella* genes as given for the DNA sequences listed on line 2 in FIGS. 10A and 10B.
Figure 9:
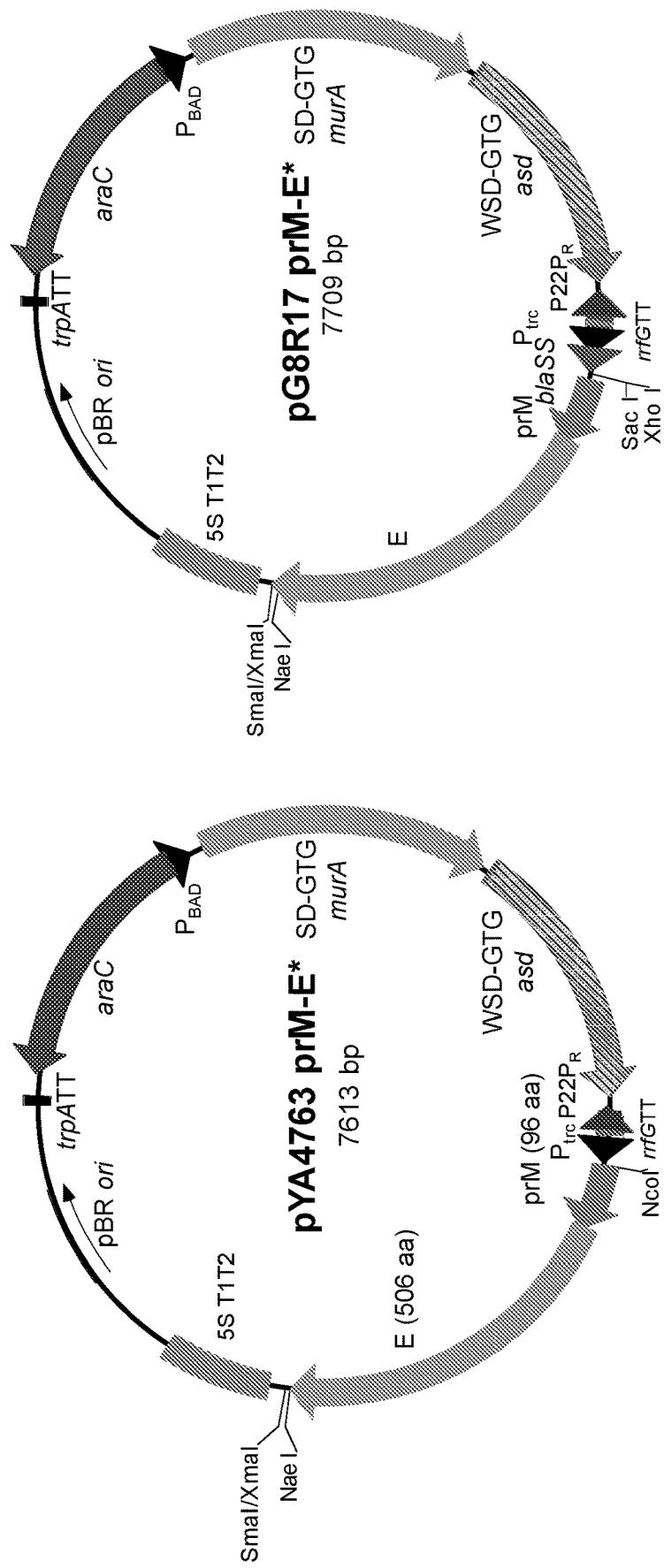
FIG. 9. prM-E vector maps for pYA4763 prM-E* and pG8R17 prM-E*. ZIKV prM and E proteins encoded by sequences with codons most frequently used in the most highly expressed *Salmonella* genes as given for the DNA sequences listed on line 3 in FIGS. 10A and 10B with *Salmonella*-synthesized proteins retained in RASV cells for release during regulated delayed lysis (pYA4763-derived construct) or continually secreted due to fusion to the type 2 secretion system β-lactamase into the RASV periplasm to generate outer membrane vesicles and also continually released extracellularly to augment induction of immune responses prior to a release of a bolus of antigens at the time of regulated lysis in vivo (pG8R17-derived construct).

In one embodiment, polynucleotides that encode for ZIKV antigens are provided, wherein the polynucleotides have all codons or a majority of codons changed to represent the most highly used codon (or two or more highly used codons) in the host bacterium for each amino acid. The "majority of codons" as used herein, refer to at least 80% to at least 99% of codons, particularly, at least 85% to 95% of codons, and more particularly, at least 90% of codons. These sequences encode mRNAs that are translated very rapidly into antigens that will not fold as they would during ZIKV maturation (see, for example, FIGS. 10A and 1B). These antigens induce antibodies with high specificity to ZIKV and low reactivity with other flaviviruses. These antigens also exhibit enhanced secretion when combined with an improved β-lactamase signal sequence. In a particular embodiment, all codons or a majority of codons are changed to represent the most highly used codon (or codons) for highly expressed genes in Salmonella.

In other aspects, the subject application provides a recombinant facultative intracellular invasive bacterial pathogen or RASV comprising a DNA vaccine encoding a modified E sequence that induces neutralizing antibodies against ZIKV that should not cross-react with DENV. In some embodiments, the DNA vaccine contains an envelope (E) sequence wherein the 154 bp fragment that encodes the glycosylation motif, which is associated with virulence, has been deleted. Alternatively, the DNA vaccine can encode an E sequence that contains an altered glycosylation motif (Asn-X-Thr or Asn-X-Ser where X is any amino acid) such that glycosylation of the E sequence does not occur. For example, the Asn and/or Thr residue can be conservatively substituted with an amino acid as set forth in Table 1. For example, the Asn residue can be substituted with a Gln, His, Lys or Arg residue and/or the Thr or Ser residue can be substituted with an Ala or a Val residue. The Thr or Ser residue can, alternatively, be substituted with a Gly residue. In preferred embodiments, the Asn residue is conservatively substituted. Alternatively, the DNA vaccines contain deletion of the glycosylation sites such that the open reading frame is not altered (e.g., 3, 6, 9, 12 or more nucleotides of the DNA vaccine are deleted). The recombinant facultative intracellular invasive bacterial pathogen or RASV, preferably, undergo regulated delayed lysis in the SCV and cytosol and induce both cellular and antibody immune responses will likely yield antibodies to one or more of the non-glycosylated proteins that will not cross-react with any of the four DENV types.

Yet other embodiments provide for recombinant facultative intracellular invasive bacterial pathogens or RASV that synthesize other ZIKV antigens. These ZIKV antigens can be synthesized, either individually or in combination, by the RASV disclosed herein and can be native or codon optimized sequences (such as those in FIGS. 3-6). These include: NS1, NS2A, NS2B, NS3, NS4A, 2K, NS4B, NS5 or fusion proteins comprising two or more of these antigens. For example, a ZIKV polyfusion protein comprising NS1-NS2A-NS2B-NS3 or ZIKV NS4A-2K-NS4B-NS5 can be synthesized by the disclosed RASV or recombinant facultative intracellular invasive bacterial pathogen. Alternatively, individual antigens can be synthesized on individual plasmids or in a single plasmid under the control of a single promoter or separate promoters.

RFIIBPs and/or RASVs disclosed herein can be constructed using the teachings of this application and those of, for example, U.S. Patent Application Publication 2013/0171190A1 and U.S. Patent Application Publication 2012/0087946A1, each of which is hereby incorporated by reference in its entirety. Additional teachings can be found in the following references, each of which is also hereby incorporated by reference in its entirety: AMEISS, K. et al. "Delivery of woodchuck hepatitis virus-like particle presented influenza M2e by recombinant attenuated Salmonella displaying a delayed lysis phenotype" Vaccine, 2010, pp. 6704-6713, Vol. 28; ASHRAF, S. et al. "Protective cellular responses elicited by vaccination with influenza nucleoprotein delivered by a live recombinant attenuated Salmonella vaccine" Vaccine, 2011, pp. 3990-4002, Vol. 29; CURTISS, R. et al. "New Technologies in Using Recombinant Attenuated Salmonella Vaccine Vectors" Critical Reviews™ in Immunology, 2010, pp. 255-270, Vol. 30, No. 3; CURTISS, R. et al. "NONRECOMBINANT AND RECOMBINANT A VIRULENT SALMONELLA LIVE VACCINES FOR POULTRY" Colonization Control of Human Bacterial Enteropathogens in Poultry, 1991, pp. 169-198; JUÁREZ-RODRÍGUEZ, M. D. et al. "Live Attenuated Salmonella Vaccines against Mycobacterium tuberculosis with Antigen Delivery via the Type III Secretion System" Infect. Immun., 2012, pp. 798-814, Vol. 80, No. 2; KONG, W. et al. "Regulated programmed lysis of recombinant Salmonella in host tissues to release protective antigens and confer biological containment" Proceedings of the National Academy of Sciences of the United States of America, Jul. 8, 2008, pp. 9361-9366, Vol. 105, No. 27; KONG, W. et al. "Turning self-destructing Salmonella into a universal DNA vaccine delivery platform" Proceedings of the National Academy of Sciences of the United States of America, Oct. 11, 2012, pp. 1-13; KONG, W. et al. "Utilizing Salmonella for antigen delivery: the aims and benefits of bacterial delivered vaccination" Expert Rev. Vaccines, 2013, pp. 345-347, Vol. 12, No. 4; WANG, S. et al. "New technologies in developing recombinant attenuated Salmonella vaccine vectors" Microbial Pathogenesis, 2013, pp. 17-28, Vol. 58; and JIANG, Y. et al. "Protection Against Necrotic Enteritis in Broiler Chickens by Regulated Delayed Lysis Salmonella Vaccines" Avian Diseases, 2015, pp. 475-485, Vol. 59.

The RFIIBPs or RASVs disclosed herein contain one or more vectors, preferably one vector, that manipulates the ability of the RFIIBPs or RASVs to synthesize various essential constituents needed for synthesis of the rigid peptidoglycan layer of its cell wall (exemplary vector maps are provided in FIG. 1 and, as one skilled in the art would recognize, the base vectors can be modified to contain a DNA sequence encoding an antigen of interest that is to be synthesized by the RFIIBPs or RASVs disclosed herein). The plasmids illustrated in FIG. 1 have identical selective markers that permit a single vector to be stably maintained in the RASV at any given time. Where additional vectors are contemplated for use in the disclosed RFIIBPs or RASVs, one can introduce Δalr and ΔdadB mutations and use vectors containing a dadB+ gene. This produces a second balanced-lethal vector system based on the required need for D-alanine for peptidoglycan synthesis. It should also be noted that, some of the lysis vectors in FIG. 1 (specifically FIGS. 1A, 1C and 1D) are designed with a bacterial promoter $P_{trc}$ to enable expression of inserted coding sequences and synthesis of the antigen by Salmonella to be delivered to the host. In contract, the vector in FIG. 1B is a DNA vaccine vector with a eukaryotic promoter $P_{CMV}$ so that inserted genes are expressed in the eukaryotic host cells. The vectors in FIGS. 1E, 1F and 1I are, therefore plasmids that cause synthesis of the antigens by the RASV or RFIIBPs whereas the vectors in FIGS. 1G and 1H specify antigens to be synthesized by the immunized host.

In one example, the constituent is diaminopimelic acid (DAP) and or muramic acid. Various enzymes are involved in the eventual synthesis of DAP. In one example, the RFIIBPs or RASVs are modified by using a ΔasdA mutation to eliminate the ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asdA. The disclosed RFIIBPs or RASVs may comprise (or further comprise) a genetic modification such that the synthesis of another essential constituent of the rigid layer of the bacterial cell wall is dependent on a nutrient (e.g., arabinose) that can be supplied during the growth of the microorganism. However, when arabinose is absent as it is in an animal or human host, the essential constituents of the peptidoglycan layer of the cell wall are not synthesized. These mutations represent an arabinose dependent lethal mutation. In the absence of arabinose, synthesis of muramic acid and DAP ceases and lysis of the RFIIBPs or RASVs occurs because the peptidoglycan layer of the cell wall is not synthesized. RFIIBPs or RASVs with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid. Similarly, various embodiments may comprise the araC $P_{BAD}$ c2 cassette inserted into the asdA nucleic acid sequence that encodes aspartate semialdehyde dehydrogenase in RFIIBPs or RASVs or deletion/inactivation of the chromosomal asdA gene encoding aspartate semialdehyde dehydrogenase to enable use of plasmid vectors encoding the wild-type asdA nucleic acid sequence.

In some embodiments, the promoter may be responsive to the level of arabinose in the environment, as described above. In other embodiments, the promoter may be responsive to the level of maltose, mannose, rhamnose, or xylose in the environment, as described above. The promoters detailed herein are known in the art, and methods of operably linking them to a nucleic acid sequence encoding an attenuation protein are known in the art. Generally speaking, the concentration of arabinose, maltose, mannose, rhamnose, or xylose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%.

RFIIBPs or RASVs may, optionally, comprise further genetic modifications. For example, the gene encoding phosphomannose isomerase may be deleted or inactivated in RFIIBPs or RASVs. Alternatively, the gene encoding O-antigen ligase (waaL) can be deleted or inactivated. Similarly, additional genetic alterations, such as inactivation or deletion of one or more of the following genes can be performed on the disclosed RFIIBPs or RASVs: relA, wza-wcaM, sifA, recF, recJ, sseL, tlpA, msbB and pagP. RFIIBPs or RASVs disclosed herein can also be genetically modified to synthesize the non-toxic adjuvant form of LPS, lipid A monophosphoryl lipid A (MPLA) by introduction of a lpxE gene that is operably linked to a repressor sensitive promoter which facilitates delayed in vivo synthesis of MPLA by the RFIIBPs or RASVs. RFIIBPs or RASVs are capable of the regulated expression of at least one nucleic acid sequence and comprise a vector. The vector comprises a nucleic acid sequence encoding at least one antigen of interest operably linked to a promoter. The promoter is regulated by a repressor, such that the expression of the nucleic acid sequence encoding a least one flavivirus antigen (e.g., a ZIKV antigen) is repressed during in vitro growth of the RFIIBPs or RASVs, but the RFIIBPs or RASVs are capable of high level synthesis of the antigen in an animal or human host. Other genetic modifications include genetic modification of Shine Dalgarno sequences and/or the introduction of GTG start codons such that translational efficiency of mRNA synthesized by the RFIIBPs or RASVs is decreased (see, for example, U.S. Patent Application Publication 2013/0171190A1 and U.S. Patent Application Publication 2012/0087946A1 each of which is hereby incorporated by reference in this regard).

As used herein, "vector" refers to an autonomously replicating nucleic acid unit. The most preferred type of vector is a plasmid vector with examples illustrated in FIG. 1. As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector.

In some instances in which the flavivirus antigen is capable of stimulating T-cell immunity, it may be preferable to use a vector with a low copy number such as at least two, three, four, five, six, seven, eight, nine, or ten copies per cell. A non-limiting example of a low copy number vector may be a vector comprising the pSC101 ori. In other cases, an intermediate copy number vector might be optimal for inducing a desired immune response. For instance, an intermediate copy number vector may have at least 10, 11, 12, 13, 14, 15, 16, 17, 18, 19, 20, 21, 22, 23, 24, 25, 26, 27, 28, 29, or 30 copies per cell. A non-limiting example of an intermediate copy number vector may be a vector comprising the p15A ori. In still other cases, a high copy number vector might be optimal for the induction of maximal antibody response to a flavivirus antigen (e.g., a ZIKV antigen). A high copy number vector may have at least 31, 35, 40, 45, 50, 55, 60, 65, 70, 75, 80, 85, 90, 95, or 100 copies per cell. In some embodiments, a high copy number vector may have at least 100, 125, 150, 175, 200, 225, 250, 275, 300, 325, 350, 375, or 400 copies per cell. Non-limiting examples of high copy number vectors may include a vector comprising the pBR ori or the pUC ori. Additionally, vector copy number may be increased by selecting for mutations that increase plasmid copy number. These mutations may occur in the bacterial chromosome but are more likely to occur in the plasmid vector. Preferably, vectors used herein do not comprise antibiotic resistance markers to select for maintenance of the vector.

The vector may comprise a nucleic acid sequence encoding at least one flavivirus antigen (preferably a ZIKV antigen) operably-linked to a promoter regulated by the repressor. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the flavivirus (e.g., ZIKV) antigen, such that expression of the nucleic acid sequence encoding an antigen is repressed when the repressor is synthesized (i.e. during in vitro growth of the RFIIBPs or RASVs), but expression of the nucleic acid sequence encoding a flavivirus (e.g., ZIKV) antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding a flavivirus (e.g., ZIKV) antigen after about 2, 3, 4, 5, 6, 7, 8, 9, 10, 11, or 12 divisions of the RFIIBPs or RASVs. In an exemplary embodiment, the concentration of the repressor decreases enough to allow high level expression of the nucleic acid sequence encoding an antigen after about 5 divisions of the RFIIBPs or RASVs in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO. In one embodiment, the repressor is a LacI repressor and the promoter is $P_{trc}$.

As detailed above, generally speaking the expression of the nucleic acid sequence encoding the antigen should be repressed when the repressor is synthesized. For instance, if the repressor is synthesized during in vitro growth of the RFIIBPs or RASVs, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute. Conversely, the expression of the nucleic acid sequence encoding the antigen should be high when the expression of the nucleic acid sequence encoding the repressor is repressed. For instance, if the nucleic acid sequence encoding the repressor is not expressed during growth of the RFIIBPs or RASVs in the host, the expression of the nucleic acid sequence encoding the antigen should be high. As used herein, "high level" expression refers to expression that is strong enough to elicit an immune response to the flavivirus (e.g., ZIKV) antigen. Methods of determining whether an antigen elicits an immune response such as by measuring antibody levels or antigen-dependent T cell populations or antigen-dependent cytokine levels are known in the art, and methods of measuring levels of expression of flavivirus (e.g., ZIKV) antigen encoding sequences by measuring levels of mRNA transcribed or by quantitating the level of antigen synthesis are also known in the art.

As discussed above, the disclosed recombinant facultative intracellular invasive bacterial pathogen or RASV can deliver synthesized ZIKV antigens specified by plasmids such as derivatives of pYA4763, pYA4589 and pYA4595 depicted in FIG. 1 and introduced into S. Typhimurium strain χ11829 ($\Delta P_{murA25}$::TT araC $P_{BAD}$ murA $\Delta$asdA27::TT araC $P_{BAD}$ c2 $\Delta$pmi-2426 $\Delta$(wza-wcaM)-8 $\Delta$relA197::araC $P_{BAD}$ lacI TT $\Delta$recF126 $\Delta$sifA26) that possesses the regulated delayed antigen synthesis attribute and the regulated delayed lysis attribute. This strain also possesses the $\Delta$sifA mutation so that lysis occurs in the cytosol to release synthesized ZIKV antigens for presentation to the proteasome for ultimate class I presentation to enhance induction of CD8- and CD17-dependent cellular immunities.

As discussed above, the disclosed recombinant facultative intracellular invasive bacterial pathogen or RASV can deliver DNA vaccines using vectors, such as derivatives of pYA4545 which are illustrated in FIG. 1. Methods for constructing such DNA vaccines (as well as plasmids for delivering DNA vaccines) are described in Kong et al., 2012, Proc. Nat'l. Acad. Sci. USA, 109(47):19414-19419 (the disclosure of which is hereby incorporated by reference in its entirety). For example, specific embodiments provide RASV containing the following genetic modifications that can be used to deliver the DNA vaccines: (($\Delta P_{murA}$::TT araC $P_{BAD}$ murA; $\Delta$asdA::TT araC $P_{BAD}$ c2; $\Delta$(wza-wcaM) $\Delta$pmi $\Delta$relA $\Delta$recF $\Delta$endA $\Delta$sseL $\Delta$tlpA $\Delta P_{hilA}$::$P_{trc\Delta lacO}$ hilA) and $\Delta P_{murA}$::TT araC $P_{BAD}$ murA $\Delta$asdA::TT araC $P_{BAD}$ c2 $\Delta$pmi $\Delta$waaL $\Delta$pagL:TT rhaRS $P_{rhaBAD}$ waaL $\Delta$(wza-wcaM) $\Delta$relA $\Delta$endA $\Delta$sseL $\Delta$tlpA $\Delta$recF $\Delta$sifA. In some embodiments, the RASV are S. Typhimurium strains χ11848 (($\Delta P_{murA}$::TT araC $P_{BAD}$ murA; $\Delta$asdA::TT araC $P_{BAD}$ c2; $\Delta$(wza-wcaM) $\Delta$pmi $\Delta$relA $\Delta$recF $\Delta$endA $\Delta$sseL $\Delta$tlpA $\Delta P_{hilA}$::$P_{trc\ \Delta lacO}$hilA) and χ12386 $\Delta P_{murA}$::TT araC $P_{BAD}$ murA $\Delta$asdA::TT araC $P_{BAD}$ c2 $\Delta$pmi $\Delta$waaL $\Delta$pagL:TT rhaRS $P_{rhaBAD}$ waaL $\Delta$(wza-wcaM) $\Delta$relA $\Delta$endA $\Delta$sseL $\Delta$tlpA $\Delta$recF $\Delta$sifA.

In certain additional aspects of the application, a vaccine comprising the disclosed recombinant facultative intracellular invasive bacterial pathogens or RASV are provided. The disclosed recombinant facultative intracellular invasive bacterial pathogens or RASV can be administered to a host as a vaccine composition that is designed to induce an immune response to the antigens being delivered by the RASV. As discussed above, the subject application envisions induction of an immune response that is protective and generation of antibodies that react with ZIKV antigens but which do not substantially cross react with DENV antigens. As used herein, "protective" means that the immune response contributes to the lessening of any symptoms associated with infection of a host with ZIKV and need not imply that the immunized host is completely protected from the effects of the ZIKV. In certain embodiments, the vaccine is orally administered and induces protective mucosal immunity in the host (e.g., the mucosal immunity decreases the infectivity of ZIKV in bodily secretions). Vaccine compositions of the present invention may be administered to any host capable of mounting an immune response. Such hosts may include domesticated animals, agricultural animals, laboratory animals, and humans. A vaccine composition comprising a recombinant facultative intracellular invasive bacterial pathogen or RASV may, optionally, contain one or more additional components, such as carriers, preservatives, stabilizers, adjuvants, and other substances. In another embodiment, the vaccine composition may also contain a pharmaceutical carrier (or excipient). Carriers and excipients as well as formulations for parenteral and non-parenteral drug delivery are set forth in Remington's Pharmaceutical Sciences 19th Ed. Mack Publishing (1995).

Various embodiments contemplate the oral administration of the disclosed vaccine compositions. Typical dosages for oral administration can range from about $1 \times 10^7$ to $1 \times 10^{10}$ CFU. Administering multiple dosages may also be used as needed to provide the desired level of protective immunity.

In order to stimulate an immune response, the disclosed recombinant facultative intracellular invasive bacterial pathogens or RASV compositions can be administered on mucosal surfaces, such as orally or intranasally (as a liquid or aerosol). Where the disclosed RASV are administered to humans, oral administration is preferred.

A further aspect of the invention encompasses methods of using the disclosed recombinant facultative intracellular invasive bacterial pathogens or RASV disclosed herein for inducing an immune response specific to ZIKV in a host. The method comprises administering an effective amount of a composition comprising a recombinant facultative intracellular invasive bacterial pathogen or a RASV disclosed herein to a host. An effective amount of a composition comprising a recombinant facultative intracellular invasive bacterial pathogen or a RASV as disclosed herein is an amount that will generate the desired immune response (e.g., mucosal, humoral and/or cellular) to ZIKV antigens synthesized by the RASV or the recombinant facultative intracellular invasive bacterial pathogen. Methods of monitoring a host's immune response are well-known to those skilled in the art and non-limiting examples include ELISA and ELISPOT assays. In particular embodiments, the antibodies induced by the disclosed RASV are not substantially cross reactive with, or does not substantially bind to, similar antigens from other flaviviruses, for example DENV.

The phrase "neutralizing antibodies against ZIKV that do not cross-react with DENV" is intended to convey that the antibodies neutralize the ability of ZIKV to initiate and/or cause an infection in a host and/or in target cells in vitro; however, these antibodies have no significant effect on the ability of DENV to initiate or cause an infection in a host and/or in target cells in vitro. Likewise, the phrases "not substantially cross reactive with", or "does not substantially bind to" similar antigens from other flaviviruses (such as any of the four DENV types) is intended to convey that the antibodies have the ability to neutralize the ability of ZIKV to initiate and/or cause an infection in a host and/or in target cells in vitro; however, these antibodies have no significant effect on the ability of any of the four DENV types to initiate or cause an infection in a host and/or in target cells in vitro. For example, standard ZIKV or DENV plaque-reduction-neutralization tests can be used to determine if neutralizing antibodies to ZIKV antigens neutralize DENV infectivity in a host cell or a target cell.

The phrase "ZIKV protein antigens that may, optionally, be encoded by codon optimized nucleotide sequences and/or engineered for translational acceleration or delay" is meant to include the use of non-codon optimized nucleotide sequences encoding ZIKV protein antigens, the use of codon optimized nucleotide sequences encoding ZIKV antigens, the use of nucleotide sequences that are engineered for translational delay, the use of nucleotide sequences that are engineered for translational acceleration, or any combination of such nucleotide sequences that encode ZIKV protein antigens.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods

Vaccine vector strains. *S. Typhimurium* strains will be used to synthesize and deliver non-structural and non-glycosylated surface proteins to immunized animal hosts. $\chi 11829$ ($\Delta P_{murA}$::TT araC $P_{BAD}$ murA; $\Delta$asdA::TT araC $P_{BAD}$ c2 $\Delta$pmi; $\Delta$(wza-wcaM) $\Delta$relA::araC $P_{BAD}$ lacI TT; $\Delta$recF $\Delta$sifA) and $\times 12341 \Delta P_{murA}$::TT araC $P_{BAD}$ murA $\Delta$asdA::TT araC $P_{BAD}$ c2 $\Delta$pmi $\Delta$waaL $\Delta$pagL::TT rhaRS $P_{rhaBAD}$ waaL $\Delta$(wza-wcaM) $\Delta$relA::araC $P_{BAD}$ lacI TT $\Delta$recF $\Delta$sifA. Two other strains will be used for delivery of DNA vaccine vectors encoding ZIKV surface proteins encoded by sequences modified to eliminate post-translational glycosylation of surface proteins synthesized within the immunized animal host. $\chi 11848$ (($\Delta P_{murA}$::TT araC $P_{BAD}$ murA; $\Delta$asdA::TT araC $P_{BAD}$ c2; $\Delta$(wza-wcaM) $\Delta$pmi $\Delta$relA $\Delta$recF $\Delta$endA $\Delta$sseL $\Delta$tlpA $\Delta P_{hilA}$::$P_{trc}$ $_{\Delta lacO}$hilA) and $\chi 12386$ $\Delta P_{murA}$::TT araC $P_{BAD}$ murA $\Delta$asdA::TT araC $P_{BAD}$ c2 $\Delta$pmi $\Delta$waaL $\Delta$pagL::TT rhaRS $P_{rhaBAD}$ waaL $\Delta$(wza-wcaM) $\Delta$relA $\Delta$endA $\Delta$sseL $\Delta$tlpA $\Delta$recF $\Delta$sifA have been constructed. Both of these RASV have a regulatable in vivo delayed lysis phenotype and escape the SCV to lyse in the cytosol to deliver antigens to the proteosome for MHC class I presentation or DNA vaccine vectors encoding antigens, respectively. The delivery of synthesized antigens to the proteosome induces CD8-, CD17- and NKT-dependent immune responses. The RASV strain $\chi 11848$ can be used to deliver DNA vaccines encoding protective antigens to the nucleus of host cells for transcription. *S. Typhi* strains of the same genotypes for use in human vaccines will be generated. These strains will include a $\Delta$pagP::$P_{trc}$ lpxE mutation specifying synthesis of non-toxic adjuvant monophosphoryl lipid A. See KONG, Q. et al, "*Salmonella* Synthesizing 1-Monophosphorylated Lipopolysaccharide Exhibits Low Endotoxic Activity while Retaining Its Immunogenicity" *The Journal of Immunology*, 2011, pp. 412-423, Vol. 187.

Plasmid Vectors.

All plasmids to be used confer the regulated delayed lysis in vivo phenotype and employ the balanced-lethal vector-host concept to ensure that live RASVs would be sensitive to all antibiotics and thus unable to disseminate antibiotic resistance when RASVs were used in open agricultural settings. The regulated lysis vectors depicted in FIGS. 1A, 1C, 1D-1F and 1I all have $P_{trc}$ regulated synthesis of protective antigens for delivery by cell lysis and araC $P_{BAD}$ regulated murA and asd genes with GTG start codons to decrease translation efficiency. Certain of these vectors also contain modified Shine Dalgarno sequences that also affect translational efficiency (e.g., FIG. 1C). The P22 $P_R$ located with opposite orientation to the transcription of the araC $P_{BAD}$ GTG-murA GTG-asd genes is repressed by the C2 repressor made during growth of the strain with arabinose. However, C2 concentration decreases due to cell division in vivo to cause $P_R$-directed anti-sense mRNA synthesis to block translation of residual asdA and murA mRNA. Transcription terminators (TT) flank all plasmid domains for controlled lysis, replication and gene expression so that expression in one domain does not affect activities of another domain.

Bacterial Strains, Media and Bacterial Growth.

All RASVs are derived from the highly virulent *S. Typhimurium* strain UK-1 (Curtiss et al., 1991) that are more immunogenic and superior to vaccines derived from other *S. Typhimurium* strains (Zhang et al., 1997). LB broth and agar (Bertani, 1951) will be used as complex media for propagation and plating of *Salmonella* strains. Purple broth (Difco) and MacConkey agar with 0.5% lactose will be used as necessary.

Molecular and Genetic Procedures.

Methods for DNA isolation, restriction enzyme digestion, DNA cloning, and use of PCR for construction and verification of vectors and strains are standard (Sambrook, 2001). All DNA syntheses will be done commercially with codon optimization to enhance translational efficiency in *Salmonella* and to stabilize mRNA by destroying (removing) RNase E cleavage sites thereby prolonging mRNA half-life (Ehretsmann et al., 1992; McDowall et al., 1995; Lin-Chao et al., 1994). Plasmids will be sequenced and tested for ability to specify synthesis of proteins using gel electrophoresis and western blot analyses. DNA vaccine constructs will be similarly tested after electroporation into Vero cells.

Strain Characterization.

*S. Typhimurium* strains χ11829, and χ12341 will be electroporated with the constructed antigen-encoding lysis vectors (FIG. 1E (base vector of FIG. 1D containing nucleic acid sequence encoding codon optimized envelope (E) protein) and 1F (base vector of FIG. 1D containing nucleic acid sequence encoding codon optimized envelope (E) protein and amino acid substitutions at ASN154 and ASN481) and 1I (base vector containing nucleic acid sequence encoding a fusion protein of membrane precursor (prM) and NS5 (each of which is not codon optimized for χ11829 and χ12341) and χ11848 with DNA vaccine vectors (illustrated in FIGS. 1B (base vector), 1G (base vector containing nucleic acid sequence encoding non-codon optimized envelope (E) protein) and 1H (base vector containing nucleic acid sequence encoding codon optimized envelope (E) protein and amino acid substitutions at ASN154 and ASN481 for χ11848), respectively, and evaluated in comparison with strains containing empty vector controls (e.g., vectors illustrated in FIGS. 1C (base vector (empty control vector) with modified Shine Dalgarno sequences), 1D (base vector; empty control vector) for χ11829 and 1B (base vector; empty control vector) for χ11848). Metrics will include: stability of plasmid maintenance, integrity, and antigen synthesis ability when strains are grown in the presence of arabinose and DAP for 50 generations (Galán et al., 1990). Final RASVs will be evaluated for synthesis of LPS O-antigen (Hitchcock et al., 1983), bile sensitivity, acid tolerance, and ability to survive in sera with and without complement inactivation and in macrophages (Curtiss et al., 2009; Shi et al., 2009). These tests will be conducted with RASVs grown with and without 0.1% media supplementation with mannose. Sensitivity to all antibiotics used to treat *Salmonella* infections will also be validated. Strain metabolic attributes will be evaluated using API-20E tests. DNA vaccine constructs will be transfected into Vero cells to evaluate synthesis and masses of encoded protective antigens in the presence and absence of tunicamycin to block glycosylation.

Viruses.

ZIKV MR-766 (original-African), ZIKV PRVABC59 (outbreak-Asian), DENV-1-HI, DENV-2 NGC, DENV-3 H87, and DENV-4 H241tc will be used. ZIKV PRVABC59 was used to design plasmid constructs.

Antigen Preparation:

Viral antigens specified by RASVs will be synthesized as His-tagged proteins in recombinant *E. coli*. The *E. coli* used lacks flagella, fimbrial antigens, and LPS O-antigen to enhance purity of recombinant proteins. Glycosylated viral proteins will be isolated from ZIKV, synthesized, or obtained commercially. *Salmonella* B group LPS O-antigens will be obtained commercially. *S. Typhimurium* outer membrane protein (SOMP) fraction and heat-killed extracts of the wild-type parental *Salmonella* strain used to construct RASVs will be used as controls in western blots and for immunoassays.

ELISA:

Serum antibodies from mice will be measured in blood collected from mice and a doubling dilution method, with the end-point titer being the dilution giving an $OD_{450}$ three times that for the reagent or unimmunized animal control, will be employed. Titers of IgG1 and IgG2a will be determined to distinguish between Th1 and Th2 responses. ZIKV antigens will be obtained from recombinant proteins and whole virus. Mucosal antibody secretion will be measured by ELISPOT analyses and in vaginal secretions by ELISA.

Flow Cytometry Analysis:

Flow cytometry will be used to quantitate populations of CD4+, CD8+ and CD17+ T cells and specific cytokine-secreting cells in peripheral blood, kidneys, and spleens of mice immunized with RASV strains delivering protective antigens or DNA vaccines encoding viral antigens. Single cell suspensions from kidney and spleens of individual mice will be suspended in PBS in the presence of purified antigens and incubated with specific antibodies for detection of cell surface molecules. Presence of CD4, CD8, CD11a, CD17, CD44, and CD62L markers on cell surfaces will be assessed using fluorescence-labeled antibodies specific for each marker. Intracellular IFN-γ, TNF-α, IL-17, and IL-10 production by CD4+ T cells will also be measured using specific antibodies. All samples will be analyzed on a Becton Dickinson LSR Fortessa instrument and data analyzed using FCS Express 4 Flow Research Edition software.

T-cell Proliferation Assays/CTL Responses:

Will be performed as described in (Kappes et al., 2012).

Virus Neutralization Assays:

To determine if the RASV constructs induce neutralizing antibody responses, ZIKV-neutralizing properties of sera from vaccinated and non-vaccinated mice will be tested. Sera will be assayed using standard ZIKV or DENV plaque-reduction-neutralization tests.

Enhancement and Antibody Dependent Enhancement-Inhibition Assays:

Whole serum from RASV-immunized and non-immunized mice will be studied to determine how antibodies to ZIKV behave upon encounter with DENV. These assays will be performed as described in the literature using human macrophage/PBMC cells (Nicholson et al., 2011; Sasaki et al., 2013). The results will be analyzed using the ΔΔ Ct method.

Statistical Analyses:

All results will be analyzed using the most appropriate statistical tests from the SAS program to evaluate the relative significance or lack thereof of results obtained.

Example 1—Procedural Overview for Constructions and Evaluations

RASVs delivering DNA vaccine vectors and RASVs synthesizing protein antigen from antigen-encoding lysis vectors will be produced as described above in the "Strain characterization" section. Five RASVs delivering ZIKV DNA vaccines, a vector control and a buffered saline control will be administered to groups of female BALB/c mice (10 animals per group). The immunization protocol comprises orally administering $10^9$ CFU on days 0, 7, and 49 and a repeat experiment of a longer duration that uses the same or a lower dose will be also be performed before giving the booster immunization. Sera will be collected on days −1, 14, 28, 42, 56, and 70. Mucosal and serum antibody titers to each of the three ZIKV surface antigens and to *Salmonella* LPS and OMPs will be determined using ELISA. Neutralizing antibody titers against ZIKV and DENV types 1-4 will be determined via virus neutralization assays.

At 70 days, mice will be euthanized and peripheral blood and spleen cells evaluated for antigen-specific lymphocyte proliferation, cytokine production, and CD4-, CD8- and NKT-dependent responses using tetramers. ELISA and/or plaque reduction neutralization test (PRNT) assays will be used to identify any cross-reactivity or enhancing effects of immune responses with DENV types 1-4. PRNT will be used, as well as enhancement and antibody dependent enhancement-inhibition assays, to identify and describe any virus-neutralizing and/or enhancing properties.

RASVs containing antigen-encoding lysis vectors that direct synthesis of non-glycosylated C, prM and E proteins will also be evaluated. These antigen-encoding lysis vectors will contain codon-optimized sequences encoding the three ZIKV surface proteins individually and one encoding all three proteins. Each of these four plasmids will be electroporated into $\chi$11829 or $\chi$12341. The four RASVs synthesizing and delivering ZIKV surface antigens will be evaluated in groups containing 10 mice per experimental and control group. We will orally immunize BALB/c mice on days 0, 7, and 49 with each recombinant vaccine and collect sera on days −1, 14, 28, 42, 56, and 70. ELISA will be used to determine antibody titers to each of the three surface antigens and to *Salmonella* LPS and OMPs. We will also determine whether any antibodies neutralize ZIKV but fail to react with any DENV surface proteins via ELISA and virus neutralization assays. At 70 days, we will euthanize the mice and evaluate peripheral blood and spleen cells for antigen-specific lymphocyte proliferation, cytokine production and CD4-, CD8- and NKT-dependent responses using tetramers. Additional experiments will be conducted to assess the presence of specificity for ZIKV proteins and the absence of cross-reactivity or enhancing effects of immune responses with proteins from DENV types 1-4 using ELISA and virus neutralization assays as well as enhancement and antibody dependent enhancement-inhibition assays. We will also examine whether ZIKV-specific T-cells will kill ZIKV-infected Vero cells.

Additional experiments using RASVs containing antigen-encoding lysis vectors that direct synthesis of non-glycosylated ZIKV NS1-NS2A-NS2B-NS3 as a polyprotein fusion and ZIKV NS4A-2K-NS4B-NS5 as a polyprotein fusion or individual NS1, NS2A, NS2B, NS3, NS4A, NS4b and NS5 will also be evaluated. These antigen-encoding lysis vectors will contain codon-optimized sequences encoding the individual or polyproteins. Each of these plasmids will be electroporated into $\chi$11829 or $\chi$12341. The RASVs synthesizing and delivering ZIKV NS proteins will be evaluated in groups containing 10 mice per experimental and control groups (immunized with an empty (base) lysis vector and buffer). We will orally immunize BALB/c mice on days 0, 7, and 49 with each recombinant vaccine and collect sera on days −1, 14, 28, 42, 56, and 70. ELISA will be used to determine antibody titers to each of the seven non-structural proteins and to *Salmonella* LPS and OMPs will be quantified via ELISA. We will determine whether any antibodies neutralize ZIKV and fail to react with any DENV surface proteins via ELISA and/or virus neutralization tests. At 70 days, we will euthanize the mice and evaluate peripheral blood and spleen cells for antigen-specific lymphocyte proliferation, cytokine production and CD4-, CD8- and NKT-dependent responses using tetramers of the non-structural proteins. We will also examine whether ZIKV-specific T-cells to the non-structural proteins will kill ZIKV-infected Vero cells.

Example 2—Construction of Lysis Vectors Encoding NS Proteins

We inserted the codon optimized sequences for NS4A and NS4B (lower sequences in FIGS. 11 and 12) into the pYA4589 (p15A ori) vector (FIG. 1D) to yield pG8R124 (FIG. 13) and pG8R125 (FIG. 14), respectively. However, initially both sequences with a C-terminal 6-His tag, to enable measurement of levels of protein synthesis using the mouse monoclonal poly-histidine antibody clone HIS-1 (Sigma H1029), were inserted into pYA4589 and the sequences encoding the 6-His residues deleted by plasmid digestion with NaeI (see sequences at the bottom of FIGS. 11 and 12). All plasmids were initially electroporated into *E. coli* K-12 $\chi$6212(pYA232) (F⁻λ⁻φ80 Δ(lacZYA-argF) endA1 recA1 hsdR17 deoR thi-1 glnV44 gyrA96 relA1 ΔasdA4 with pYA232 encoding lacI$^q$) with selection for Asd⁺ in the presence of 0.1% arabinose. Asd+ isolates were tested for presence of the plasmid of the correct size and content and ability to grow in the presence of IPTG to relieve the LacI repression of transcription from the plasmid P$_{trc}$ to ensure that synthesis of the encoded ZIKV protein was not toxic. The recombinant plasmids were then electroporated into the *S. Typhimurium* $\chi$12341 and growth evaluated in the presence and absence of IPTG. Recombinant clones with the His-tagged sequence were evaluated for synthesis if the His-tagged ZIKV proteins. All RASV strains were tested for synthesis of LPS O-antigen dependent on presence of mannose and rhamnose. This verified that rough variants were not selected during the electroporation operation. RASVs were then tested for stability of plasmid maintenance and ability to synthesize the ZIKV antigen after 50 generations of growth under permissive conditions in DAP-supplemented LB broth. $\chi$12341(pG8R124) and $\chi$12341(pG8R125) were then judged to satisfy all criteria to advance toward evaluation in mice.

Example 3—Construction of Lysis Vectors Encoding prM-E Fusion Protein

The immune response to the prM-E fusion should result from a combined production of neutralizing antibodies and cellular immunity. Since some cross reactive antibodies might be due to glycosylation, the synthesis and delivery of this fusion protein from *Salmonella* should eliminate such glycosylation even without alteration of the N-X-S/T glycosylation sites in the E encoding sequence. As in Example 2, the codon-optimized sequence for the prM-E fusion (FIG. 15) with the C-terminal 6-His tag was inserted into pYA4589, which was then electroporated into $\chi$6212 (pYA232). The NaeI digested plasmid without the His tag was also electroporated into $\chi$6212(pYA232) and designated pG8R126 (FIG. 16). All of the procedures for plasmid characterization were as described in Example 2 both before and after introducing pG8R126 into $\chi$12341. $\chi$12341 (pG8R126) is thus ready for studies in mice as described in the Material and Methods section.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

TABLE 1

Mutations and associated phenotypes in *S. Typhimurium* vaccine strains[a]

| Genotype | Phenotype |
|---|---|
| A. Deletion and deletion-insertion mutations to confer regulated delayed in vivo attenuation phenotype | |
| Δpmi | encodes phosphomannose isomerase needed for synthesis of GDP-mannose for LPS O-antigen and thus necessary for virulence |
| ΔwaaL ΔpagL::TT rhaRS $P_{rhaBAD}$ waaL | regulates synthesis of enzyme responsible for attaching first subunit of LPS O-antigen to the LPS core (the deletion of the waaL gene is necessary to prevent impairment in expression of other rfb operon genes); the regulated expression cassette is therefore inserted into the pagL gene. |
| B. Promoters and deletion-insertion mutations for regulated delayed in vivo synthesis of antigens | |
| $P_{trc}$ | a promoter expressed at high level under both anaerobic and aerobic conditions and repressed by LacI |
| ΔrelA::araC $P_{BAD}$ lacI TT | The arabinose-dependent synthesis of the LacI repressor is to enable a regulated delayed expression of DNA sequences under the control of $P_{trc}$ |
| Phage P22 $P_R$ | promoter is repressible by arabinose-dependent synthesis of the C2 repressor |
| C. Deletion and deletion-insertion mutations to facilitate regulated delayed lysis in vivo | |
| $\Delta P_{murA}$::TT araC $P_{BAD}$ murA | makes synthesis of MurA, the first enzyme in the synthesis of muramic acid, dependent on arabinose in growth medium and ceases synthesis in vivo due to absence of arabinose. MurA decreases due to cell division in vivo to ultimately lyse and die. The murA defect is complemented by MurA$^+$ plasmid vectors. |
| ΔasdA::TT araC $P_{BAD}$ c2 | the Asd enzyme is essential for the synthesis of diaminopimelic acid (DAP) required for peptidoglycan synthesis. The arabinose-dependent synthesis of the C2 repressor enables a regulated delayed expression of DNA sequences under control of C2 repressed promoters. The ΔasdA mutation is complemented by Asd$^+$ plasmids |
| ΔrelA | the relA mutation uncouples growth regulation from a dependence on protein synthesis, an important attribute in strains with regulated delayed lysis |
| Δ(wza-wcaM) | eliminates twenty enzymes needed to synthesize several exopolysaccharides that promote biofilm formation and synthesis of GDP-fucose required for colanic acid synthesis, which protects cells undergoing cell wall-less death from lysing |
| D. Other contributing mutations | |
| ΔsifA | enables *Salmonella* to escape the SCV for lysis in cytosol |
| ΔrecF & ΔrecJ | eliminate recombinases facilitating inter- and intra-plasmidic recombination |
| ΔsseL ΔtlpA | decrease and delay *Salmonella*-induced pyroptosis/apoptosis |
| ΔmsbB | alters LPS lipid A to render it less toxic |
| ΔpagP::$P_{trc}$ lpxE mutation | causes regulated delayed in vivo synthesis of the codon-optimized lpxE gene from *Francisella tularensis* to cause synthesis of the non-toxic adjuvant form of LPS lipid A monophosphoryl lipid A (MPLA) |

[a] Δ = deletion; TT = transcription terminator; P = promoter

REFERENCES

Curtiss R, III., S. B. Porter, M. Munson, S. A. Tinge, J. O. Hassan, C. Gentry-Weeks, Kelly. SM. Nonrecombinant and recombinant avirulent *Salmonella* live vaccines for poultry. In: L. C. Blankenship, J. H. S. Bailey, N. A. Cox, Stern N J, Meinersmann R J, editors. Colonization control of human bacterial enteropathogens in poultry. New York Academic Press 1991. p. 169-98.

Zhang X, Kelly S M, Bollen W S, Curtiss R, III. Characterization and immunogenicity of *Salmonella typhimurium* SL1344 and UK-1 Dcrp and Dcdt deletion mutants. Infection and immunity. 1997; 65(12):5381-7.

Bertani G. Studies on lysogenesis. I. The mode of phage liberation by lysogenic *Escherichia coli*. Journal of bacteriology. 1951; 62(3):293-300.

Sambrook J, Russell D W. Molecular cloning: a laboratory manual. 3rd ed. Cold Spring Harbor, N.Y.: Cold Spring Harbor Laboratory Press; 2001.

Ehretsmann C P, Carpousis A J, Krisch H M. Specificity of *Escherichia coli* endoribonuclease RNase E: in vivo and in vitro analysis of mutants in a bacteriophage T4 mRNA processing site. Genes Dev. 1992; 6(1):149-59.

McDowall K J, Kaberdin V R, Wu S W, Cohen S N, Lin-Chao S. Site-specific RNase E cleavage of oligonucleotides and inhibition by stem-loops. Nature. 1995; 374(6519):287-90.

Lin-Chao S, Wong T T, McDowall K J, Cohen S N. Effects of nucleotide sequence on the specificity of me-dependent and RNase E-mediated cleavages of RNA I encoded by the pBR322 plasmid. J Biol Chem. 1994; 269(14):10797-803.

Galán J E, Nakayama K, Curtiss R, III. Cloning and characterization of the asd gene of *Salmonella typhimurium*: use in stable maintenance of recombinant plasmids in *Salmonella* vaccine strains. Gene. 1990; 94(1):29-35.

Hitchcock P J, Brown T M. Morphological heterogeneity among *Salmonella* lipopolysaccharide chemotypes in silver-stained polyacrylamide gels. Journal of bacteriology. 1983; 154(1):269-77.

Curtiss R, III, Wanda S Y, Gunn B M, Zhang X, Tinge S A, Ananthnarayan V, Mo H, Wang S, Kong W. *Salmonella enterica* serovar *Typhimurium* strains with regulated delayed attenuation in vivo. Infect Immun. 2009; 77(3): 1071-82.

Shi H, Santander J, Brenneman K E, Wanda S Y, Wang S, Senechal P, Sun W, Roland K L, Curtiss R, III. Live recombinant *Salmonella Typhi* vaccines constructed to investigate the role of rpoS in eliciting immunity to a heterologous antigen. PLoS One. 2010; 5(6):e11142.

Kappes M A, Sandbulte M R, Platt R, Wang C, Lager K M, Henningson J N, Lorusso A, Vincent A L, Loving C L, Roth J A, Kehrli M E, Jr. Vaccination with NS1-truncated H3N2 swine influenza virus primes T cells and confers cross-protection against an H1N1 heterosubtypic challenge in pigs. Vaccine. 2012; 30(2):280-8.

Nicholson C O, Costin J M, Rowe D K, Lin L, Jenwitheesuk E, Samudrala R, Isern S, Michael S F. Viral entry inhibitors block dengue antibody-dependent enhancement in vitro. Antiviral Res. 2011; 89(1):71-4.

Sasaki T, Setthapramote C, Kurosu T, Nishimura M, Asai A, Omokoko M D, Pipattanaboon C, Pitaksajjakul P, Limkittikul K, Subchareon A, Chaichana P, Okabayashi T, Hirai I, Leaungwutiwong P, Misaki R, Fujiyama K, Ono K, Okuno Y, Ramasoota P, Ikuta K. Dengue virus neutralization and antibody-dependent enhancement activities of human monoclonal antibodies derived from dengue patients at acute phase of secondary infection. Antiviral Res. 2013; 98(3):423-31.

Kong W, Brovold M, Koeneman B A, Clark-Curtiss J, and Curtiss III, R. Turning self-destructing *Salmonella* into a universal DNA vaccine delivery platform. Proc. Natl. Acad. Sci. USA. 2012: 109(47):19414-19419.

Fluman N, Navon S, Bibi E, Pilpel Y. 2014. mRNA-programmed translation pauses in the targeting of *E. coli* membrane proteins. Elife 3.

Komar A A, Lesnik T, Reiss C. 1999. Synonymous codon substitutions affect ribosome traffic and protein folding during in vitro translation. FEBS Lett 462:387-391.

Kimchi-Sarfaty C, Oh J M, Kim I W, Sauna Z E, Calcagno A M, Ambudkar S V, Gottesman M M. 2007. A "silent" polymorphism in the MDR1 gene changes substrate specificity. Science 315:525-528.

Cortazzo P, Cervenansky C, Marin M, Reiss C, Ehrlich R, Deana A. 2002. Silent mutations affect in vivo protein folding in *Escherichia coli*. Biochem Biophys Res Commun 293:537-541.

Gingold H, Pilpel Y. 2011. Determinants of translation efficiency and accuracy. Mol Syst Biol 7:481.

SEQUENCE LISTING

```
<160> NUMBER OF SEQ ID NOS: 38

<210> SEQ ID NO 1
<211> LENGTH: 309
<212> TYPE: DNA
<213> ORGANISM: Zika Virus

<400> SEQUENCE: 1
atgaaaaacc caaaaagaa atccggagga ttccggattg tcaatatgct aaaacgcgga      60
gtagcccgtg tgagcccctt tggggcttg aagaggctgc cagccggact tctgctgggt    120
catgggccca tcaggatggt cttggcgatt ctagcctttt tgagattcac ggcaatcaag   180
ccatcactgg gtctcatcaa tagatggggt tcagtgggga aaaagaggc tatggaaaca    240 ataaagaagt tcaagaaaga tctggctgcc atgctgagaa taatcaatgc taggaaggag   300
aagaagaga                                                              309

<210> SEQ ID NO 2
<211> LENGTH: 309
<212> TYPE: DNA
<213> ORGANISM: Zika Virus

<400> SEQUENCE: 2
atgaaaaacc caaaaagaa atccggtggt ttccgtattg tcaatatgct gaaacgcggt      60
gtagcccgtg tgagcccgtt tggcggcttg aagcgtctgc cagccggcct gctgctgggt   120 catggccga tccgtatggt cctggcgatt ctggcctttc tgcgtttcac ggcaatcaag    180
ccatcactgg gtctcatcaa tcgttgggt tcagtgggga aaaagaggc tatggaaaca     240 atcaagaagt tcaagaaaga tctggctgcc atgctgcgca ttatcaatgc tcgcaaggag   300
aagaagcgc                                                              309

<210> SEQ ID NO 3
<211> LENGTH: 103
```

```
<212> TYPE: PRT
<213> ORGANISM: Zika Virus

<400> SEQUENCE: 3

Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
                20                  25                  30

Leu Pro Ala Gly Leu Leu Gly His Gly Pro Ile Arg Met Val Leu
            35                  40                  45

Ala Ile Leu Ala Phe Leu Arg Phe Thr Ala Ile Lys Pro Ser Leu Gly
        50                  55                  60

Leu Ile Asn Arg Trp Gly Ser Val Gly Lys Lys Glu Ala Met Glu Thr
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg
            100

<210> SEQ ID NO 4
<211> LENGTH: 279
<212> TYPE: DNA
<213> ORGANISM: Zika Virus

<400> SEQUENCE: 4
gcggaggtca ctagacgtgg gagtgcatac tatatgtact tggacagaaa cgatgctggg      60
gaggccatat cttttccaac cacattgggg atgaataagt gttatataca gatcatggat     120
cttggacaca tgtgtgatgc caccatgagc tatgaatgcc ctatgctgga tgaggggtg      180 gaaccagatg acgtcgattg ttggtgcaac acgacgtcaa cttgggttgt gtacggaacc     240
tgccatcaca aaaaggtga agcacggaga tctagaaga                             279

<210> SEQ ID NO 5
<211> LENGTH: 288
<212> TYPE: DNA
<213> ORGANISM: Zika Virus

<400> SEQUENCE: 5
atgaaaaagg cggaggtcac tcgtcgtggt agcgcatact atatgtacct ggaccgcaac      60
gatgctggcg aggccatctc ttttccaacc accttgggta tgaataagtg ttatatccag     120
atcatggatc tgggccacat gtgtgatgcc accatgagct atgaatgccc tatgctggat     180 gaggggtgg aaccagatga cgtcgattgt tggtgcaaca cgacgtcaac ttgggttgtg      240
tacggtacct gccatcacaa aaaggtgaa gcacgccgct ctcgccgc                   288

<210> SEQ ID NO 6
<211> LENGTH: 96
<212> TYPE: PRT
<213> ORGANISM: Zika Virus

<400> SEQUENCE: 6

Met Lys Lys Ala Glu Val Thr Arg Arg Gly Ser Ala Tyr Tyr Met Tyr
1               5                   10                  15

Leu Asp Arg Asn Asp Ala Gly Glu Ala Ile Ser Phe Pro Thr Thr Leu
                20                  25                  30

Gly Met Asn Lys Cys Tyr Ile Gln Ile Met Asp Leu Gly His Met Cys
            35                  40                  45
```

```
              Asp Ala Thr Met Ser Tyr Glu Cys Pro Met Leu Asp Glu Gly Val Glu
                  50                  55                  60

Pro Asp Asp Val Asp Cys Trp Cys Asn Thr Ser Thr Trp Val Val
              65                  70                  75                  80

Tyr Gly Thr Cys His His Lys Lys Gly Glu Ala Arg Arg Ser Arg Arg
                              85                  90                  95

<210> SEQ ID NO 7
<211> LENGTH: 1512
<212> TYPE: DNA
<213> ORGANISM: Zika Virus

<400> SEQUENCE: 7
atcaggtgca taggagtcag caatagggac tttgtggaag gtatgtcagg tgggacttgg      60
gttgatgttg tcttggaaca tggaggttgt gtcaccgtaa tggcacagga caaaccgact     120
gtcgacatag agctggttac aacaacagtc agcaacatgg cggaggtaag atcctactgc     180
tatgaggcat caatatcaga catggcttct gacagccgct gcccaacaca aggtgaagcc     240
taccttgaca agcaatcaga cactcaatat gtctgcaaaa gaacgttagt ggacagaggc     300
tggggaaatg gatgtggact ttttggcaaa gggagcctgg tgacatgcgc taagtttgca     360
tgctccaaga aaatgaccgg gaagagcatc cagccagaga atctggagta ccggataatg     420
ctgtcagttc atggctccca gcacagtggg atgatcgtta atgacacagg acatgaaact     480
gatgagaata gagcgaaagt tgagataacg cccaattcac cgagagccga agccaccctg     540
gggggttttg gaagcctagg acttgattgt gaaccgagga caggccttga cttttcagat     600
ttgtattact tgactatgaa taacaagcac tggttggttc acaaggagtg gttccacgac     660
attccattac cttggcacgc tggggcagac accggaactc acactggaa caacaaagaa     720 gcactggtag agttcaagga cgcacatgcc aaaaggcaaa ctgtcgtggt tctagggagt     780
caagaaggag cagttcacac ggcccttgct ggagctctgg aggctgagat ggatggtgca     840
aagggaaggc tgtcctctgg ccacttgaaa tgtcgcctga aatggataa acttagattg     900 aagggcgtgt catactcctt gtgtactgca gcgttcacat tcaccaagat cccggctgaa     960
acactgcacg ggacagtcac agtggagtta cagtacgcag ggacagatgg accttgcaag    1020
gttccagctc agatggcggt ggacatgcaa actctgaccc cagttgggag gttgataacc    1080
gctaaccccg taatcactga aagcactgag aactctaaga tgatgctgga acttgatcca    1140
ccatttgggg actcttacat tgtcatagga gtcggggaga agaagatcac ccaccactgg    1200
cacaggagtg gcagcaccat ggaaaaagca tttgaagcca ctgtgagagg tgccaagaga    1260
atggcagtct gggagacac agcctgggac tttggatcag tggaggcgc tctcaactca    1320 ttgggcaagg gcatccatca aattttttgga gcagctttca atcattgtt tggaggaatg    1380 tcctggttct cacaaattct cattggaacg ttgctgatgt ggttgggtct gaacacaaag    1440
aatggatcta tttcccttat gtgcttggcc ttaggggag tgttgatctt cttatccaca    1500
gccgtctctg ct                                                        1512

<210> SEQ ID NO 8
<211> LENGTH: 1518
<212> TYPE: DNA
<213> ORGANISM: Zika Virus

<400> SEQUENCE: 8
atgaaaatcc gctgcatcgg tgtcagcaat cgtgactttg tggaaggtat gtccggtggt      60
```

```
acttgggttg atgttgtcct ggaacatggc ggttgtgtca ccgtaatggc acaggacaaa      120
ccgactgtcg acatcgagct ggttaccacc accgtcagca acatggcgga ggtacgttcc      180
tactgctatg aggcatccat ctccgacatg gcttctgaca gccgctgccc aacccaaggt      240
gaagcctacc ttgacaagca atccgacact caatatgtct gcaaacgtac gctggtggac      300
cgtggctggg gcaatggttg tggccttttt ggtaaaggga gcctggtgac ctgcgctaag      360
tttgcatgct ccaagaaaat gaccggcaag agcatccagc cagagaatct ggagtaccgc      420
atcatgctgt cagttcatgg ctcccagcac agtgggatga tcgttcagga cacaggtcat      480
gaaactgatg agaatcgcgc gaaagttgag atcacgccca attcaccgcg tgccgaagcc      540
accctggggg gttttggtag cctaggtctt gattgtgaac cgcgtacagg ccttgacttt      600
tcagatttgt attacttgac tatgaataac aagcactggt tggttcacaa ggagtggttc      660
cacgacattc cattaccttg gcacgctggg gcagacaccg gtactccaca ctggaacaac      720
aaagaagcac tggtagagtt caaggacgca catgccaaac gtcaaactgt cgtggttctg      780
gggagtcaag aaggtgcagt tcacacggcc cttgctggtg ctctggaggc tgagatggat      840
ggtgcaaagg ccgcctgtc ctctggccac ttgaaatgtc gcctgaaaat ggataaactt      900
cgtttgaagg gtgtgtcata ctccttgtgt actgcagcgt tcacattcac caagatcccg      960
gctgaaacac tgcacgggac agtcacagtg gagttacagt acgcagggac agatggtcct     1020
tgcaaggttc agctcagat ggcggtggac atgcaaactc tgaccccagt ggggcgtttg     1080
atcaccgcta acccggtaat cactgaaagc actgagaact ctaagatgat gctggaactt     1140
gatccaccat ttgggggactc ttacattgtc atcggtgtcg gggagaagaa gatcacccac     1200
cactggcacc gcagtggcag caccattggt aaagcatttg aagccactgt gcgtggtgcc     1260
aagcgtatgg cagtcttggg tgacacagcc tgggactttg gttcagttgg cggcgctctc     1320
aactcattgg gcaagggcat ccatcaaatt tttggcgcag ctttcaaatc attgtttggt     1380
ggtatgtcct ggttctcaca aattctcatt ggaacgttgc tgatgtggtt gggtctgaac     1440
acaaaggagg gctctatttc ccttatgtgc ttggccttag ggggtgtgtt gatcttctta     1500
tccacagccg tctctgct                                                   1518
```

<210> SEQ ID NO 9
<211> LENGTH: 506
<212> TYPE: PRT
<213> ORGANISM: Zika Virus

<400> SEQUENCE: 9

```
Met Lys Ile Arg Cys Ile Gly Val Ser Asn Arg Asp Phe Val Glu Gly
1               5                   10                  15

Met Ser Gly Gly Thr Trp Val Asp Val Val Leu Glu His Gly Gly Cys
            20                  25                  30

Val Thr Val Met Ala Gln Asp Lys Pro Thr Val Asp Ile Glu Leu Val
        35                  40                  45

Thr Thr Thr Val Ser Asn Met Ala Glu Val Arg Ser Tyr Cys Tyr Glu
    50                  55                  60

Ala Ser Ile Ser Asp Met Ala Ser Asp Ser Arg Cys Pro Thr Gln Gly
65                  70                  75                  80

Glu Ala Tyr Leu Asp Lys Gln Ser Asp Thr Gln Tyr Val Cys Lys Arg
                85                  90                  95

Thr Leu Val Asp Arg Gly Trp Gly Asn Gly Cys Gly Leu Phe Gly Lys
            100                 105                 110
```

Gly Ser Leu Val Thr Cys Ala Lys Phe Ala Cys Ser Lys Lys Met Thr
            115                 120                 125

Gly Lys Ser Ile Gln Pro Glu Asn Leu Glu Tyr Arg Ile Met Leu Ser
130                 135                 140

Val His Gly Ser Gln His Ser Gly Met Ile Val Asn Asp Thr Gly His
145                 150                 155                 160

Glu Thr Asp Glu Asn Arg Ala Lys Val Glu Ile Thr Pro Asn Ser Pro
                165                 170                 175

Arg Ala Glu Ala Thr Leu Gly Gly Phe Gly Ser Leu Gly Leu Asp Cys
                180                 185                 190

Glu Pro Arg Thr Gly Leu Asp Phe Ser Asp Leu Tyr Tyr Leu Thr Met
            195                 200                 205

Asn Asn Lys His Trp Leu Val His Lys Glu Trp Phe His Asp Ile Pro
210                 215                 220

Leu Pro Trp His Ala Gly Ala Asp Thr Gly Thr Pro His Trp Asn Asn
225                 230                 235                 240

Lys Glu Ala Leu Val Glu Phe Lys Asp Ala His Ala Lys Arg Gln Thr
                245                 250                 255

Val Val Val Leu Gly Ser Gln Glu Gly Ala Val His Thr Ala Leu Ala
            260                 265                 270

Gly Ala Leu Glu Ala Glu Met Asp Gly Ala Lys Gly Arg Leu Ser Ser
            275                 280                 285

Gly His Leu Lys Cys Arg Leu Lys Met Asp Lys Leu Arg Leu Lys Gly
            290                 295                 300

Val Ser Tyr Ser Leu Cys Thr Ala Ala Phe Thr Phe Thr Lys Ile Pro
305                 310                 315                 320

Ala Glu Thr Leu His Gly Thr Val Thr Val Glu Leu Gln Tyr Ala Gly
                325                 330                 335

Thr Asp Gly Pro Cys Lys Val Pro Ala Gln Met Ala Val Asp Met Gln
            340                 345                 350

Thr Leu Thr Pro Val Gly Arg Leu Ile Thr Ala Asn Pro Val Ile Thr
            355                 360                 365

Glu Ser Thr Glu Asn Ser Lys Met Met Leu Glu Leu Asp Pro Pro Phe
370                 375                 380

Gly Asp Ser Tyr Ile Val Ile Gly Val Gly Glu Lys Lys Ile Thr His
385                 390                 395                 400

His Trp His Arg Ser Gly Ser Thr Ile Gly Lys Ala Phe Glu Ala Thr
                405                 410                 415

Val Arg Gly Ala Lys Arg Met Ala Val Leu Gly Asp Thr Ala Trp Asp
            420                 425                 430

Phe Gly Ser Val Gly Gly Ala Leu Asn Ser Leu Gly Lys Gly Ile His
            435                 440                 445

Gln Ile Phe Gly Ala Ala Phe Lys Ser Leu Phe Gly Gly Met Ser Trp
450                 455                 460

Phe Ser Gln Ile Leu Ile Gly Thr Leu Leu Met Trp Leu Gly Leu Asn
465                 470                 475                 480

Thr Lys Asn Gly Ser Ile Ser Leu Met Cys Leu Ala Leu Gly Gly Val
                485                 490                 495

Leu Ile Phe Leu Ser Thr Ala Val Ser Ala
                500                 505

<210> SEQ ID NO 10
<211> LENGTH: 506
<212> TYPE: PRT

-continued

<213> ORGANISM: Zika Virus

<400> SEQUENCE: 10

```
Met Lys Ile Arg Cys Ile Gly Val Ser Asn Arg Asp Phe Val Glu Gly
1               5                   10                  15

Met Ser Gly Gly Thr Trp Val Asp Val Val Leu Glu His Gly Gly Cys
            20                  25                  30

Val Thr Val Met Ala Gln Asp Lys Pro Thr Val Asp Ile Glu Leu Val
        35                  40                  45

Thr Thr Thr Val Ser Asn Met Ala Glu Val Arg Ser Tyr Cys Tyr Glu
    50                  55                  60

Ala Ser Ile Ser Asp Met Ala Ser Asp Ser Arg Cys Pro Thr Gln Gly
65                  70                  75                  80

Glu Ala Tyr Leu Asp Lys Gln Ser Asp Thr Gln Tyr Val Cys Lys Arg
                85                  90                  95

Thr Leu Val Asp Arg Gly Trp Gly Asn Gly Cys Gly Leu Phe Gly Lys
            100                 105                 110

Gly Ser Leu Val Thr Cys Ala Lys Phe Ala Cys Ser Lys Lys Met Thr
        115                 120                 125

Gly Lys Ser Ile Gln Pro Glu Asn Leu Glu Tyr Arg Ile Met Leu Ser
130                 135                 140

Val His Gly Ser Gln His Ser Gly Met Ile Val Gln Asp Thr Gly His
145                 150                 155                 160

Glu Thr Asp Glu Asn Arg Ala Lys Val Glu Ile Thr Pro Asn Ser Pro
                165                 170                 175

Arg Ala Glu Ala Thr Leu Gly Gly Phe Gly Ser Leu Gly Leu Asp Cys
            180                 185                 190

Glu Pro Arg Thr Gly Leu Asp Phe Ser Asp Leu Tyr Tyr Leu Thr Met
        195                 200                 205

Asn Asn Lys His Trp Leu Val His Lys Glu Trp Phe His Asp Ile Pro
    210                 215                 220

Leu Pro Trp His Ala Gly Ala Asp Thr Gly Thr Pro His Trp Asn Asn
225                 230                 235                 240

Lys Glu Ala Leu Val Glu Phe Lys Asp Ala His Ala Lys Arg Gln Thr
                245                 250                 255

Val Val Val Leu Gly Ser Gln Glu Gly Ala Val His Thr Ala Leu Ala
            260                 265                 270

Gly Ala Leu Glu Ala Glu Met Asp Gly Ala Lys Gly Arg Leu Ser Ser
        275                 280                 285

Gly His Leu Lys Cys Arg Leu Lys Met Asp Lys Leu Arg Leu Lys Gly
    290                 295                 300

Val Ser Tyr Ser Leu Cys Thr Ala Ala Phe Thr Phe Thr Lys Ile Pro
305                 310                 315                 320

Ala Glu Thr Leu His Gly Thr Val Thr Val Glu Leu Gln Tyr Ala Gly
                325                 330                 335

Thr Asp Gly Pro Cys Lys Val Pro Ala Gln Met Ala Val Asp Met Gln
            340                 345                 350

Thr Leu Thr Pro Val Gly Arg Leu Ile Thr Ala Asn Pro Val Ile Thr
        355                 360                 365

Glu Ser Thr Glu Asn Ser Lys Met Met Leu Glu Leu Asp Pro Pro Phe
    370                 375                 380

Gly Asp Ser Tyr Ile Val Ile Gly Val Gly Glu Lys Lys Ile Thr His
385                 390                 395                 400
```

```
His Trp His Arg Ser Gly Ser Thr Ile Gly Lys Ala Phe Glu Ala Thr
                    405                 410                 415

Val Arg Gly Ala Lys Arg Met Ala Val Leu Gly Asp Thr Ala Trp Asp
                420                 425                 430

Phe Gly Ser Val Gly Gly Ala Leu Asn Ser Leu Gly Lys Gly Ile His
            435                 440                 445

Gln Ile Phe Gly Ala Ala Phe Lys Ser Leu Phe Gly Gly Met Ser Trp
        450                 455                 460

Phe Ser Gln Ile Leu Ile Gly Thr Leu Leu Met Trp Leu Gly Leu Asn
465                 470                 475                 480

Thr Lys Glu Gly Ser Ile Ser Leu Met Cys Leu Ala Leu Gly Gly Val
                485                 490                 495

Leu Ile Phe Leu Ser Thr Ala Val Ser Ala
                500                 505

<210> SEQ ID NO 11
<211> LENGTH: 2709
<212> TYPE: DNA
<213> ORGANISM: Zika Virus

<400> SEQUENCE: 11
gggggtggaa caggagagac cctgggagag aaatggaagg cccgcttgaa ccagatgtcg      60
gccctggagt tctactccta caaaaagtca ggcatcaccg aggtgtgcag agaagaggcc     120
cgccgcgccc tcaaggacgg tgtggcaacg ggaggccatg ctgtgtcccg aggaagtgca     180
aagctgagat ggttggtgga gcggggatac ctgcagccct atggaaaggt cattgatctt     240
ggatgtggca gaggggctg gagttactac gtcgccacca tccgcaaagt tcaagaagtg     300
aaaggataca caaaggagg ccctggtcat gaagaacccg tgttggtgca agctatggg      360 tggaacatag tccgtcttaa gagtggggtg acgtctttc atatggcggc tgagccgtgt     420
gacacgttgc tgtgtgacat aggtgagtca tcatctagtc ctgaagtgga agaagcacgg     480
acgctcagag tcctctccat ggtgggggat tggcttgaaa aaagaccagg agccttttgt     540
ataaaagtgt tgtgcccata caccagcact atgatggaaa ccctggagcg actgcagcgt     600
aggtatgggg gaggactggt cagagtgcca ctctcccgca actctacaca tgagatgtac     660
tgggtctctg gagcgaaaag caacaccata aaaagtgtgt ccaccacgag ccagctcctc     720
ttggggcgca tggacgggcc taggaggcca gtgaaatatg aggaggatgt gaatctcggc     780
tctggcacgc gggctgtggt aagctgcgct gaagctccca acatgaagat cattggtaac     840
cgcattgaaa ggatccgcag tgagcacgcg gaaacgtggt tctttgacga gaaccaccca     900
tataggacat gggcttacca tggaagctat gaggccccca cacaagggtc agcgtcctct     960
ctaataaacg gggttgtcag gctcctgtca aaaccctggg atgtggtgac tggagtcaca     1020
ggaatagcca tgaccgacac cacaccgtat ggtcagcaaa gagttttcaa ggaaaaagtg     1080
gacactaggg tgccagaccc ccaagaaggc actcgtcagg ttatgagcat ggtctcttcc     1140
tggttgtgga aagagctagg caaacacaaa cggccacgag tctgcaccaa agaagagttc     1200
atcaacaagg ttcgtagcaa tgcagcatta ggggcaatat ttgaagagga aaaagagtgg     1260
aagactgcag tggaagctgt gaacgatcca aggttctggg ctctagtgga caggaaaga      1320 gagcaccacc tgagaggaga gtgccagagc tgtgtgtaca acatgatggg aaaaagagaa     1380
aagaaacaag gggaatttgg aaaggccaag ggcagccgcg ccatctggta tatgtggcta     1440
ggggctagat ttcagagtt cgaagcccct tggattcttg acgaggatca ctggatgggg     1500
```

| | |
|---|---:|
| agagagaact caggaggtgg tgttgaaggg ctgggattac aaagactcgg atatgtccta | 1560 |
| gaagagatga gtcgtatacc aggaggaagg atgtatgcag atgacactgc tggctgggac | 1620 |
| acccgcatta gcaggtttga tctggagaat gaagctctaa tcaccaacca aatggagaaa | 1680 |
| gggcacaggg ccttggcatt ggccataatc aagtacacat accaaaacaa agtggtaaag | 1740 |
| gtccttagac cagctgaaaa agggaaaaca gttatggaca ttatttcgag acaagaccaa | 1800 |
| agggggagcg acaagttgt cacttacgct cttaacacat ttaccaacct agtggtgcaa | 1860 |
| ctcattcgga atatggaggc tgaggaagtt ctagagatgc aagacttgtg gctgctgcgg | 1920 |
| aggtcagaga aagtgaccaa ctggttgcag agcaacggat gggataggct caaacgaatg | 1980 |
| gcagtcagtg gagatgattg cgttgtgaag ccaattgatg ataggtttgc acatgccctc | 2040 |
| aggttcttga atgatatggg aaaagttagg aaggacacac aagagtggaa accctcaact | 2100 |
| ggatgggaca actgggaaga agttccgttt tgctcccacc acttcaacaa gctccatctc | 2160 |
| aaggacggga ggtccattgt ggttccctgc cgccaccaag atgaactgat tggccgggcc | 2220 |
| cgcgtctctc caggggcggg atggagcatc cgggagactg cttgcctagc aaaatcatat | 2280 |
| gcgcaaatgt ggcagctcct ttatttccac agaagggacc tccgactgat ggccaatgcc | 2340 |
| atttgttcat ctgtgccagt tgactgggtt ccaactggga gaactacctg gtcaatccat | 2400 |
| ggaaagggag aatggatgac cactgaagac atgcttgtgg tgtggaacag agtgtggatt | 2460 |
| gaggagaacg accacatgga agacaagacc ccagttacga aatggacaga cattccctat | 2520 |
| ttgggaaaaa gggaagactt gtggtgtgga tctctcatag gcacagacc gcgcaccacc | 2580 |
| tgggctgaga acattaaaaa cacagtcaac atggtgcgca ggatcatagg tgatgaagaa | 2640 |
| aagtacatgg actacctatc cacccaagtt cgctacttgg gtgaagaagg gtctacacct | 2700 |
| ggagtgctg | 2709 |

<210> SEQ ID NO 12
<211> LENGTH: 2718
<212> TYPE: DNA
<213> ORGANISM: Zika Virus

<400> SEQUENCE: 12

| | |
|---|---:|
| atgaaaaagg gtggtggtac cggtgagacc ctgggtgaga atggaaggc ccgcctgaac | 60 |
| cagatgtcgg ccctggagtt ctactcctac aaaaagtccg gtatcaccga ggtgtgccgt | 120 |
| gaagaggccc gccgcgccct gaaggacggt gtggcaacgg gtggtcatgc tgtgtcccgt | 180 |
| ggtagcgcaa agctgcgttg gctggtggag cggggttacc tgcagccata tggtaaggtc | 240 |
| attgatcttg gttgtggccg tggcggctgg agctactacg tcgccaccat ccgcaaagtt | 300 |
| caagaagtga aggttacac caaaggtggc cctggtcatg aagaaccagt gctggtgcaa | 360 |
| agctatggct ggaacattgt ccgtctgaag agcggcgtgg acgtctttca tatggcggct | 420 |
| gagccgtgtg acacgctgct gtgtgacatt ggtgagtcct cctctagtcc agaagtggaa | 480 |
| gaagcacgta cgctccgtgt cctgtccatg gtgggtgatt ggctggaaaa acgtccaggt | 540 |
| gccttttgta ttaaagtgct gtgcccatac accagcacta tgatggaaac cctggagcgt | 600 |
| ctgcagcgtc gttatggggg tggtctggtc cgtgtgccac tctcccgcaa ctctacacat | 660 |
| gagatgtact gggtctctgg tgcgaaaagc aacaccatta aaagtgtgtc caccacgagc | 720 |
| cagctcctct tggggcgcat ggacgggcct cgtcgtccag tgaaatatga ggaggatgtg | 780 |
| aatctccggtt ctggtacgcg tgctgtggta agctgcgctg aagctccaaa catgaagatc | 840 |
| attggtaacc gcattgaacg tatccgcagt gagcacgcgg aaacgtggtt ctttgacgag | 900 |

-continued

```
aaccacccat atcgtacatg ggcttaccat ggtagctatg aggccccaac acaagggtca      960
gcgtcctctc tgattaacgg ggttgtccgt ctcctgtcaa aaccatggga tgtggtgact     1020
ggtgtcacag gtattgccat gaccgacacc acaccgtatg gtcagcaacg tgttttcaag     1080
gaaaaagtgg acactcgtgt gccagaccca caagaaggca ctcgtcaggt tatgagcatg     1140
gtctcttcct ggttgtggaa agagctgggc aaacacaaac gtccacgtgt ctgcaccaaa     1200
gaagagttca tcaacaaggt tcgtagcaat gcagcattag ggcaattttt gaagaggaa      1260
aaagagtgga agactgcagt ggaagctgtg aacgatccac gtttctgggc tctggtggac     1320
aaggaacgtg agcaccacct gcgtggtgag tgccagagct gtgtgtacaa catgatgggt     1380
aaacgtgaaa agaaacaagg ggaatttggt aaggccaagg gcagccgcgc catctggtat     1440
atgtggctgg gggctcgttt tctggagttc gaagcccttg gtttcttgaa cgaggatcac     1500
tggatggggc tggagaactc aggtggtggt gttgaagggc tgggtttaca acgtctcggt     1560
tatgtcctgg aagagatgag tcgtattcca ggtggtcgta tgtatgcaga tgacactgct     1620
ggctgggaca cccgcattag ccgttttgat ctggagaatg aagctctgat caccaaccaa     1680
atggagaaag gcaccctggc cttggcattg gccattatca agtacacata ccaaaacaaa     1740
gtggtaaagg tccttcgtcc agctgaaaaa gggaaaacag ttatggacat tatttcgcgt     1800
caagaccaac gtgggagcgg tcaagttgtc acttacgctc ttaacacatt taccaacctg     1860
gtggtgcaac tcattcgtaa tatggaggct gaggaagttc tggagatgca agacttgtgg     1920
ctgctgcgtc gttcagagaa agtgaccaac tggttgcaga gcaacggttg ggatcgtctc     1980
aaacgtatgg cagtcagtgg tgatgattgc gttgtgaagc caattgatga tcgttttgca     2040
catgccctcc gtttcttgaa tgatatgggt aaagttcgta aggacacaca agagtggaaa     2100
ccatcaactg gttgggacaa ctgggaagaa gttccgtttt gctcccacca cttcaacaag     2160
ctccatctca aggacgggcg ttccattgtg gttccatgcc gccaccaaga tgaactgatt     2220
ggccgtgccc gcgtctctcc aggggcgggt tggagcatcc gtgagactgc ttgcctggca     2280
aaatcatatg cgcaaatgtg gcagctcctt tatttccacc gtcgtgacct ccgtctgatg     2340
gccaatgcca tttgttcatc tgtgccagtt gactgggttc aactgggcg tactacctgg    2400
tcaatccatg gtaagggtga atggatgacc actgaagaca tgcttgtggt gtggaaccgt     2460
gtgtggattg aggagaacga ccacatggaa gacaagaccc cagttacgaa atggacagac     2520
attccatatt tgggtaaacg tgaagacttg tggtgtggtt ctctcattgg caccgtccg      2580
cgcaccacct gggctgagaa cattaaaaac acagtcaaca tggtgcgccg tatcattggt     2640
gatgaagaaa agtacatgga ctacctgtcc acccaagttc gctacttggg tgaagaaggg     2700
tctacacctg gtgtgctg                                                  2718
```

<210> SEQ ID NO 13
<211> LENGTH: 900
<212> TYPE: PRT
<213> ORGANISM: Zika Virus

<400> SEQUENCE: 13

Met Lys Lys Gly Gly Thr Gly Glu Thr Leu Gly Glu Lys Trp Lys
1               5                   10                  15

Ala Arg Leu Asn Gln Met Ser Ala Leu Glu Phe Tyr Ser Tyr Lys Lys
            20                  25                  30

Ser Gly Ile Thr Glu Val Cys Arg Glu Glu Ala Arg Arg Ala Leu Lys
        35                  40                  45

```
Asp Gly Val Ala Thr Gly Gly His Ala Val Ser Arg Gly Ser Ala Lys
 50                  55                  60

Leu Arg Trp Leu Val Glu Arg Gly Tyr Leu Gln Pro Tyr Gly Lys Val
 65                  70                  75                  80

Ile Asp Leu Gly Cys Gly Arg Gly Gly Trp Ser Tyr Tyr Val Ala Thr
                     85                  90                  95

Ile Arg Lys Val Gln Glu Val Lys Gly Tyr Thr Lys Gly Gly Pro Gly
                    100                 105                 110

His Glu Glu Pro Val Leu Val Gln Ser Tyr Gly Trp Asn Ile Val Arg
                115                 120                 125

Leu Lys Ser Gly Val Asp Val Phe His Met Ala Ala Glu Pro Cys Asp
130                 135                 140

Thr Leu Leu Cys Asp Ile Gly Glu Ser Ser Ser Pro Glu Val Glu
145                 150                 155                 160

Glu Ala Arg Thr Leu Arg Val Leu Ser Met Val Gly Asp Trp Leu Glu
                165                 170                 175

Lys Arg Pro Gly Ala Phe Cys Ile Lys Val Leu Cys Pro Tyr Thr Ser
                180                 185                 190

Thr Met Met Glu Thr Leu Glu Arg Leu Gln Arg Arg Tyr Gly Gly Gly
            195                 200                 205

Leu Val Arg Val Pro Leu Ser Arg Asn Ser Thr His Glu Met Tyr Trp
210                 215                 220

Val Ser Gly Ala Lys Ser Asn Thr Ile Lys Ser Val Ser Thr Thr Ser
225                 230                 235                 240

Gln Leu Leu Leu Gly Arg Met Asp Gly Pro Arg Arg Pro Val Lys Tyr
                245                 250                 255

Glu Glu Asp Val Asn Leu Gly Ser Gly Thr Arg Ala Val Val Ser Cys
                260                 265                 270

Ala Glu Ala Pro Asn Met Lys Ile Ile Gly Asn Arg Ile Glu Arg Ile
            275                 280                 285

Arg Ser Glu His Ala Glu Thr Trp Phe Phe Asp Glu Asn His Pro Tyr
290                 295                 300

Arg Thr Trp Ala Tyr His Gly Ser Tyr Glu Ala Pro Thr Gln Gly Ser
305                 310                 315                 320

Ala Ser Ser Leu Ile Asn Gly Val Val Arg Leu Leu Ser Lys Pro Trp
                325                 330                 335

Asp Val Val Thr Gly Val Thr Gly Ile Ala Met Thr Asp Thr Thr Pro
                340                 345                 350

Tyr Gly Gln Gln Arg Val Phe Lys Glu Lys Val Asp Thr Arg Val Pro
            355                 360                 365

Asp Pro Gln Glu Gly Thr Arg Gln Val Met Ser Met Val Ser Ser Trp
            370                 375                 380

Leu Trp Lys Glu Leu Gly Lys His Lys Arg Pro Arg Val Cys Thr Lys
385                 390                 395                 400

Glu Glu Phe Ile Asn Lys Val Arg Ser Asn Ala Ala Leu Gly Ala Ile
                405                 410                 415

Phe Glu Glu Glu Lys Glu Trp Lys Thr Ala Val Glu Ala Val Asn Asp
            420                 425                 430

Pro Arg Phe Trp Ala Leu Val Asp Lys Glu Arg Glu His His Leu Arg
            435                 440                 445

Gly Glu Cys Gln Ser Cys Val Tyr Asn Met Met Gly Lys Arg Glu Lys
450                 455                 460
```

-continued

```
Lys Gln Gly Glu Phe Gly Lys Ala Lys Gly Ser Arg Ala Ile Trp Tyr
465                 470                 475                 480
Met Trp Leu Gly Ala Arg Phe Leu Glu Phe Glu Ala Leu Gly Phe Leu
                485                 490                 495
Asn Glu Asp His Trp Met Gly Arg Glu Asn Ser Gly Gly Gly Val Glu
                500                 505                 510
Gly Leu Gly Leu Gln Arg Leu Gly Tyr Val Leu Glu Glu Met Ser Arg
                515                 520                 525
Ile Pro Gly Gly Arg Met Tyr Ala Asp Asp Thr Ala Gly Trp Asp Thr
        530                 535                 540
Arg Ile Ser Arg Phe Asp Leu Glu Asn Glu Ala Leu Ile Thr Asn Gln
545                 550                 555                 560
Met Glu Lys Gly His Arg Ala Leu Ala Leu Ala Ile Ile Lys Tyr Thr
                565                 570                 575
Tyr Gln Asn Lys Val Val Lys Val Leu Arg Pro Ala Glu Lys Gly Lys
                580                 585                 590
Thr Val Met Asp Ile Ile Ser Arg Gln Asp Gln Arg Gly Ser Gly Gln
        595                 600                 605
Val Val Thr Tyr Ala Leu Asn Thr Phe Thr Asn Leu Val Val Gln Leu
        610                 615                 620
Ile Arg Asn Met Glu Ala Glu Glu Val Leu Glu Met Gln Asp Leu Trp
625                 630                 635                 640
Leu Leu Arg Arg Ser Glu Lys Val Thr Asn Trp Leu Gln Ser Asn Gly
                645                 650                 655
Trp Asp Arg Leu Lys Arg Met Ala Val Ser Gly Asp Asp Cys Val Val
                660                 665                 670
Lys Pro Ile Asp Asp Arg Phe Ala His Ala Leu Arg Phe Leu Asn Asp
                675                 680                 685
Met Gly Lys Val Arg Lys Asp Thr Gln Glu Trp Lys Pro Ser Thr Gly
        690                 695                 700
Trp Asp Asn Trp Glu Glu Val Pro Phe Cys Ser His His Phe Asn Lys
705                 710                 715                 720
Leu His Leu Lys Asp Gly Arg Ser Ile Val Val Pro Cys Arg His Gln
                725                 730                 735
Asp Glu Leu Ile Gly Arg Ala Arg Val Ser Pro Gly Ala Gly Trp Ser
                740                 745                 750
Ile Arg Glu Thr Ala Cys Leu Ala Lys Ser Tyr Ala Gln Met Trp Gln
                755                 760                 765
Leu Leu Tyr Phe His Arg Arg Asp Leu Arg Leu Met Ala Asn Ala Ile
                770                 775                 780
Cys Ser Ser Val Pro Val Asp Trp Val Pro Thr Gly Arg Thr Thr Trp
785                 790                 795                 800
Ser Ile His Gly Lys Gly Glu Trp Met Thr Thr Glu Asp Met Leu Val
                805                 810                 815
Val Trp Asn Arg Val Trp Ile Glu Glu Asn Asp His Met Glu Asp Lys
                820                 825                 830
Thr Pro Val Thr Lys Trp Thr Asp Ile Pro Tyr Leu Gly Lys Arg Glu
                835                 840                 845
Asp Leu Trp Cys Gly Ser Leu Ile Gly His Arg Pro Arg Thr Thr Trp
                850                 855                 860
Ala Glu Asn Ile Lys Asn Thr Val Asn Met Val Arg Arg Ile Ile Gly
865                 870                 875                 880
Asp Glu Glu Lys Tyr Met Asp Tyr Leu Ser Thr Gln Val Arg Tyr Leu
```

Gly Glu Glu Gly
            900

<210> SEQ ID NO 14
<211> LENGTH: 7015
<212> TYPE: DNA
<213> ORGANISM: Artificial Sequence
<220> FEATURE:
<223> OTHER INFORMATION: plasmid

<400> SEQUENCE: 14

| | | | | | |
|---|---|---|---|---|---|
| gactcttcgc | gatgtacggg | ccagatatac | gcgttaactg | cagtctagat | tatgcgaaag | 60 |
| gccatcctga | cggatggcct | ttttgtttaa | acggatccgc | gacattgatt | attgactagt | 120 |
| tattaatagt | aatcaattac | ggggtcatta | ggggactttc | cggggacttt | cctccccacg | 180 |
| cgggggactt | tccgccacgg | gcggggactt | tccggggact | ttccgttcat | agcccatata | 240 |
| tggagttccg | cgttacataa | cttacggtaa | atggcccgcc | tggctgaccg | cccaacgacc | 300 |
| cccgcccatt | gacgtcaata | atgacgtatg | ttcccatagt | aacgccaata | gggactttcc | 360 |
| attgacgtca | atgggtggac | tatttacggt | aaactgccca | cttggcagta | catcaagtgt | 420 |
| atcatatgcc | aagtacgccc | cctattgacg | tcaatgacgg | taaatggccc | gcctggcatt | 480 |
| atgcccagta | catgacctta | tgggactttc | ctacttggca | gtacatctac | gtattagtca | 540 |
| tcgctattac | catggtgatg | cggttttggc | agtacatcaa | tgggcgtgga | tagcggtttg | 600 |
| actcacgggg | atttccaagt | ctccacccca | ttgacgtcaa | tgggagtttg | ttttggcacc | 660 |
| aaaatcaacg | ggactttcca | aaatgtcgta | acaactccgc | cccattgacg | caaatgggcg | 720 |
| gtaggcgtgt | acggtgggag | gtctatataa | gcagagctct | ctggctaact | agagaaccca | 780 |
| ctgcttactg | gcttatcgaa | attaatacga | ctcactatag | ggagacccaa | gctggctagc | 840 |
| gtttaaactt | aagcttggta | ccgagctcgg | atccactagt | ccagtgtggt | ggaattctgc | 900 |
| agatatccag | cacagtggcg | gccgctcgag | aatgcttcga | gcagacatga | taagatacat | 960 |
| tgatgagttt | ggacaaacca | caactagaat | gcagtgaaaa | aaatgcttta | tttgtgaaat | 1020 |
| ttgtgatgct | attgctttat | ttgtaaccat | tataagctgc | aataaacaag | ttaacaacaa | 1080 |
| caattgcatt | cattttatgt | ttcaggttca | ggggagatg | tgggaggttt | tttaaagcaa | 1140 |
| gtaaaacctc | tacaaatgtg | gtaaaatccg | ataaggatcg | atccgggca | tgcaaccagc | 1200 |
| tgtggaatgt | gtgtcagtta | gggtgtggaa | agtccccagg | ctccccagca | ggcagaagta | 1260 |
| tgcaaagcat | gtgggatgc | ggtgggctct | atggcttcta | ctgggcggtt | ttatggacag | 1320 |
| caagcgaacc | ggaattgcca | gctggggcgc | cctctggtaa | ggttgggaag | ccctgcaaag | 1380 |
| taaactggat | ggctttctcg | ccgccaagga | tctgtcgacc | cctagatttc | agtgcaattt | 1440 |
| atctcttcaa | atgtagcacc | tgaagtcagc | cccatacgat | ataagttgtt | ggaagatcta | 1500 |
| gcccgcctaa | tgagcgggct | tttttttaat | tcgcaattcc | ccgatgcata | atgtgcctgt | 1560 |
| caaatggacg | aagcagggat | tctgcaaacc | ctatgctact | ccgtcaagcc | gtcaattgtc | 1620 |
| tgattcgtta | ccaattatga | caacttgacg | gctacatcat | tcacttttc | ttcacaaccg | 1680 |
| gcacgaaact | cgctcgggct | ggccccggtg | cattttttaa | atactcgcga | gaaatagagt | 1740 |
| tgatcgtcaa | aaccaacatt | gcgaccgacg | gtggcgatag | gcatccgggt | agtgctcaaa | 1800 |
| agcagcttcg | cctgactaat | gcgttggtcc | tcgcgccagc | ttaagacgct | aatccctaac | 1860 |
| tgctggcgga | aaagatgtga | cagacgcgac | ggcgacaagc | aaacatgctg | tgcgacgctg | 1920 |

```
gcgatatcaa aattgctgtc tgccaggtga tcgctgatgt actgacaagc ctcgcgtacc   1980
cgattatcca tcggtggatg gagcgactcg ttaatcgctt ccatgcgccg cagtaacaat   2040
tgctcaagca gatttatcgc cagcagctcc gaatagcgcc cttccccttg cccggcgtta   2100
atgatttgcc caaacaggtc gctgaaatgc ggctggtgcg cttcatccgg gcgaaagaaa   2160
cccgtattgg caaatattga cggccagtta agccattcat gccagtaggc gcgcggacga   2220
aagtaaaccc actggtgata ccattcgcga gcctccggat gacgaccgta gtgatgaatc   2280
tctcctggcg ggaacagcaa aatatcaccc ggtcggcaga caaattctcg tccctgattt   2340
ttcaccaccc cctgaccgcg aatggtgaga ttgagaatat aacctttcat tcccagcggt   2400
cggtcgataa aaaaatcgag ataaccgttg gcctcaatcg gcgttaaacc cgccaccaga   2460
tgggcgttaa acgagtatcc cggcagcagg ggatcatttt gcgcttcagc catacttttc   2520
atactcccac cattcagaga agaaaccaat tgtccatatt gcatcagaca ttgccgtcac   2580
tgcgtctttt actggctctt ctcgctaacc caaccggtaa ccccgcttat taaaagcatt   2640
ctgtaacaaa gcgggaccaa agccatgaca aaaacgcgta acaaaagtgt ctataatcac   2700
ggcagaaaag tccacattga ttatttgcac ggcgtcacac tttgctatgc catagcattt   2760
ttatccataa gattagcgga tcctacctga cgctttttat cgcaactctc tactgtttct   2820
ccatacccgt ttttttgggc tagcgaattc tgagaacaaa ctaagtggat aaatttcgtg   2880
ttcaggggcc aacgaagctc cagggcgaag tcacaatttc cggcgctaaa aatgctgctc   2940
tgcctatcct ttttgccgca ctactggcgg aagaaccggt agagatccag aacgtcccga   3000
aactgaaaga cgtcgataca tcaatgaagc tgctaagcca gctgggtgcg aaagtagaac   3060
gtaatggttc tgtgcatatt gatgcccgcg acgttaatgt attctgcgca ccttacgatc   3120
tggttaaaac catgcgtgct tctatctggg cgctggggcc gctggtagcg cgctttggtc   3180
aggggcaagt ttcactacct ggcggttgta cgatcggtgc gcgtccggtt gatctacaca   3240
tttctggcct cgaacaatta ggcgcgacca tcaaactgga agaaggttac gttaaagctt   3300
ccgtcgatgg tcgtttgaaa ggtgcacata tcgtgatgga taaagtcagc gttggcgcaa   3360
cggtgaccat catgtgtgct gcaaccctgg cggaaggcac cacgattatt gaaaacgcag   3420
cgcgtgaacc ggaaatcgtc gataccgcga acttcctgat tacgctgggt gcgaaaatta   3480
gcggtcaggg caccgatcgt atcgtcatcg aaggtgtgga acgtttaggc ggcggtgtct   3540
atcgcgttct gccggatcgt atcgaaaccg gtactttcct ggtggcggcg gcgatttctc   3600
gcggcaaaat tatctgccgt aacgcgcagc cagatactct cgacgccgtg ctggcgaaac   3660
tgcgtgacgc tggagcggac atcgaagtcg gcgaagactg gattagcctg gatatgcatg   3720
gcaaacgtcc gaaggctgtt aacgtacgta ccgcgccgca tccggcattc ccgaccgata   3780
tgcaggccca gttcacgctg ttgaacctgg tggcagaagg gaccgggttt atcaccgaaa   3840
cggtctttga aaaccgcttt atgcatgtgc cagagctgag ccgtatgggc gcgcacgccg   3900
aaatcgaaag caataccgtt atttgtcacg gtgttgaaaa actttctggc gcacaggtta   3960
tggcaaccga tctgcgtgca tcagcaagcc tggtgctggc tggctgtatt gcggaaggga   4020
cgacggtggt tgatcgtatt tatcacatcg atcgtggcta cgaacgcatt gaagacaaac   4080
tgcgcgcttt aggtgcaaat attgagcgtg tgaaggcga ataagaattc aggaaaaaaa   4140
cgctgtgaaa aatgttggtt ttatcggctg gcgcggaatg gtcggctctg ttctcatgca   4200
acgcatggta gaggagcgcg atttcgacgc tattcgccct gttttctttt ctacctccca   4260
gtttggacag gcggcgccca ccttcggcga caccctccacc ggcacgctac aggacgcttt   4320
```

```
tgatctggat gcgctaaaag cgctcgatat catcgtgacc tgccagggcg gcgattatac    4380
caacgaaatt tatccaaagc tgcgcgaaag cggatggcag ggttactgga ttgatgcggc    4440
ttctacgctg cgcatgaaag atgatgccat tattattctc gacccggtca accaggacgt    4500
gattaccgac ggcctgaaca atggcgtgaa gacctttgtg ggcggtaact gtaccgttag    4560
cctgatgttg atgtcgctgg gcggtctctt tgcccataat ctcgttgact gggtatccgt    4620
cgcgacctat caggccgcct ccggcggcgg cgcgcgccat atgcgcgagc tgttaaccca    4680
gatgggtcag ttgtatggcc atgtcgccga tgaactggcg acgccgtctt ccgcaattct    4740
tgatattgaa cgcaaagtta cggcattgac ccgcagcggc gagctgccgg ttgataactt    4800
tggcgtaccg ctggcgggaa gcctgatccc ctggatcgac aaacagctcg ataacggcca    4860
gagccgcgaa gagtggaaag gccaggcgga aaccaacaag attctcaata ctgcctctgt    4920
gattccggtt gatggtttgt gtgtgcgcgt cggcgcgctg cgctgtcaca gccaggcgtt    4980
caccatcaag ctgaaaaaag aggtatccat tccgacggtg gaagaactgc tggcggcaca    5040
taatccgtgg gcgaaagtgg tgccgaacga tcgtgatatc actatgcgcg aattaacccc    5100
ggcggcggtg accggcacgt tgactacgcc ggttggtcgt ctgcgtaagc tgaacatggg    5160
gccagagttc ttgtcggcgt ttaccgtagg cgaccagttg ttatggggcg ccgccgagcc    5220
gctgcgtcga atgctgcgcc agttggcgta gtctagctgc acgataccgt cgacttgtac    5280
atagactcgc tccgaaatta agaacactt aaattatcta ctaaaggaat ctttagtcaa    5340
gtttatttaa gatgacttaa ctatgaatac acaattgatg ggtgagcgta ggatcttcca    5400
ttattgaagc atttatcagg gttattgtct catgagcttg gctgttttgg cggatgagag    5460
aagattttca gcctgataca gattaaatca gaacgcagaa gcggtctgat aaaacagttt    5520
gcctggcggc agtagcgcgg tggtcccacc tgaccccatg ccgaactcag aagtgaaacg    5580
ccgtagcgcc gatggtagtg tggggtctcc ccatgcgaga gtagggaact gccaggcatc    5640
aaataaaacg aaaggctcag tcgaaagact gggcctttcg ttttatctgt tgtttgtcgg    5700
tgaacgctct cctgagtagg acaaatccgc cgggagcgga tttgaacgtt gcgaagcaac    5760
ggcccggagg gtggcgggca ggacgcccgc cataaactgc caggcatcaa attaagcaga    5820
aggccatcct gacggatggc cttttttgcgt ttctacaaac tcttttttgtt tatttttcta    5880 aatacattca aatatgtatc cgctcatgag acaataaccc tgataaatgc ttcaataatg    5940
gaagatcttc caacatcaca ggtaaacaga acgtcgggt cgatcgggaa attctttccc    6000
ggacggcgcg gggttgggca agccgcaggc gcgtcagtgc tttagcggg tgtcggggca    6060 gccctgaacc agtcacggga tcgatctgtg cggtatttca caccgcatac aggtggcact    6120
tttcggggaa atgtgcgcgg aacccctatt tgtttatttt tctaaataca ttcaaatatg    6180
tatccgctca tgagacaata accctgataa atgcttcaat aatagcacgt gctaaaactt    6240 cattttaat ttaaaggat ctaggtgaag atcctttttg ataatctcat gaccaaaatc    6300
ccttaacgtg agttttcgtt ccactgagcg tcagaccccg tagaaaagat caaaggatct    6360
tcttgagatc cttttttttct gcgcgtaatc tgctgcttgc aaacaaaaaa accaccgcta    6420
ccagcggtgg tttgtttgcc ggatcaagag ctaccaactc ttttttccgaa ggtaactggc    6480 ttcagcagag cgcagatacc aaatactgtc cttctagtgt agccgtagtt aggccaccac    6540
ttcaagaact ctgtagcacc gcctacatac ctcgctctgc taatcctgtt accagtggct    6600
gctgccagtg gcgataagtc gtgtcttacc gggttggact caagacgata gttaccggat    6660
```

| | | |
|---|---|---|
| aaggcgcagc ggtcgggctg aacgggggt tcgtgcacac agcccagctt ggagcgaacg | 6720 | |
| acctacaccg aactgagata cctacagcgt gagctatgag aaagcgccac gcttcccgaa | 6780 | |
| gggagaaagg cggacaggta tccggtaagc ggcagggtcg aacaggaga gcgcacgagg | 6840 | |
| gagcttccag ggggaaacgc ctggtatctt tatagtcctg tcgggtttcg ccacctctga | 6900 | |
| cttgagcgtc gattttgtg atgctcgtca gggggcgga gcctatggaa aaacgccagc | 6960 | |
| aacgcggcct ttttacggtt cctgggcttt tgctggcctt ttgctcacat gttct | 7015 | |

```
<210> SEQ ID NO 15
<211> LENGTH: 288
<212> TYPE: DNA
<213> ORGANISM: Zika Virus

<400> SEQUENCE: 15
```

| | | |
|---|---|---|
| atgaaaaagg cggaggtcac tagacgtggg agtgcatact atatgtactt ggacagaaac | 60 | |
| gatgctgggg aggccatatc ttttccaacc acattgggga tgaataagtg ttatatacag | 120 | |
| atcatggatc ttggacacat gtgtgatgcc accatgagct atgaatgccc tatgctggat | 180 | |
| gaggggtgg aaccagatga cgtcgattgt tggtgcaaca cgacgtcaac ttgggttgtg | 240 | |
| tacggaaacct gccatcacaa aaaaggtgaa gcacggagat ctagaaga | 288 | |

```
<210> SEQ ID NO 16
<211> LENGTH: 288
<212> TYPE: DNA
<213> ORGANISM: Artificial Sequence
<220> FEATURE:
<223> OTHER INFORMATION: encodes prM

<400> SEQUENCE: 16
```

| | | |
|---|---|---|
| atgaaaaagg cggaggtcac tcgtcgtggt agcgcatact atatgtacct ggaccgcaac | 60 | |
| gatgctggcg aggccatctc ttttccaacc accttgggta tgaataagtg ttatatccag | 120 | |
| atcatggatc tgggccacat gtgtgatgcc accatgagct atgaatgccc tatgctggat | 180 | |
| gaggggtgg aaccagatga cgtcgattgt tggtgcaaca cgacgtcaac ttgggttgtg | 240 | |
| tacggtacct gccatcacaa aaaaggtgaa gcacgccgct ctcgccgc | 288 | |

```
<210> SEQ ID NO 17
<211> LENGTH: 288
<212> TYPE: DNA
<213> ORGANISM: Artificial Sequence
<220> FEATURE:
<223> OTHER INFORMATION: encodes prM

<400> SEQUENCE: 17
```

| | | |
|---|---|---|
| atgaaaaaag cggaagttac ccgtcgtggt tctgcgtact acatgtacct ggatcgcaac | 60 | |
| gatgcgggtg aagcgatctc tttcccgacc accctgggta tgaacaaatg ctacatccag | 120 | |
| atcatggatc tgggtcacat gtgcgatgcc accatgtctt acgaatgccc gatgctggat | 180 | |
| gaaggtgttg aaccgatga tgttgattgc tggtgcaaca ccacctctac ttgggttgtt | 240 | |
| tacggtacct gccaccacaa aaaaggtgaa gcgcgtcgtt ctcgtcgt | 288 | |

```
<210> SEQ ID NO 18
<211> LENGTH: 96
<212> TYPE: PRT
<213> ORGANISM: Zika Virus

<400> SEQUENCE: 18

Met Lys Lys Ala Glu Val Thr Arg Arg Gly Ser Ala Tyr Tyr Met Tyr
```

```
             1               5                 10                   15
           Leu Asp Arg Asn Asp Ala Gly Glu Ala Ile Ser Phe Pro Thr Thr Leu
                            20                  25                  30
           Gly Met Asn Lys Cys Tyr Ile Gln Ile Met Asp Leu Gly His Met Cys
                            35                  40                  45
           Asp Ala Thr Met Ser Tyr Glu Cys Pro Met Leu Asp Glu Gly Val Glu
                        50                  55                  60
           Pro Asp Asp Val Asp Cys Trp Cys Asn Thr Thr Ser Thr Trp Val Val
            65                  70                  75                  80
           Tyr Gly Thr Cys His His Lys Lys Gly Glu Ala Arg Arg Ser Arg Arg
                            85                  90                  95

<210> SEQ ID NO 19
<211> LENGTH: 1518
<212> TYPE: DNA
<213> ORGANISM: Zika Virus

<400> SEQUENCE: 19
atgaaaatca ggtgcatagg agtcagcaat agggactttg tggaaggtat gtcaggtggg      60 acttggttg atgttgtctt ggaacatgga ggttgtgtca ccgtaatggc acaggacaaa     120
ccgactgtcg acatagagct ggttacaaca acagtcagca catggcgga ggtaagatcc      180 tactgctatg aggcatcaat atcagacatg gcttctgaca gccgctgccc aacacaaggt     240
gaagcctacc ttgacaagca atcagacact caatatgtct gcaaagaac gttagtggac      300 agaggctggg gaaatggatg tggacttttt ggcaaaggga gcctggtgac atgcgctaag     360
tttgcatgct ccaagaaaat gaccgggaag agcatccagc cagagaatct ggagtaccgg     420
ataatgctgt cagttcatgg ctcccagcac agtgggatga tcgttaatga cacaggacat      480
gaaactgatg agaatagagc gaaagttgag ataacgccca ttcaccgag agccgaagcc     540 accctggggg gttttggaag cctaggactt gattgtgaac cgaggacagg ccttgacttt      600
tcagatttgt attacttgac tatgaataac aagcactggt tggttcacaa ggagtggttc     660
cacgacattc cattaccttg gcacgctggg gcagacaccg aactccaca ctggaacaac       720 aaagaagcac tggtagagtt caaggacgca catgccaaaa ggcaaactgt cgtggttcta    780
gggagtcaag aaggagcagt tcacacggcc cttgctggag ctctggaggc tgagatggat     840
ggtgcaaagg aaggctgtc ctctggccac ttgaaatgtc gcctgaaaat ggataaactt      900
agattgaagg gcgtgtcata ctccttgtgt actgcagcgt tcacattcac caagatcccg     960
gctgaaacac tgcacgggac agtcacagtg gagttacagt acgcagggac agatggacct    1020
tgcaaggttc agctcagat ggcggtggac atgcaaactc tgaccccagt gggaggttg      1080 ataaccgcta accccgtaat cactgaaagc actgagaact ctaagatgat gctggaactt    1140
gatccaccat ttgggactc ttacattgtc ataggagtcg gggagaagaa gatcacccac     1200
cactggcaca ggagtggcag caccattgga aaagcatttg aagccactgt gagaggtgcc    1260
aagagaatgg cagtcttggg agacacagcc tgggactttg gatcagttgg aggcgctctc    1320
aactcattgg gcaagggcat ccatcaaatt tttggagcag ctttcaaatc attgtttgga    1380
ggaatgtcct ggttctcaca aattctcatt ggaacgttgc tgatgtggtt gggtctgaac    1440
acaaagaatg gatctatttc ccttatgtgc ttggccttag ggggagtgtt gatcttctta    1500
tccacagccg tctctgct                                                  1518

<210> SEQ ID NO 20
```

```
<211> LENGTH: 1518
<212> TYPE: DNA
<213> ORGANISM: Artificial Sequence
<220> FEATURE:
<223> OTHER INFORMATION: encodes E protein
<400> SEQUENCE: 20
atgaaaatcc gctgcatcgg tgtcagcaat cgtgactttg tggaaggtat gtccggtggt 60
acttgggttg atgttgtcct ggaacatggc ggttgtgtca ccgtaatggc acaggacaaa 120
ccgactgtcg acatcgagct ggttaccacc accgtcagca acatggcgga ggtacgttcc 180
tactgctatg aggcatccat ctccgacatg gcttctgaca gccgctgccc aacccaaggt 240
gaagcctacc ttgacaagca atccgacact caatatgtct gcaaacgtac gctggtggac 300
cgtggctggg gcaatggttg tggccttttt ggtaaaggga gcctggtgac ctgcgctaag 360
tttgcatgct ccaagaaaat gaccggcaag agcatccagc cagagaatct ggagtaccgc 420
atcatgctgt cagttcatgg ctcccagcac agtgggatga tcgttcagga cacaggtcat 480
gaaactgatg agaatcgcgc gaaagttgag atcacgccca attcaccgcg tgccgaagcc 540
accctggggg gttttggtag cctaggtctt gattgtgaac cgcgtacagg ccttgacttt 600
tcagatttgt attacttgac tatgaataac aagcactggt tggttcacaa ggagtggttc 660
cacgacattc cattaccttg gcacgctggg gcagacaccg gtactccaca ctggaacaac 720
aaagaagcac tggtagagtt caaggacgca catgccaaac gtcaaactgt cgtggttctg 780
gggagtcaag aaggtgcagt tcacacggcc cttgctggtg ctctggaggc tgagatggat 840
ggtgcaaagg gccgcctgtc ctctggccac ttgaaatgtc gcctgaaaat ggataaactt 900
cgtttgaagg gtgtgtcata ctccttgtgt actgcagcgt tcacattcac caagatcccg 960
gctgaaacac tgcacgggac agtcacagtg gagttacagt acgcagggac agatggtcct 1020
tgcaaggttc cagctcagat ggcggtggac atgcaaactc tgaccccagt tgggcgtttg 1080
atcaccgcta acccggtaat cactgaaagc actgagaact ctaagatgat gctggaactt 1140
gatccaccat ttggggactc ttacattgtc atcggtgtcg gggagaagaa gatcacccac 1200
cactggcacc gcagtggcag caccattggt aaagcatttg aagccactgt gcgtggtgcc 1260
aagcgtatgg cagtcttggg tgacacagcc tgggactttg gttcagttgg cggcgctctc 1320
aactcattgg gcaagggcat ccatcaaatt tttggcgcag ctttcaaatc attgtttggt 1380
ggtatgtcct ggttctcaca aattctcatt ggaacgttgc tgatgtggtt gggtctgaac 1440
acaaaggagg gctctatttc ccttatgtgc ttggccttag gggtgtgtt gatcttctta 1500
tccacagccg tctctgct 1518

<210> SEQ ID NO 21
<211> LENGTH: 1518
<212> TYPE: DNA
<213> ORGANISM: Artificial Sequence
<220> FEATURE:
<223> OTHER INFORMATION: encodes E protein
<400> SEQUENCE: 21
atgaaaatcc gctgcatcgg tgtttctaac cgtgacttcg ttgaaggtat gtctggtggt 60
acctgggttg atgttgttct ggaacacggt ggttgcgtta ccgttatggc gcaggataaa 120
ccgaccgttg atatcgaact ggttaccacc accgtttcta acatggcgga agttcgttct 180
tactgctacg aagcgtctat ctctgatatg gcgtctgata gccgttgccc gacccagggt 240
gaagcgtacc tggataaaca gtctgatacc cagtacgttt gcaaacgtac cctggttgat 300
```

-continued

```
cgtggttggg gcaacggttg cggtctgttc ggtaaaggtt ctctggttac ctgcgctaaa    360
ttcgcatgct ctaaaaaaat gaccggtaaa agcatccagc cggaaaacct ggaataccgt    420
atcatgctgt ctgttcacgg ctcccagcac tctggtatga tcgttaacga taccggtcac    480
gaaaccgatg aaaaccgtgc gaaagttgaa atcaccccga actctccgcg tgccgaagcc    540
accctgggtg gtttcggttc tctgggtctg gattgcgaac cgcgtaccgg tctggatttc    600
tctgatctgt actacctgac catgaacaac aagcactggc tggttcacaa ggaatggttc    660
cacgatatcc cgctgccgtg gcacgctggt gcagataccg gtaccccgca ctggaacaac    720
aaagaagcac tggttgaatt caagatgca cacgccaaac gtcagaccgt tgttgttctg    780
ggttctcagg aaggtgcagt tcacaccgcc ctggctggtg ctctggaagc tgaaatggat    840
ggtgcaaaag gtcgtctgtc ttctggtcac ctgaaatgcc gtctgaaaat ggataaactg    900
cgtctgaaag gtgtttctta ctctctgtgc accgcagcgt tcaccttcac caaaatcccg    960
gctgaaaccc tgcacggtac cgttaccgtg gaactgcagt acgcaggtac cgatggtccg   1020
tgcaaagttc cggctcagat ggcggtggat atgcagaccc tgaccccggt ggtcgtctg   1080
atcaccgcta accggttat caccgaatct accgaaaact ctaaaatgat gctggaactg   1140
gatccgccat tcggtgattc ttacatcgtt atcggtgtgg gtgaaaaaaa aatcacccac   1200
aaacgtatgg cagttctggg tgatacagcc tgggatttcg gttctgttgg tggtgctctg   1260
aaacgtatgg cagttctggg tgatacagcc tgggatttcg gttctgttgg tggtgctctg   1320
aactctctgg gtaagggtat ccaccagatc ttcggtgcag ctttcaaatc tctgttcggt   1380
ggtatgtctt ggttctctca aatcctgatc ggtaccctgc tgatgtggct gggtctgaac   1440
accaaaaacg ttctatctc tctgatgtgc ctggccctgg tggtgttct gatcttcctg   1500
tctaccgccg tttctgct                                                 1518
```

<210> SEQ ID NO 22
<211> LENGTH: 506
<212> TYPE: PRT
<213> ORGANISM: Zika Virus

<400> SEQUENCE: 22

```
Met Lys Ile Arg Cys Ile Gly Val Ser Asn Arg Asp Phe Val Glu Gly
1               5                   10                  15
Met Ser Gly Gly Thr Trp Val Asp Val Val Leu Glu His Gly Gly Cys
            20                  25                  30
Val Thr Val Met Ala Gln Asp Lys Pro Thr Val Asp Ile Glu Leu Val
        35                  40                  45
Thr Thr Thr Val Ser Asn Met Ala Glu Val Arg Ser Tyr Cys Tyr Glu
    50                  55                  60
Ala Ser Ile Ser Asp Met Ala Ser Asp Ser Arg Cys Pro Thr Gln Gly
65                  70                  75                  80
Glu Ala Tyr Leu Asp Lys Gln Ser Asp Thr Gln Tyr Val Cys Lys Arg
                85                  90                  95
Thr Leu Val Asp Arg Gly Trp Gly Asn Gly Cys Gly Leu Phe Gly Lys
            100                 105                 110
Gly Ser Leu Val Thr Cys Ala Lys Phe Ala Cys Ser Lys Lys Met Thr
        115                 120                 125
Gly Lys Ser Ile Gln Pro Glu Asn Leu Glu Tyr Arg Ile Met Leu Ser
    130                 135                 140
Val His Gly Ser Gln His Ser Gly Met Ile Val Asn Asp Thr Gly His
```

```
            145                 150                 155                 160
        Glu Thr Asp Glu Asn Arg Ala Lys Val Glu Ile Thr Pro Asn Ser Pro
                        165                 170                 175

Arg Ala Glu Ala Thr Leu Gly Gly Phe Gly Ser Leu Gly Leu Asp Cys
                    180                 185                 190

Glu Pro Arg Thr Gly Leu Asp Phe Ser Asp Leu Tyr Tyr Leu Thr Met
                195                 200                 205

Asn Asn Lys His Trp Leu Val His Lys Glu Trp Phe His Asp Ile Pro
                210                 215                 220

Leu Pro Trp His Ala Gly Ala Asp Thr Gly Thr Pro His Trp Asn Asn
        225                 230                 235                 240

Lys Glu Ala Leu Val Glu Phe Lys Asp Ala His Ala Lys Arg Gln Thr
                        245                 250                 255

Val Val Val Leu Gly Ser Gln Glu Gly Ala Val His Thr Ala Leu Ala
                    260                 265                 270

Gly Ala Leu Glu Ala Glu Met Asp Gly Ala Lys Gly Arg Leu Ser Ser
                275                 280                 285

Gly His Leu Lys Cys Arg Leu Lys Met Asp Lys Leu Arg Leu Lys Gly
                290                 295                 300

Val Ser Tyr Ser Leu Cys Thr Ala Ala Phe Thr Phe Thr Lys Ile Pro
        305                 310                 315                 320

Ala Glu Thr Leu His Gly Thr Val Thr Val Glu Leu Gln Tyr Ala Gly
                        325                 330                 335

Thr Asp Gly Pro Cys Lys Val Pro Ala Gln Met Ala Val Asp Met Gln
                    340                 345                 350

Thr Leu Thr Pro Val Gly Arg Leu Ile Thr Ala Asn Pro Val Ile Thr
                355                 360                 365

Glu Ser Thr Glu Asn Ser Lys Met Met Leu Glu Leu Asp Pro Pro Phe
                370                 375                 380

Gly Asp Ser Tyr Ile Val Ile Gly Val Gly Glu Lys Lys Ile Thr His
        385                 390                 395                 400

His Trp His Arg Ser Gly Ser Thr Ile Gly Lys Ala Phe Glu Ala Thr
                        405                 410                 415

Val Arg Gly Ala Lys Arg Met Ala Val Leu Gly Asp Thr Ala Trp Asp
                    420                 425                 430

Phe Gly Ser Val Gly Gly Ala Leu Asn Ser Leu Gly Lys Gly Ile His
                435                 440                 445

Gln Ile Phe Gly Ala Ala Phe Lys Ser Leu Phe Gly Gly Met Ser Trp
                450                 455                 460

Phe Ser Gln Ile Leu Ile Gly Thr Leu Leu Met Trp Leu Gly Leu Asn
        465                 470                 475                 480

Thr Lys Asn Gly Ser Ile Ser Leu Met Cys Leu Ala Leu Gly Gly Val
                        485                 490                 495

Leu Ile Phe Leu Ser Thr Ala Val Ser Ala
                    500                 505

<210> SEQ ID NO 23
<211> LENGTH: 506
<212> TYPE: PRT
<213> ORGANISM: Zika Virus

<400> SEQUENCE: 23

Met Lys Ile Arg Cys Ile Gly Val Ser Asn Arg Asp Phe Val Glu Gly
1               5                   10                  15
```

-continued

```
Met Ser Gly Gly Thr Trp Val Asp Val Val Leu Glu His Gly Gly Cys
             20                  25                  30
Val Thr Val Met Ala Gln Asp Lys Pro Thr Val Asp Ile Glu Leu Val
         35                  40                  45
Thr Thr Thr Val Ser Asn Met Ala Glu Val Arg Ser Tyr Cys Tyr Glu
     50                  55                  60
Ala Ser Ile Ser Asp Met Ala Ser Asp Ser Arg Cys Pro Thr Gln Gly
 65                  70                  75                  80
Glu Ala Tyr Leu Asp Lys Gln Ser Asp Thr Gln Tyr Val Cys Lys Arg
                 85                  90                  95
Thr Leu Val Asp Arg Gly Trp Gly Asn Gly Cys Gly Leu Phe Gly Lys
            100                 105                 110
Gly Ser Leu Val Thr Cys Ala Lys Phe Ala Cys Ser Lys Lys Met Thr
        115                 120                 125
Gly Lys Ser Ile Gln Pro Glu Asn Leu Glu Tyr Arg Ile Met Leu Ser
    130                 135                 140
Val His Gly Ser Gln His Ser Gly Met Ile Val Gln Asp Thr Gly His
145                 150                 155                 160
Glu Thr Asp Glu Asn Arg Ala Lys Val Glu Ile Thr Pro Asn Ser Pro
                165                 170                 175
Arg Ala Glu Ala Thr Leu Gly Gly Phe Gly Ser Leu Gly Leu Asp Cys
            180                 185                 190
Glu Pro Arg Thr Gly Leu Asp Phe Ser Asp Leu Tyr Tyr Leu Thr Met
        195                 200                 205
Asn Asn Lys His Trp Leu Val His Lys Glu Trp Phe His Asp Ile Pro
    210                 215                 220
Leu Pro Trp His Ala Gly Ala Asp Thr Gly Thr Pro His Trp Asn Asn
225                 230                 235                 240
Lys Glu Ala Leu Val Glu Phe Lys Asp Ala His Ala Lys Arg Gln Thr
                245                 250                 255
Val Val Val Leu Gly Ser Gln Glu Gly Ala Val His Thr Ala Leu Ala
            260                 265                 270
Gly Ala Leu Glu Ala Glu Met Asp Gly Ala Lys Gly Arg Leu Ser Ser
        275                 280                 285
Gly His Leu Lys Cys Arg Leu Lys Met Asp Lys Leu Arg Leu Lys Gly
    290                 295                 300
Val Ser Tyr Ser Leu Cys Thr Ala Ala Phe Thr Phe Thr Lys Ile Pro
305                 310                 315                 320
Ala Glu Thr Leu His Gly Thr Val Thr Val Glu Leu Gln Tyr Ala Gly
                325                 330                 335
Thr Asp Gly Pro Cys Lys Val Pro Ala Gln Met Ala Val Asp Met Gln
            340                 345                 350
Thr Leu Thr Pro Val Gly Arg Leu Ile Thr Ala Asn Pro Val Ile Thr
        355                 360                 365
Glu Ser Thr Glu Asn Ser Lys Met Met Leu Glu Leu Asp Pro Pro Phe
    370                 375                 380
Gly Asp Ser Tyr Ile Val Ile Gly Val Gly Glu Lys Lys Ile Thr His
385                 390                 395                 400
His Trp His Arg Ser Gly Ser Thr Ile Gly Lys Ala Phe Glu Ala Thr
                405                 410                 415
Val Arg Gly Ala Lys Arg Met Ala Val Leu Gly Asp Thr Ala Trp Asp
            420                 425                 430
Phe Gly Ser Val Gly Gly Ala Leu Asn Ser Leu Gly Lys Gly Ile His
```

```
              435                 440                 445
Gln Ile Phe Gly Ala Ala Phe Lys Ser Leu Phe Gly Gly Met Ser Trp
            450                 455                 460

Phe Ser Gln Ile Leu Ile Gly Thr Leu Leu Met Trp Leu Gly Leu Asn
465                 470                 475                 480

Thr Lys Glu Gly Ser Ile Ser Leu Met Cys Leu Ala Leu Gly Gly Val
                485                 490                 495

Leu Ile Phe Leu Ser Thr Ala Val Ser Ala
            500                 505

<210> SEQ ID NO 24
<211> LENGTH: 390
<212> TYPE: DNA
<213> ORGANISM: Zika Virus

<400> SEQUENCE: 24
atggaaaaag gagcggcttt tggagtgatg gaagccctgg gaacactgcc aggacacatg        60
acagagagat tccaggaagc cattgacaac ctcgctgtgc tcatgcgggc agagactgga       120
agcaggcctt acaaagccgc ggcggcccaa ttgccggaga ccctagagac cattatgctt       180
ttggggttgc tgggaacagt ctcgctggga atcttttttcg tcttgatgag gaacaagggc       240
atagggaaga tgggctttgg aatggtgact cttggggcca gcgcatggct catgtggctc       300
tcggaaattg agccagccag aattgcatgt gtcctcattg ttgtgttcct attgctggtg       360
gtgctcatac ctgagccaga aaagcaaaga                                       390

<210> SEQ ID NO 25
<211> LENGTH: 397
<212> TYPE: DNA
<213> ORGANISM: Artificial Sequence
<220> FEATURE:
<223> OTHER INFORMATION: encodes NS4A

<400> SEQUENCE: 25
ggtgctgctt tcggtgttat ggaagctctg ggtaccctgc cgggtcacat gaccgaacgt        60
ttccaggaag ctatcgataa cctggctgtt ctgatgcgtg ctgaaaccgg ttctcgtccg       120
tacaaagctg ctgctgctca gctgccggaa accctggaaa ccatcatgct gctgggtctg       180
ctgggtaccg tttctctggg tatcttcttc gttctgatgc gtaacaaagg tatcggtaaa       240
atgggtttcg gtatggttac cctgggtgct ctgcttggc tgatgtggct gtctgaaatc       300
gaaccggctc gtatcgcttg tgttctgatc gttgttttcc tgctgctggt tgttctgatc       360
ccggaaccgg aaaaacaccg tgccggctaa tcccggg                                397

<210> SEQ ID NO 26
<211> LENGTH: 132
<212> TYPE: PRT
<213> ORGANISM: Zika Virus

<400> SEQUENCE: 26

Met Glu Lys Gly Ala Ala Phe Gly Val Met Glu Ala Leu Gly Thr Leu
1               5                   10                  15

Pro Gly His Met Thr Glu Arg Phe Gln Glu Ala Ile Asp Asn Leu Ala
            20                  25                  30

Val Leu Met Arg Ala Glu Thr Gly Ser Arg Pro Tyr Lys Ala Ala Ala
        35                  40                  45

Ala Gln Leu Pro Glu Thr Leu Glu Thr Ile Met Leu Leu Gly Leu Leu
    50                  55                  60
```

Gly Thr Val Ser Leu Gly Ile Phe Phe Val Leu Met Arg Asn Lys Gly
65                  70                  75                  80

Ile Gly Lys Met Gly Phe Gly Met Val Thr Leu Gly Ala Ser Ala Trp
                85                  90                  95

Leu Met Trp Leu Ser Glu Ile Glu Pro Ala Arg Ile Ala Cys Val Leu
            100                 105                 110

Ile Val Val Phe Leu Leu Leu Val Val Leu Ile Pro Glu Pro Glu Lys
        115                 120                 125

Gln Arg Ala Gly
    130

<210> SEQ ID NO 27
<211> LENGTH: 434
<212> TYPE: DNA
<213> ORGANISM: Artificial Sequence
<220> FEATURE:
<223> OTHER INFORMATION: His tagged sequence

<400> SEQUENCE: 27
ccatggaaaa aggtgctgct ttcggtgtta tggaagctct gggtaccctg ccgggtcaca    60
tgaccgaacg tttccaggaa gctatcgata acctggctgt tctgatgcgt gctgaaaccg   120
gttctcgtcc gtacaaagct gctgctgctc agctgccgga aaccctggaa accatcatgc   180
tgctgggtct gctgggtacc gtttctctgg gtatcttctt cgttctgatg cgtaacaaag   240
gtatcggtaa atgggtttc ggtatggtta ccctgggtgc ttctgcttgg ctgatgtggc   300
tgtctgaaat cgaaccggct cgtatcgctt gtgttctgat cgttgttttc ctgctgctgg   360
ttgttctgat cccggaaccg gaaaaacacc gtgccggcca ccatcaccat caccattagc   420
cggctaatcc cggg                                                     434

<210> SEQ ID NO 28
<211> LENGTH: 138
<212> TYPE: PRT
<213> ORGANISM: Artificial Sequence
<220> FEATURE:
<223> OTHER INFORMATION: His tagged sequence

<400> SEQUENCE: 28

Met Glu Lys Gly Ala Ala Phe Gly Val Met Glu Ala Leu Gly Thr Leu
1               5                   10                  15

Pro Gly His Met Thr Glu Arg Phe Gln Glu Ala Ile Asp Asn Leu Ala
                20                  25                  30

Val Leu Met Arg Ala Glu Thr Gly Ser Arg Pro Tyr Lys Ala Ala Ala
            35                  40                  45

Ala Gln Leu Pro Glu Thr Leu Glu Thr Ile Met Leu Leu Gly Leu Leu
        50                  55                  60

Gly Thr Val Ser Leu Gly Ile Phe Phe Val Leu Met Arg Asn Lys Gly
65                  70                  75                  80

Ile Gly Lys Met Gly Phe Gly Met Val Thr Leu Gly Ala Ser Ala Trp
                85                  90                  95

Leu Met Trp Leu Ser Glu Ile Glu Pro Ala Arg Ile Ala Cys Val Leu
            100                 105                 110

Ile Val Val Phe Leu Leu Leu Val Val Leu Ile Pro Glu Pro Glu Lys
        115                 120                 125

Gln Arg Ala Gly His His His His His His
    130                 135

<210> SEQ ID NO 29
<211> LENGTH: 756
<212> TYPE: DNA
<213> ORGANISM: Zika Virus

<400> SEQUENCE: 29

```
atggaaaatg aactcggatg gttggagaga acaaagagtg acctaagcca tctaatggga      60
aggagagagg aggggggcaac catgggattc tcaatggaca ttgacctgcg ccagcctca     120
gcttgggcca tctatgctgc cttgacaact tcattaccc cagccgtcca acatgcagtg     180
accacttcat acaacaacta ctccttaatg gcgatggcca cgcaagctgg agtgttgttt    240
ggtatgggca aagggatgcc attctacgca tgggactttg agtcccgct gctaatgata     300
ggttgctact cacaattaac gcccctgacc ctaatagtgg ccatcatttt gctcgtggcg    360
cactacatgt acttgatccc agggctgcag gcagcagctg cgcgtgctgc ccagaagaga    420
acggcagctg gcatcatgaa gaaccctgtt gtggatggaa tagtggtgac tgacattgac    480
acaatgacaa ttgaccccca agtggagaaa aagatgggag aggtgctact catggcagta    540
gccgtctcca gcgccatact gtcgcggacc gcctgggggt gggggggaggc tgggcccctg    600
atcacagccg caacttccac tttgtgggaa ggctctccga acaagtactg gaactcctct    660
acagccactt cactgtgtaa catttttagg ggaagttact tggctggagc ttctctaatc    720
tacacagtaa caagaaacgc tggcttggtc aagaga                              756
```

<210> SEQ ID NO 30
<211> LENGTH: 766
<212> TYPE: DNA
<213> ORGANISM: Artificial Sequence
<220> FEATURE:
<223> OTHER INFORMATION: encodes NS4B

<400> SEQUENCE: 30

```
aacgaactgg gttggctgga acgtaccaaa tctgatctgt ctcacctgat gggtcgtcgt      60
gaagaaggtg ctaccatggg tttctctatg gatatcgatc tgcgtccggc ttctgcttgg     120
gctatctacg ctgctctgac caccttcatc accccggctg ttcagcacgc tgttaccacc    180
tcttacaaca actactctct gatggctatg ctacccagg ctggtgttct gttcggtatg     240
ggtaaaggta tgccgttcta cgcgtgggat ttcgtgttc gctgctgat gatcggttgc      300
tactctcagc tgaccccgct gaccctgatc gttgctatca tcctgctggt tgctcactac    360
atgtacctga tccgggtct gcaggctgct gctgctcgtg ctgctcagaa cgtaccgct      420
gctggtatca tgaaaaaccc ggttgttgat ggtatcgttg ttaccgatat cgataccatg    480
accatcgatc gcagggttga aaaaaaaatg ggtcaggttc tgctgatggc tgttgctgtt    540
tcttctgcta tcctgtctcg taccgcttgg ggttgggtg aagctggtgc tctgatcacc    600
gctgctacct ctaccctgtg ggaaggttct ccgaacaaat actggaactc ttctaccgct    660
acctctctgt gcaacatctt ccgtggttct tacctggctg tgcttctct gatctacacc    720
gttacccgta acgctggtct ggttaaacgt gccggctaat c

```
  1               5                  10                 15
His Leu Met Gly Arg Arg Glu Glu Gly Ala Thr Met Gly Phe Ser Met
             20                  25                 30
Asp Ile Asp Leu Arg Pro Ala Ser Ala Trp Ala Ile Tyr Ala Ala Leu
             35                  40                 45
Thr Thr Phe Ile Thr Pro Ala Val Gln His Ala Val Thr Thr Ser Tyr
             50                  55                 60
Asn Asn Tyr Ser Leu Met Ala Met Ala Thr Gln Ala Gly Val Leu Phe
 65                  70                  75                 80
Gly Met Gly Lys Gly Met Pro Phe Tyr Ala Trp Asp Phe Gly Val Pro
                 85                  90                 95
Leu Leu Met Ile Gly Cys Tyr Ser Gln Leu Thr Pro Leu Thr Leu Ile
                100                 105                110
Val Ala Ile Ile Leu Leu Val Ala His Tyr Met Tyr Leu Ile Pro Gly
                115                 120                125
Leu Gln Ala Ala Ala Ala Arg Ala Ala Gln Lys Arg Thr Ala Ala Gly
            130                 135                 140
Ile Met Lys Asn Pro Val Val Asp Gly Ile Val Val Thr Asp Ile Asp
145                 150                 155                160
Thr Met Thr Ile Asp Pro Gln Val Glu Lys Lys Met Gly Gln Val Leu
                165                 170                175
Leu Met Ala Val Ala Val Ser Ser Ala Ile Leu Ser Arg Thr Ala Trp
            180                 185                 190
Gly Trp Gly Glu Ala Gly Ala Leu Ile Thr Ala Ala Thr Ser Thr Leu
            195                 200                 205
Trp Glu Gly Ser Pro Asn Lys Tyr Trp Asn Ser Ser Thr Ala Thr Ser
        210                 215                 220
Leu Cys Asn Ile Phe Arg Gly Ser Tyr Leu Ala Gly Ala Ser Leu Ile
225                 230                 235                240
Tyr Thr Val Thr Arg Asn Ala Gly Leu Val Lys Arg Ala Gly
                245                 250
```

<210> SEQ ID NO 32
<211> LENGTH: 800
<212> TYPE: DNA
<213> ORGANISM: Artificial Sequence
<220> FEATURE:
<223> OTHER INFORMATION: His tagged sequence

<400> SEQUENCE: 32

```
ccatggaaaa cgaactgggt tggctggaac gtaccaaatc tgatctgtct cacctgatgg    60
gtcgtcgtga agaaggtgct actatgggtt ctctatggga tatcgatctg cgtccggctt   120
ctgcttgggc tatctacgct gctctgacca ccttcatcac cccggctgtt cagcacgctg   180
ttaccacctc ttacaacaac tactctctga tggctatggc tacccaggct ggtgttctgt   240
tcggtatggg taaggtatg ccgttctacg cgtgggattt cggtgttccg ctgctgatga   300
tcggttgcta ctctcagctg accccgctga ccctgatcgt tgctatcatc ctgctggttg   360
ctcactacat gtacctgatt ccgggtctgc aggctgctgc tgctcgtgct gctcagaaac   420
gtaccgctgc tggtatcatg aaaaacccgg ttgttgatgg tatcgttgtt accgatatcg   480
ataccatgac catcgatccg caggttgaaa aaaaatggg tcaggttctg ctgatggctg   540
ttgctgtttc tttctgctatc ctgtctcgta ccgcttgggg ttggggtgaa gctggtgctc   600
tgatcaccgc tgctacctct accctgtggg aaggttctcc gaacaaatac tggaactctt   660
```
ctaccgctac ctctctgtgc aacatcttcc gtggttctta cctggctggt gcttctctga    720
tctacaccgt tacccgtaac gctggtctgg ttaaacgtgc cggccaccat caccatcacc    780
attagccggc taatcccggg                                                800

<210> SEQ ID NO 33
<211> LENGTH: 260
<212> TYPE: PRT
<213> ORGANISM: Artificial Sequence
<220> FEATURE:
<223> OTHER INFORMATION: His tagged sequence

<400> SEQUENCE: 33

Met Glu Asn Glu Leu Gly Trp Leu Glu Arg Thr Lys Ser Asp Leu Ser
1               5                   10                  15

His Leu Met Gly Arg Arg Glu Glu Gly Ala Thr Met Gly Phe Ser Met
            20                  25                  30

Asp Ile Asp Leu Arg Pro Ala Ser Ala Trp Ala Ile Tyr Ala Ala Leu
        35                  40                  45

Thr Thr Phe Ile Thr Pro Ala Val Gln His Ala Val Thr Thr Ser Tyr
    50                  55                  60

Asn Asn Tyr Ser Leu Met Ala Met Ala Thr Gln Ala Val Leu Phe
65                  70                  75                  80

Gly Met Gly Lys Gly Met Pro Phe Tyr Ala Trp Asp Phe Gly Val Pro
                85                  90                  95

Leu Leu Met Ile Gly Cys Tyr Ser Gln Leu Thr Pro Leu Thr Leu Ile
            100                 105                 110

Val Ala Ile Ile Leu Leu Val Ala His Tyr Met Tyr Leu Ile Pro Gly
        115                 120                 125

Leu Gln Ala Ala Ala Arg Ala Ala Gln Lys Arg Thr Ala Ala Gly
    130                 135                 140

Ile Met Lys Asn Pro Val Val Asp Gly Ile Val Val Thr Asp Ile Asp
145                 150                 155                 160

Thr Met Thr Ile Asp Pro Gln Val Glu Lys Lys Met Gly Gln Val Leu
                165                 170                 175

Leu Met Ala Val Ala Val Ser Ser Ala Ile Leu Ser Arg Thr Ala Trp
            180                 185                 190

Gly Trp Gly Glu Ala Gly Ala Leu Ile Thr Ala Ala Thr Ser Thr Leu
        195                 200                 205

Trp Glu Gly Ser Pro Asn Lys Tyr Trp Asn Ser Ser Thr Ala Thr Ser
    210                 215                 220

Leu Cys Asn Ile Phe Arg Gly Ser Tyr Leu Ala Gly Ala Ser Leu Ile
225                 230                 235                 240

Tyr Thr Val Thr Arg Asn Ala Gly Leu Val Lys Arg Ala Gly His His
                245                 250                 255

His His His His
            260

<210> SEQ ID NO 34
<211> LENGTH: 1816
<212> TYPE: DNA
<213> ORGANISM: Artificial Sequence
<220> FEATURE:
<223> OTHER INFORMATION: fusion protein
<220> FEATURE:
<221> NAME/KEY: misc_feature
<222> LOCATION: (1)..(1800)
<223> OTHER INFORMATION: prM-E sequence ends at nucleotide 1800
<220> FEATURE:

<221> NAME/KEY: misc_feature
<222> LOCATION: (1801)..(1816)
<223> OTHER INFORMATION: restriction site

<400> SEQUENCE: 34

```
atggaaaaag cggaggtcac tagacgtggg agtgcatact atatgtactt ggacagaaac      60
gatgctgggg aggccatatc ttttccaacc acattgggga tgaataagtg ttatatacag     120
atcatggatc ttggacacat gtgtgatgcc accatgagct atgaatgccc tatgctggat     180
gaggggtgg aaccagatga cgtcgattgt tggtgcaaca cgacgtcaac ttgggttgtg      240
tacggaacct gccatcacaa aaaggtgaa gcacggagat ctagaagaat caggtgcata     300
ggagtcagca atagggactt tgtggaaggt atgtcaggtg ggacttgggt tgatgttgtc     360
ttggaacatg gaggttgtgt caccgtaatg gcacaggaca aaccgactgt cgacatagag     420
ctggttacaa caacagtcag caacatggcg gaggtaagat cctactgcta tgaggcatca    480
atatcagaca tggcttctga cagccgctgc ccaacacaag gtgaagccta ccttgacaag    540
caatcagaca ctcaatatgt ctgcaaaaga cgttagtgg acagaggctg gggaaatgga    600
tgtggacttt ttggcaaagg agcctggtg acatgcgcta gtttgcatg ctccaagaaa       660
atgaccggga gagcatcca gccagagaat ctggagtacc ggataatgct gtcagttcat    720
ggctcccagc acagtgggat gatcgttaat gacacaggac atgaaactga tgagaataga    780
gcgaaagttg agataacgcc caattccacg agagccgaag ccaccctggg gggttttgga    840
agcctaggac ttgattgtga accgaggaca ggccttgact tttcagatttt gtattacttg    900
actatgaata caagcactg gttggttcac aaggagtggt tccacgacat tccattacct    960
tggcacgctg ggcagacac cggaactcca cactggaaca caaagaagc actggtagag       1020
ttcaaggacg cacatgccaa aaggcaaact gtcgtggttc tagggagtca agaaggagca    1080
gttcacacgg cccttgctgg agctctggag gctgagatgg atggtgcaaa gggaaggctg    1140
tcctctggcc acttgaaatg tcgcctgaaa atggataaac ttagattgaa gggcgtgtca    1200
tactccttgt gtactgcagc gttcacattc accaagatcc cggctgaaac actgcacggg    1260
acagtcacag tggagttaca gtacgcaggg acagatggac cttgcaaggt tccagctcag    1320
atggcggtgg acatgcaaac tctgaccccca gttgggaggt tgataaccgc taaccccgta    1380
atcactgaaa gcactgagaa ctctaagatg atgctggaac ttgatccacc atttgggac    1440
tcttacattg tcataggagt cggggagaag aagatcaccc accactggca caggagtggc    1500
agcaccattg gaaaagcatt tgaagccact gtgagaggtg ccaagagaat ggcagtcttg    1560
ggagacacag cctgggactt tggatcagtt ggaggcgctc tcaactcatt gggcaagggc    1620
atccatcaaa tttttggagc agcttttcaaa tcattgtttg gaggaatgtc ctggttctca    1680
caaattctca ttggaacgtt gctgatgtgg ttgggtctga acacaaagaa tggatctatt    1740
tcccttatgt gcttggcctt agggggagtg ttgatcttct tatccacagc cgtctctgct    1800
gccggctaat cccggg                                                    1816
```

<210> SEQ ID NO 35
<211> LENGTH: 1800
<212> TYPE: DNA
<213> ORGANISM: Artificial Sequence
<220> FEATURE:
<223> OTHER INFORMATION: fusion protein

<400> SEQUENCE: 35

```
atggaaaaag cggaagttac ccgtcgtggt tctgcgtact acatgtacct ggatcgcaac      60
```

-continued

```
gatgcgggtg aagcgatctc tttcccgacc accctgggta tgaacaaatg ctacatccag    120
atcatggatc tgggtcacat gtgcgatgcc accatgtctt acgaatgccc gatgctggat    180
gaaggtgttg aaccggatga tgttgattgc tggtgcaaca ccacctctac ttgggttgtt    240
tacggtacct gccaccacaa aaaggtgaa gcgcgtcgtt ctcgtcgtat ccgctgcatc     300 ggtgttteta accgtgactt cgttgaaggt atgtctggtg tacctgggt tgatgttgtt    360 ctggaacacg tggttgcgt taccgttatg gcgcaggata aaccgaccgt tgatatcgaa    420
ctggttacca ccaccgtttc taacatggcg gaagttcgtt cttactgcta cgaagcgtct    480
atctctgata tggcgtctga tagccgttgc ccgacccagg gtgaagcgta cctggataaa    540
cagtctgata cccagtacgt ttgcaaacgt accctggttg atcgtggttg gggcaacggt    600
tgcggtctgt tcggtaaagg ttctctggtt acctgcgcta attcgcatg ctctaaaaaa    660 atgaccggta aaagcatcca gccggaaaac ctggaatacc gtatcatgct gtctgttcac    720
ggctcccagc actctggtat gatcgttaac gataccggtc acgaaaccga tgaaaaccgt    780
gcgaaagttg aaatcacccc gaactctccg cgtgccgaag ccaccctggg tggtttcggt    840
tctctgggtc tggattgcga accgcgtacc ggtctggatt ctctgatct gtactacctg     900 accatgaaca caagcactg gctggttcac aaggaatggt tccacgatat cccgctgccg     960
tggcacgctg gtgcagatac cggtaccccg cactggaaca caaagaagc actggttgaa   1020 ttcaaagatg cacacgccaa acgtcagacc gttgttgttc tgggttctca ggaaggtgca   1080
gttcacaccg ccctggctgg tgctctggaa gctgaaatgg atggtgcaaa aggtcgtctg   1140
tcttctggtc acctgaaatg ccgtctgaaa atggataaac tgcgtctgaa aggtgtttct   1200
tactctctgt gcaccgcagc gttcaccttc accaaaatcc cggctgaaac cctgcacggt   1260
accgttaccg tggaactgca gtacgcaggt accgatggtc cgtgcaaagt tccggctcag   1320
atggcggtgg atatgcagac cctgaccccg gttggtcgtc tgatcaccgc taacccggtt   1380
atcaccgaat ctaccgaaaa ctctaaaatg atgctggaac tggatccgcc gttcggtgat   1440
tcttacatcg ttatcggtgt gggtgaaaaa aaaatcaccc accactggca ccgctctggc   1500
tctaccatcg gtaaagcatt cgaagccacc gttcgtggtg ccaaacgtat ggcagttctg   1560
ggtgatacag cctgggattt cggttctgtt ggtggtgctc tgaactctct gggtaaaggt   1620
atccaccaga tcttcggtgc agctttcaaa tctctgttcg gtggtatgtc ttggttctct   1680
caaatcctga tcggtaccct gctgatgtgg ctgggtctga acaccaaaaa cggttctatc   1740
tctctgatgt gcctggccct gggtggtgtt ctgatcttcc tgtctaccgc cgtttctgct   1800
```

<210> SEQ ID NO 36
<211> LENGTH: 602
<212> TYPE: PRT
<213> ORGANISM: Artificial Sequence
<220> FEATURE:
<223> OTHER INFORMATION: fusion protein

<400> SEQUENCE: 36

```
Met Glu Lys Ala Glu Val Thr Arg Arg Gly Ser Ala Tyr Tyr Met Tyr
1               5                   10                  15

Leu Asp Arg Asn Asp Ala Gly Glu Ala Ile Ser Phe Pro Thr Thr Leu
            20                  25                  30

Gly Met Asn Lys Cys Tyr Ile Gln Ile Met Asp Leu Gly His Met Cys
        35                  40                  45

Asp Ala Thr Met Ser Tyr Glu Cys Pro Met Leu Asp Glu Gly Val Glu
```

```
            50                  55                  60
Pro Asp Val Asp Cys Trp Cys Asn Thr Thr Ser Thr Trp Val Val
 65                  70                  75                  80

Tyr Gly Thr Cys His His Lys Lys Gly Glu Ala Arg Arg Ser Arg Arg
                     85                  90                  95

Ile Arg Cys Ile Gly Val Ser Asn Arg Asp Phe Val Glu Gly Met Ser
                100                 105                 110

Gly Gly Thr Trp Val Asp Val Leu Glu His Gly Gly Cys Val Thr
                115                 120                 125

Val Met Ala Gln Asp Lys Pro Thr Val Asp Ile Glu Leu Val Thr Thr
        130                 135                 140

Thr Val Ser Asn Met Ala Glu Val Arg Ser Tyr Cys Tyr Glu Ala Ser
145                 150                 155                 160

Ile Ser Asp Met Ala Ser Asp Ser Arg Cys Pro Thr Gln Gly Glu Ala
                165                 170                 175

Tyr Leu Asp Lys Gln Ser Asp Thr Gln Tyr Val Cys Lys Arg Thr Leu
                180                 185                 190

Val Asp Arg Gly Trp Gly Asn Gly Cys Gly Leu Phe Gly Lys Gly Ser
        195                 200                 205

Leu Val Thr Cys Ala Lys Phe Ala Cys Ser Lys Lys Met Thr Gly Lys
        210                 215                 220

Ser Ile Gln Pro Glu Asn Leu Glu Tyr Arg Ile Met Leu Ser Val His
225                 230                 235                 240

Gly Ser Gln His Ser Gly Met Ile Val Asn Asp Thr Gly His Glu Thr
                245                 250                 255

Asp Glu Asn Arg Ala Lys Val Glu Ile Thr Pro Asn Ser Pro Arg Ala
                260                 265                 270

Glu Ala Thr Leu Gly Gly Phe Gly Ser Leu Gly Leu Asp Cys Glu Pro
                275                 280                 285

Arg Thr Gly Leu Asp Phe Ser Asp Leu Tyr Tyr Leu Thr Met Asn Asn
        290                 295                 300

Lys His Trp Leu Val His Lys Glu Trp Phe His Asp Ile Pro Leu Pro
305                 310                 315                 320

Trp His Ala Gly Ala Asp Thr Gly Thr Pro His Trp Asn Asn Lys Glu
                325                 330                 335

Ala Leu Val Glu Phe Lys Asp Ala His Ala Lys Arg Gln Thr Val Val
                340                 345                 350

Val Leu Gly Ser Gln Glu Gly Ala Val His Thr Ala Leu Ala Gly Ala
        355                 360                 365

Leu Glu Ala Glu Met Asp Gly Ala Lys Gly Arg Leu Ser Ser Gly His
370                 375                 380

Leu Lys Cys Arg Leu Lys Met Asp Lys Leu Arg Leu Lys Gly Val Ser
385                 390                 395                 400

Tyr Ser Leu Cys Thr Ala Ala Phe Thr Phe Thr Lys Ile Pro Ala Glu
                405                 410                 415

Thr Leu His Gly Thr Val Thr Val Glu Leu Gln Tyr Ala Gly Thr Asp
                420                 425                 430

Gly Pro Cys Lys Val Pro Ala Gln Met Ala Val Asp Met Gln Thr Leu
        435                 440                 445

Thr Pro Val Gly Arg Leu Ile Thr Ala Asn Pro Val Ile Thr Glu Ser
        450                 455                 460

Thr Glu Asn Ser Lys Met Met Leu Glu Leu Asp Pro Pro Phe Gly Asp
465                 470                 475                 480
```

Ser Tyr Ile Val Ile Gly Val Gly Glu Lys Lys Ile Thr His His Trp
                485                 490                 495

His Arg Ser Gly Ser Thr Ile Gly Lys Ala Phe Glu Ala Thr Val Arg
            500                 505                 510

Gly Ala Lys Arg Met Ala Val Leu Gly Asp Thr Ala Trp Asp Phe Gly
        515                 520                 525

Ser Val Gly Gly Ala Leu Asn Ser Leu Gly Lys Gly Ile His Gln Ile
    530                 535                 540

Phe Gly Ala Ala Phe Lys Ser Leu Phe Gly Gly Met Ser Trp Phe Ser
545                 550                 555                 560

Gln Ile Leu Ile Gly Thr Leu Leu Met Trp Leu Gly Leu Asn Thr Lys
                565                 570                 575

Asn Gly Ser Ile Ser Leu Met Cys Leu Ala Leu Gly Gly Val Leu Ile
            580                 585                 590

Phe Leu Ser Thr Ala Val Ser Ala Ala Gly
        595                 600

<210> SEQ ID NO 37
<211> LENGTH: 1844
<212> TYPE: DNA
<213> ORGANISM: Artificial Sequence
<220> FEATURE:
<223> OTHER INFORMATION: fusion protein

<400> SEQUENCE: 37

```
ccatggaaaa agcggaagtt acccgtcgtg gttctgcgta ctacatgtac ctggatcgca      60
acgatgcggg tgaagcgatc tctttcccga ccaccctggg tatgaacaaa tgctacatcc     120
agatcatgga tctgggtcac atgtgcgatg ccaccatgtc ttacgaatgc ccgatgctgg     180
atgaaggtgt tgaaccggat gatgttgatt gctggtgcaa caccacctct acttgggttg     240
tttacggtac ctgccaccac aaaaaaggtg aagcgcgtcg ttctcgtcgt atccgctgca     300
tcggtgtttc taaccgtgac ttcgttgaag gtatgtctgg tggtacctgg gttgatgttg     360
ttctggaaca cggtggttgc gttaccgtta tggcgcagga taaaccgacc gttgatatcg     420
aactggttac caccaccgtt tctaacatgg cggaagttcg ttcttactgc tacgaagcgt     480
ctatctctga tatggcgtct gatagccgtt gcccgaccca gggtgaagcg tacctggata     540
aacagtctga tacccagtac gtttgcaaac gtacccggt tgatcgtggt tggggcaacg     600
gttgcggtct gttcggtaaa ggttctctgg ttacctgcgc taaattcgca tgctctaaaa     660
aaatgaccgg taaagcatc cagccggaaa acctggaata ccgtatcatg ctgtctgttc     720
acggctccca gcactctggt atgatcgtta cgataccgg tcacgaaacc gatgaaaacc     780
gtgcgaaagt tgaaatcacc ccgaactctc cgcgtgccga agccaccctg ggtggtttcg     840
gttctctggg tctggattgc gaaccgcgta ccggtctgga tttctctgat ctgtactacc     900
tgaccatgaa caacaagcac tggctggttc acaaggaatg gttccacgat atcccgctgc     960
cgtggcacgc tggtgcagat accggtaccc gcactggaa caacaaagaa gcactggttg    1020
aattcaaaga tgcacacgcc aaacgtcaga ccgttgttgt tctgggttct caggaaggtg    1080
cagttcacac cgcccggct ggtgctctgg aagctgaaat ggatggtgca aaaggtcgtc    1140
tgtcttctgg tcacctgaaa tgccgtctga aatggggataa actgcgtctg aaaggtgttt    1200
cttactctct gtgcaccgca gcgttcacct tcaccaaaat cccggctgaa acctgcacg    1260 gtaccgttac cgtggaactg cagtacgcag gtaccgatgg tccgtgcaaa gttccggctc    1320
```

```
agatggcggt ggatatgcag accctgaccc cggttggtcg tctgatcacc gctaacccgg   1380
ttatcaccga atctaccgaa aactctaaaa tgatgctgga actggatccg ccgttcggtg   1440
attcttacat cgttatcggt gtgggtgaaa aaaaaatcac ccaccactgg caccgctctg   1500
gctctaccat cggtaaagca ttcgaagcca ccgttcgtgg tgccaaacgt atggcagttc   1560
tgggtgatac agcctgggat tcggttctg ttggtggtgc tctgaactct ctgggtaaag   1620
gtatccacca gatcttcggt gcagctttca atctctgtt cggtggtatg tcttggttct   1680
ctcaaatcct gatcggtacc ctgctgatgt ggctgggtct gaacaccaaa aacggttcta   1740
tctctctgat gtgcctggcc ctgggtggtg ttctgatctt cctgtctacc gccgtttctg   1800
ctgccggcca ccatcaccat caccattagc cggctaatcc cggg   1844
```

<210> SEQ ID NO 38
<211> LENGTH: 608
<212> TYPE: PRT
<213> ORGANISM: Artificial Sequence
<220> FEATURE:
<223> OTHER INFORMATION: fusion protein

<400> SEQUENCE: 38

```
Met Glu Lys Ala Glu Val Thr Arg Arg Gly Ser Ala Tyr Tyr Met Tyr
1               5                   10                  15

Leu Asp Arg Asn Asp Ala Gly Glu Ala Ile Ser Phe Pro Thr Thr Leu
            20                  25                  30

Gly Met Asn Lys Cys Tyr Ile Gln Ile Met Asp Leu Gly His Met Cys
        35                  40                  45

Asp Ala Thr Met Ser Tyr Glu Cys Pro Met Leu Asp Glu Gly Val Glu
    50                  55                  60

Pro Asp Asp Val Asp Cys Trp Cys Asn Thr Thr Ser Thr Trp Val Val
65                  70                  75                  80

Tyr Gly Thr Cys His His Lys Lys Gly Glu Ala Arg Arg Ser Arg Arg
                85                  90                  95

Ile Arg Cys Ile Gly Val Ser Asn Arg Asp Phe Val Glu Gly Met Ser
            100                 105                 110

Gly Gly Thr Trp Val Asp Val Val Leu Glu His Gly Gly Cys Val Thr
        115                 120                 125

Val Met Ala Gln Asp Lys Pro Thr Val Asp Ile Glu Leu Val Thr Thr
    130                 135                 140

Thr Val Ser Asn Met Ala Glu Val Arg Ser Tyr Cys Tyr Glu Ala Ser
145                 150                 155                 160

Ile Ser Asp Met Ala Ser Asp Ser Arg Cys Pro Thr Gln Gly Glu Ala
                165                 170                 175

Tyr Leu Asp Lys Gln Ser Asp Thr Gln Tyr Val Cys Lys Arg Thr Leu
            180                 185                 190

Val Asp Arg Gly Trp Gly Asn Gly Cys Gly Leu Phe Gly Lys Gly Ser
        195                 200                 205

Leu Val Thr Cys Ala Lys Phe Ala Cys Ser Lys Lys Met Thr Gly Lys
    210                 215                 220

Ser Ile Gln Pro Glu Asn Leu Glu Tyr Arg Ile Met Leu Ser Val His
225                 230                 235                 240

Gly Ser Gln His Ser Gly Met Ile Val Asn Asp Thr Gly His Glu Thr
                245                 250                 255

Asp Glu Asn Arg Ala Lys Val Glu Ile Thr Pro Asn Ser Pro Arg Ala
            260                 265                 270
```

-continued

```
Glu Ala Thr Leu Gly Gly Phe Gly Ser Leu Gly Leu Asp Cys Glu Pro
            275                 280                 285

Arg Thr Gly Leu Asp Phe Ser Asp Leu Tyr Tyr Leu Thr Met Asn Asn
    290                 295                 300

Lys His Trp Leu Val His Lys Glu Trp Phe His Asp Ile Pro Leu Pro
305                 310                 315                 320

Trp His Ala Gly Ala Asp Thr Gly Thr Pro His Trp Asn Asn Lys Glu
                325                 330                 335

Ala Leu Val Glu Phe Lys Asp Ala His Ala Lys Arg Gln Thr Val Val
            340                 345                 350

Val Leu Gly Ser Gln Glu Gly Ala Val His Thr Ala Leu Ala Gly Ala
            355                 360                 365

Leu Glu Ala Glu Met Asp Gly Ala Lys Gly Arg Leu Ser Ser Gly His
    370                 375                 380

Leu Lys Cys Arg Leu Lys Met Asp Lys Leu Arg Leu Lys Gly Val Ser
385                 390                 395                 400

Tyr Ser Leu Cys Thr Ala Ala Phe Thr Phe Thr Lys Ile Pro Ala Glu
                405                 410                 415

Thr Leu His Gly Thr Val Thr Val Glu Leu Gln Tyr Ala Gly Thr Asp
            420                 425                 430

Gly Pro Cys Lys Val Pro Ala Gln Met Ala Val Asp Met Gln Thr Leu
            435                 440                 445

Thr Pro Val Gly Arg Leu Ile Thr Ala Asn Pro Val Ile Thr Glu Ser
    450                 455                 460

Thr Glu Asn Ser Lys Met Met Leu Glu Leu Asp Pro Pro Phe Gly Asp
465                 470                 475                 480

Ser Tyr Ile Val Ile Gly Val Gly Glu Lys Lys Ile Thr His His Trp
                485                 490                 495

His Arg Ser Gly Ser Thr Ile Gly Lys Ala Phe Glu Ala Thr Val Arg
                500                 505                 510

Gly Ala Lys Arg Met Ala Val Leu Gly Asp Thr Ala Trp Asp Phe Gly
            515                 520                 525

Ser Val Gly Gly Ala Leu Asn Ser Leu Gly Lys Gly Ile His Gln Ile
530                 535                 540

Phe Gly Ala Ala Phe Lys Ser Leu Phe Gly Gly Met Ser Trp Phe Ser
545                 550                 555                 560

Gln Ile Leu Ile Gly Thr Leu Leu Met Trp Leu Gly Leu Asn Thr Lys
                565                 570                 575

Asn Gly Ser Ile Ser Leu Met Cys Leu Ala Leu Gly Gly Val Leu Ile
            580                 585                 590

Phe Leu Ser Thr Ala Val Ser Ala Ala Gly His His His His His His
            595                 600                 605
```

I claim:

1. A genetically modified recombinant derivative of a facultative intracellular invasive bacterial pathogen that delivers synthesized ZIKV protein antigens that are encoded by codon optimized nucleotide sequences and/or exhibit in vivo regulated delayed attenuation, regulated delayed synthesis of protective ZIKV antigens and regulated delayed lysis with delivery of non-glycosylated ZIKV antigens to induce mucosal and systemic antibody responses and protective mucosal and systemic cellular immune responses specific to ZIKV, wherein:

said mucosal and systemic antibody responses and protective mucosal and systemic cellular immune responses are specific to ZIKV and do not cross react with other flaviviruses; and said genetically modified recombinant derivative of a facultative intracellular invasive bacterial pathogen comprises a regulated delayed lysis plasmid vector that provides for expression of ZIKV protein antigens that are encoded by one or more nucleic acid molecules comprising SEQ ID NOs: 2, 5, 8, 12, 16, 17, 20, 21, 25, 27, 30, 32 or 35.

2. The genetically modified recombinant derivative of a facultative intracellular invasive bacterial pathogen of claim 1, wherein said flavivirus is a Dengue virus.

3. The genetically modified recombinant derivative of a facultative intracellular invasive bacterial pathogen of claim 1, wherein said genetically modified recombinant derivative of a facultative intracellular invasive bacterial pathogen possesses one or more mutations that enables escape from the pathogen containing vesicle (PSC) into the cytosol for regulated cell lysis for delivery of protein antigens to the proteosome to enhance induction of antigen-specific cellular immune responses.

4. The genetically modified recombinant derivative of a facultative intracellular invasive bacterial pathogen of claim 1, wherein the regulated phenotypes are dependent on the addition of two sugars during growth of the recombinant bacterium.

5. The genetically modified recombinant derivative of a facultative intracellular invasive bacterial pathogen of claim 4, wherein the two sugars are arabinose and mannose.

6. A vaccine composition, the composition comprising a recombinant bacterium according to claim 1.

7. A method of inducing immunity to ZIKV, the method comprising administering an effective amount of a vaccine composition of claim 6 to an animal host.

8. A recombinant attenuated *Salmonella* vaccine (RASV) strain comprising a nucleic acid sequence encoding a ZIKA virus (ZIKV) antigen selected from glycosylated or non-glycosylated ZIKV capsid (C), membrane precursor (prM), envelope (E) proteins, NS1, NS2A, NS2B, NS3, NS4A, 2K, NS4B, NS5 fusion proteins comprising two or more of said glycosylated or non-glycosylated antigens to induce mucosal and systemic antibody responses and protective mucosal and systemic cellular immune responses with such immune responses specific to ZIKV and not cross reacting with other flaviviruses and may, optionally, be codon optimized and/or engineered for translational acceleration or delay, said RASV comprising a $\Delta pagP88::P_{trc}$ lpxE mutation and expressing a non-toxic adjuvant form of LPS lipid A monophosphoryl lipid A (MPLA) and the following genetic modifications:
   a) ($\Delta P_{murA25}$::TT araC $P_{BAD}$ murA; $\Delta asdA27$::TT araC $P_{BAD}$ c2 $\Delta pmi$-2426; $\Delta$(wza-wcaM)-8 $\Delta relA197$::araC $P_{BAD}$ lacI TT; and $\Delta recF126$ $\Delta sifA26$); or
   b) ($\Delta P_{murA25}$::TT araC $P_{BAD}$ murA; $\Delta asdA27$::TT araC $P_{BAD}$ c2; $\Delta$(wza-wcaM)-8 $\Delta pmi$-2426; $\Delta relA1123$; $\Delta recF126$; $\Delta endA2113$; $\Delta sseL116$; $\Delta tlpA181$; and $\Delta P_{hilA}::P_{trc\ \Delta lacO888}$hilA).

9. The RASV strain according to claim 8, wherein said fusion protein comprises NS1-NS2A-NS2B-NS3 or ZIKV NS4A-2K-NS4B-NS5 which may, optionally, be codon-optimized and/or engineered for translational acceleration or delay.

10. A vaccine composition comprising a RASV strain according to claim 8 and a pharmaceutically acceptable carrier.

11. A method of inducing an immune response in a host comprising the administration of a RASV strain according to claim 8 to a host.

* * * * *

UNITED STATES PATENT AND TRADEMARK OFFICE
CERTIFICATE OF CORRECTION

PATENT NO. : 11,136,354 B2  
APPLICATION NO. : 16/319363  
DATED : October 5, 2021  
INVENTOR(S) : Roy Curtiss, III Page 1 of 1

It is certified that error appears in the above-identified patent and that said Letters Patent is hereby corrected as shown below:

In the Specification

Column 20,
Line 29, "of me-dependent" should read --of rne-dependent--.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*